(12) United States Patent
Sah et al.

(10) Patent No.: US 9,212,364 B2
(45) Date of Patent: Dec. 15, 2015

(54) COMPOSITIONS AND METHODS FOR INHIBITING EXPRESSION OF MUTANT EGFR GENE

(71) Applicants: Dinah Sah, Boston, MA (US); Pamela Tan, Kulmbach (DE); Webster Cavenee, La Jolla, CA (US); Frank Furnari, La Jolla, CA (US); Maria del Mar Inda Perez, La Jolla, CA (US); Rudy Bonavia, La Jolla, CA (US)

(72) Inventors: Dinah Sah, Boston, MA (US); Pamela Tan, Kulmbach (DE); Webster Cavenee, La Jolla, CA (US); Frank Furnari, La Jolla, CA (US); Maria del Mar Inda Perez, La Jolla, CA (US); Rudy Bonavia, La Jolla, CA (US)

(73) Assignees: Alnylam Pharmaceuticals, Inc., Cambridge, MA (US); Ludwig Institute for Cancer Research Ltd., New York, NY (US)

( * ) Notice: Subject to any disclaimer, the term of this patent is extended or adjusted under 35 U.S.C. 154(b) by 0 days.

(21) Appl. No.: 13/659,315

(22) Filed: Oct. 24, 2012

(65) Prior Publication Data
US 2013/0184329 A1    Jul. 18, 2013

Related U.S. Application Data

(63) Continuation of application No. 13/061,569, filed as application No. PCT/US2009/055745 on Sep. 2, 2009, now Pat. No. 8,318,693.

(60) Provisional application No. 61/095,487, filed on Sep. 9, 2008, provisional application No. 61/166,488, filed on Apr. 3, 2009, provisional application No. 61/147,668, filed on Jan. 27, 2009, provisional application No. 61/147,680, filed on Jan. 27, 2009, provisional application No. 61/093,620, filed on Sep. 2, 2008.

(51) Int. Cl.
| | |
|---|---|
| A61K 48/00 | (2006.01) |
| C07H 21/02 | (2006.01) |
| C07H 21/04 | (2006.01) |
| C12N 15/113 | (2010.01) |
| A61K 31/713 | (2006.01) |

(52) U.S. Cl.
CPC .......... *C12N 15/1138* (2013.01); *A61K 31/713* (2013.01); *C12N 2310/14* (2013.01); *C12N 2310/321* (2013.01); *C12N 2310/3515* (2013.01); *C12N 2320/31* (2013.01)

(58) Field of Classification Search
CPC .............................. A61K 48/00; C12N 15/113
See application file for complete search history.

(56) References Cited

U.S. PATENT DOCUMENTS

| 6,224,868 B1 | 5/2001 | Wong et al. |
| 2008/0234218 A1 | 9/2008 | Sohn et al. |

FOREIGN PATENT DOCUMENTS

| WO | 03/070912 A2 | 8/2003 |
| WO | 2005/054270 A2 | 6/2005 |
| WO | 2007/064846 A2 | 6/2007 |

OTHER PUBLICATIONS

Arwert et al., "Visualizing the Dynamics of EGFR Activity and Antiglioma Therapies In Vivo," Cancer Research (2007) 67(15):7335-7342.
Bachoo et al., "Eipdermal Growth Factor Receptor and Ink4a/Arf: Convergent Mechanisms Governing Terminal Differentiation and Transformation Along the Neural Stem Cell to Astrocyte Axis," Cancer Cell (2002) 1(3):269-77.
Fan et al., "RNA Interference Against a Glioma-Derived Allele of EGFR Induces Blockade at G2M," Oncogene (2005) 24(5):829-837.
Furnari et al., "Malignant Astrocytic Glioma: Genetics, Biology, and Paths to Treatment," Genes Dev (2007) 21 (21):2683-710.
International Search Report dated Feb. 11, 2010 for PCT/US2009/055745.
Lal et al., "An Implantable Guide-Screw System for Brain Tumor Studies in Small Animals," J. Neurosurg. (2000) 92 (2):326-333.
Nishikawa et al., Proc. Natl. Acad. Sci. USA (1994) 91:7727-7731.
Oussenko et al., "SiRNAs Against Deletion Mutant EGFR in the Treatment of Glioblastoma Multiforme (GBM)," Proceedings of the American Association for Cancer Research Annual Meeting, Apr. 2007, 48:1140.
Shir et al., "Inhibition of Glioma Growth by Tumor-Specific Activation of Double-Stranded RNA-Dependent Protein Kinase PKR," Nature Biotechnology (2002) 20(9):895-900.
Yamoutpour et al., "Gene Silencing for Eipdermal Growth Factor Receptor Variant III Induces Cell-Specific Cytotoxicity," Molecular Cancer Therapeutics (2008) 7(11):3586-3597.
International Preliminary Report on Patentability and Written Opinion, International Application No. PCT/US2009/055745, dated Mar. 8, 2011.
Maria del Mar Inda, et al., "Tumor Heterogeneity is an Active Process Maintained by a Mutant EGFR-Induced Cytokine Circuit in Glioblastoma," Genes & Development, 24:1731-1745 (2010).
European Search Report dated Apr. 3, 2014 from European Application No. 13179293.9.
Colomiere M et al., "Cross Talk of Signals Between EGFR and IL-6R Through JAK2/STAT3 Mediate Epithelial-Mesenchymal Transition in Ovarian Carcinomas", British Journal of Cancer, vol. 100, pp. 134-144, Jan. 1, 2009.
Fan et al., "Combinatorial Efficacy Achieved Through Two-Point Blockade Within a Signaling Pathway—A Chemical Genetic Approach", Cancer Research, vol. 63, No. 24, Dec. 15, 2003, pp. 8930-8938.

(Continued)

*Primary Examiner* — Amy Bowman
(74) *Attorney, Agent, or Firm* — Lando & Anastasi, LLP

(57) ABSTRACT

The invention relates to a double-stranded ribonucleic acid (dsRNA) targeting a mutant Epidermal Growth Factor Receptor (EGFR), and methods of using the dsRNA to inhibit expression of mutant EGFR.

21 Claims, 26 Drawing Sheets

(56) References Cited

OTHER PUBLICATIONS

Lee et al, "Epigenetic modification of SOCS-1 differentially regulates STAT3 activation in response to interleukin-6 receptor and epidermal growth factor receptor signaling through JAK and/or MEK in head and neck squamous cell carcinomas", Molecular Cancer Therapeutics, vol. 5, No. 1, Jan. 1, 2006, pp. 8-19.

Schafer et al., "IL-6 involvement in epithelial cancers", Journal of Clinical Investigation, vol. 117, No. 12, Dec. 3, 2007, pp. 3660-3663.

Gao et al., "Mutations in the EGFR kinase domain mediate STAT3 activation via IL-6 production in human lung adenocarcinomas", Journal of Clinical Investigation, vol. 117, No. 12, Dec. 3, 2007, pp. 3846-3856.

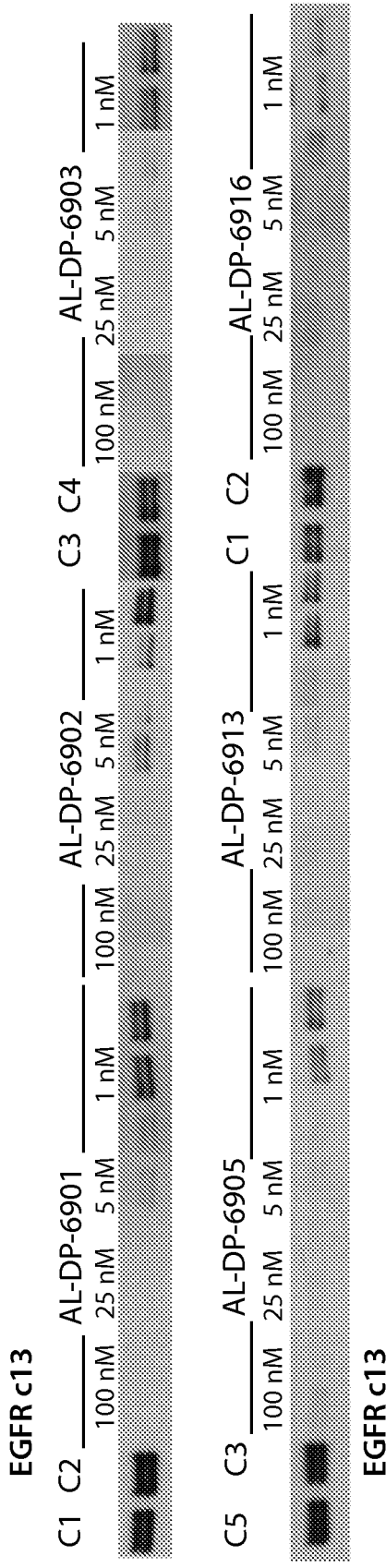
Fig. 7A
Fig. 7B

```
   1 cattctgccc tcgagcccac cgggaacgaa agagaagctc tatctcccct ccaggagccc
  61 agctatgaac tccttctcca caagcgcctt cggtccagtt gccttctccc tggggctgct
 121 cctggtgttg cctgctgcct tccctgcccc agtaccccca ggagaagatt ccaaagatgt
 181 agccgcccca cacagacagc cactcacctc ttcagaacga attgacaaac aaattcggta
 241 catcctcgac ggcatctcag ccctgagaaa ggagacatgt aacaagagta acatgtgtga
 301 aagcagcaaa gaggcactgg cagaaaacaa cctgaacctt ccaaagatgg ctgaaaaaga
 361 tggatgcttc caatctggat tcaatgagga gacttgcctg gtgaaaatca tcactggtct
 421 tttggagttt gaggtatacc tagagtacct ccagaacaga tttgagagta gtgaggaaca
 481 agccagagct gtgcagatga gtacaaaagt cctgatccag ttcctgcaga aaaaggcaaa
 541 gaatctagat gcaataacca cccctgaccc aaccacaaat gccagcctgc tgacgaagct
 601 gcaggcacag aaccagtggc tgcaggacat gacaactcat ctcattctgc gcagctttaa
 661 ggagttcctg cagtccagcc tgagggctct tcggcaaatg tagcatgggc acctcagatt
 721 gttgttgtta atgggcattc cttcttctgg tcagaaacct gtccactggg cacagaactt
 781 atgttgttct ctatggagaa ctaaaagtat gagcgttagg acactatttt aattattttt
 841 aatttattaa tatttaaata tgtgaagctg agttaattta tgtaagtcat atttatattt
 901 ttaagaagta ccacttgaaa cattttatgt attagttttg aaataataat ggaaagtggc
 961 tatgcagttt gaatatcctt tgtttcagag ccagatcatt tcttggaaag tgtaggctta
1021 cctcaaataa atggctaact tatacatatt tttaaagaaa tatttatatt gtatttatat
1081 aatgtataaa tggtttttat accaataaat ggcattttaa aaaattcagc a
```

Fig. 11

```
   1 ccccggcgca gcgcggccgc agcagcctcc gcccccgca cggtgtgagc gcccgacgcg
  61 gccgaggcgg ccggagtccc gagctagccc cggcggccgc cgccgcccag accggacgac
 121 aggccacctc gtcggcgtcc gcccgagtcc ccgcctcgcc gccaacgcca caaccaccgc
 181 gcacggcccc ctgactccgt ccagtattga tcgggagagc cggagcgagc tcttcgggga
 241 gcagcgatgc gaccctccgg gacggccggg gcagcgctcc tggcgctgct ggctgcgctc
 301 tgcccggcga gtcgggctct ggaggaaaag aaagtttgcc aaggcacgag taacaagctc
 361 acgcagttgg gcacttttga agatcatttt ctcagcctcc agaggatgtt caataactgt
 421 gaggtggtcc ttgggaattt ggaaattacc tatgtgcaga ggaattatga tctttccttc
 481 ttaaagacca tccaggaggt ggctggttat gtcctcattg ccctcaacac agtggagcga
 541 attcctttgg aaaacctgca gatcatcaga ggaaatatgt actacgaaaa ttcctatgcc
 601 ttagcagtct tatctaacta tgatgcaaat aaaaccggac tgaaggagct gcccatgaga
 661 aatttacagg aaatcctgca tggcgccgtg cggttcagca caaccctgc cctgtgcaac
 721 gtggagagca tccagtggcg ggacatagtc agcagtgact ttctcagcaa catgtcgatg
 781 gacttccaga accacctggg cagctgccaa aagtgtgatc caagctgtcc aatgggagc
 841 tgctgggtg caggagagga gaactgccag aaactgacca aaatcatctg tgcccagcag
 901 tgctccggc gctgccgtgg caagtccccc agtgactgct gccacaacca gtgtgctgca
 961 ggctgcacag gccccggga gagcgactgc ctggtctgcc gcaaattccg agacgaagcc
1021 acgtgcaagg acacctgccc cccactcatg ctctacaacc ccaccacgta ccagatggat
1081 gtgaaccccg agggcaaata cagctttggt gccacctgcg tgaagaagtg tccccgtaat
1141 tatgtggtga cagatacgg ctcgtgcgtc cgagcctgtg gggccgacag ctatgagatg
1201 gaggaagacg gcgtccgcaa gtgtaagaag tgcgaagggc cttgccgcaa agtgtgtaac
1261 ggaataggta ttggtgaatt taaagactca ctctccataa atgctacgaa tattaaacac
1321 ttcaaaaact gcacctccat cagtggcgat ctccacatcc tgccggtggc atttagggt
1381 gactccttca cacatactcc tcctctggat ccacaggaac tggatattct gaaaaccgta
1441 aaggaaatca caggttttt gctgattcag gcttggcctg aaaacaggac ggacctccat
1501 gcctttgaga acctagaaat catacgcggc aggaccaagc aacatggtca gttttctctt
1561 gcagtcgtca gcctgaacat aacatccttg ggattacgct ccctcaagga gataagtgat
1621 ggagatgtga atttcagg aaacaaaaat ttgtgctatg caaatacaat aaactggaaa
1681 aaactgtttg ggacctccgg tcagaaaacc aaaattataa gcaacagagg tgaaaacagc
1741 tgcaaggcca caggccaggt ctgccatgcc ttgtgctccc cgagggctg ctggggcccg
1801 gagcccaggg actgcgtctc ttgccggaat gtcagccgag cagggaatg cgtggacaag
1861 tgcaaccttc tggagggtga gccaagggag tttgtggaga actctgagtg catacagtgc
1921 cacccagagt gcctgcctca ggccatgaac atcacctgca caggacgggg accagacaac
1981 tgtatccagt gtgcccacta cattgacggc ccccactgcg tcaagacctg cccggcagga
2041 gtcatgggag aaaacaacac cctggtctgg aagtacgcag acgccggcca tgtgtgccac
2101 ctgtgccatc caaactgcac ctacggatgc actgggccag gtcttgaagg ctgtccaacg
2161 aatgggccta agatcccgtc catcgccact gggatggtgg gggcctcct cttgctgctg
2221 gtggtggccc tggggatcgg cctcttcatg cgaaggcgcc acatcgttcg gaagcgcacg
2281 ctgcggaggc tgctgcagga gagggagctt gtggagcctc ttacacccag tggagaagct
2341 cccaaccaag ctctcttgag gatcttgaag gaaactgaat tcaaaaagat caaagtgctg
2401 ggctccggtg cgttcggcac ggtgtataag ggactctgga tcccagaagg tgagaaagtt
2461 aaaattcccg tcgctatcaa ggaattaaga gaagcaacat ctccgaaagc caacaaggaa
2521 atcctcgatg aagcctacgt gatggccagc gtggacaacc ccacgtgtg ccgcctgctg
2581 ggcatctgcc tcacctccac cgtgcagctc atcacgcagc tcatgccctt cggctgcctc
2641 ctggactatg tccggaaca caaagacaat attggctccc agtacctgct caactggtgt
2701 gtgcagatcg caaagggcat gaactacttg gaggaccgtc gcttggtgca ccgcgacctg
2761 gcagccagga acgtactggt gaaaaccccg cagcatgtca agatcacaga ttttgggctg
```

Fig. 21A

```
2821 gccaaactgc tgggtgcgga agagaaagaa taccatgcag aaggaggcaa agtgcctatc
2881 aagtggatgg cattggaatc aatttttacac agaatctata cccaccagag tgatgtctgg
2941 agctacgggg tgaccgtttg ggagttgatg acctttggat ccaagccata tgacggaatc
3001 cctgccagcg agatctcctc catcctggag aaaggagaac gcctccctca gccacccata
3061 tgtaccatcg atgtctacat gatcatggtc aagtgctgga tgatagacgc agatagtcgc
3121 ccaaagttcc gtgagttgat catcgaattc tccaaaatgg cccgagaccc ccagcgctac
3181 cttgtcattc agggggatga agaatgcat ttgccaagtc ctacagactc caacttctac
3241 cgtgccctga tggatgaaga agacatggac gacgtggtgg atgccgacga gtacctcatc
3301 ccacagcagg gcttcttcag cagcccctcc acgtcacgga ctcccctcct gagctctctg
3361 agtgcaacca gcaacaattc caccgtggct tgcattgata gaaatgggct gcaaagctgt
3421 cccatcaagg aagacagctt cttgcagcga tacagctcag accccacagg cgccttgact
3481 gaggacagca tagacgacac cttcctccca gtgcctgaat acataaacca gtccgttccc
3541 aaaaggcccg ctggctctgt gcagaatcct gtctatcaca atcagcctct gaaccccgcg
3601 cccagcagag acccacacta ccaggacccc cacagcactg cagtgggcaa ccccgagtat
3661 ctcaacactg tccagcccac ctgtgtcaac agcacattcg acagccctgc ccactgggcc
3721 cagaaaggca gccaccaaat tagcctggac aaccctgact accagcagga cttctttccc
3781 aaggaagcca agccaaatgg catctttaag ggctccacag ctgaaaatgc agaataccta
3841 agggtcgcgc cacaaagcag tgaatttatt ggagcatgac cacggaggat agtatgagcc
3901 ctaaaaatcc agactctttc gatacccagg accaagccac agcaggtcct ccatcccaac
3961 agccatgccc gcattagctc ttagacccac agactggttt gcaacgtttt acaccgacta
4021 gccaggaagt acttccacct cgggcacatt tgggaagttt gcattccttt gtcttcaaac
4081 tgtgaagcat ttacagaaac gcatccagca agaatattgt cccttttgagc agaaatttat
4141 ctttcaaaga ggtatatttg aaaaaaaaaa aaagtatatg tgaggatttt tattgattgg
4201 ggatcttgga gtttttcatt gtcgctattg atttttactt caatgggctc ttccaacaag
4261 gaagaagctt gctggtagca cttgctaccc tgagttcatc caggcccaac tgtgagcaag
4321 gagcacaagc cacaagtctt ccagaggatg cttgattcca gtggttctgc ttcaaggctt
4381 ccactgcaaa acactaaaga tccaagaagg ccttcatggc cccagcaggc cggatcggta
4441 ctgtatcaag tcatggcagg tacagtagga taagccactc tgtccctttcc tgggcaaaga
4501 agaaacggag gggatggaat tcttccttag acttacttt gtaaaaatgt ccccacggta
4561 cttactcccc actgatggac cagtggttc cagtcatgag cgttagactg acttgtttgt
4621 cttccattcc attgttttga aactcagtat gctgcccctg tcttgctgtc atgaaatcag
4681 caagagagga tgacacatca ataataact cggattccag cccacattgg attcatcagc
4741 atttggacca atagcccaca gctgagaatg tggaatacct aaggatagca ccgcttttgt
4801 tctcgcaaaa acgtatctcc taatttgagg ctcagatgaa atgcatcagg tcctttgggg
4861 catagatcag aagactacaa aaatgaagct gctctgaaat ctcctttagc catcaccca
4921 accccccaaa attagttttgt gttacttatg aagatagtt ttctccttt acttcacttc
4981 aaaagctttt tactcaaaga gtatatgttc cctccaggtc agctgccccc aaaccccctc
5041 cttacgcttt gtcacacaaa aagtgtctct gccttgagtc atctattcaa gcacttacag
5101 ctctggccac aacagggcat tttacaggtg cgaatgacag tagcattatg agtagtgtgg
5161 aattcaggta gtaaatatga aactagggtt tgaaattgat aatgctttca caacatttgc
5221 agatgtttta gaaggaaaaa agttccttcc taaataatt tctctacaat tggaagattg
5281 gaagattcag ctagttagga gccaccttt tttcctaatc tgtgtgtgcc ctgtaacctg
5341 actggttaac agcagtcctt tgtaaacagt gttttaaact ctcctagtca atatccaccc
5401 catccaattt atcaaggaag aaatggttca gaaaatattt tcagcctaca gttatgttca
5461 gtcacacaca catacaaaat gttccttttg cttttaaagt aatttttgac tcccagatca
5521 gtcagagccc ctacagcatt gttaagaaag tatttgattt ttgtctcaat gaaaataaaa
5581 ctatattcat ttccactcta aaaaaaaaa aaaaaa
```

Fig. 21B

COMPOSITIONS AND METHODS FOR INHIBITING EXPRESSION OF MUTANT EGFR GENE

RELATED APPLICATIONS

This application is a continuation of U.S. application Ser. No. 13/061,569, filed Jul. 21, 2011, now U.S. Pat. No. 8,318,693, which is a national phase application under 35 U.S.C. §371 of PCT International Application No. PCT/US2009/055745, filed Sep. 2, 2009, which claims the benefit of U.S. Provisional Application No. 61/093,620, filed Sep. 2, 2008, U.S. Provisional Application No. 61/095,487, filed Sep. 9, 2008, U.S. Provisional Application No. 61/147,668, filed Jan. 27, 2009, U.S. Provisional Application No. 61/147,680, filed Jan. 27, 2009, and U.S. Provisional Application No. 61/166,488, filed Apr. 3, 2009. Each of these prior applications is incorporated herein by reference in its entirety.

FIELD OF THE INVENTION

The invention relates to a double-stranded ribonucleic acid (dsRNA) targeting a mutant Epidermal Growth Factor Receptor (EGFR), and methods of using the dsRNA to inhibit expression of mutant EGFR.

BACKGROUND OF THE INVENTION

The Epidermal Growth Factor Receptor (EGFR) gene is frequently upregulated in carcinomas of the breast, kidney, ovary, cervix, and in squamous cells. The upregulation is typically due to gene amplification or overexpression. EGFR upregulation in gliomas is most often associated with the rearrangement of the EGFR gene resulting in alterations of its transcript so that such gliomas express both wild-type endogenous EGFR as well as the episomal mutant form. The most common of the rearrangements are genomic alterations leading to deletion of exons 2-7 in the EGFR mRNA (called ds 2-7 EGFR, deltaEGFR, EGFR-de2-7, or EGFRvIII), which causes an in-frame truncation of 801 bp in the extracellular domain of the molecule. The EGFR gene is amplified in >50% of glioblastomas. This amplification is often associated with expression of deltaEGFR, which conveys enhanced tumor aggressiveness.

Double-stranded RNA molecules (dsRNA) have been shown to block gene expression in a highly conserved regulatory mechanism known as RNA interference (RNAi). WO 99/32619 (Fire et al.) disclosed the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.).

SUMMARY OF THE INVENTION

The invention provides compositions containing double-stranded ribonucleic acid (dsRNA) and methods for inhibiting the expression of a mutant EGFR gene, such as a deltaEGFR gene, in a cell or mammal. The invention also provides compositions and methods for treating pathological conditions and diseases caused by the expression of deltaEGFR gene, such as cancer, including glioma. The dsRNAs included in the compositions featured herein include a dsRNA having an RNA strand (the antisense strand) having a region which is less than 30 nucleotides in length, generally 19-24 nucleotides in length, and is substantially complementary to at least part of an mRNA transcript of the deltaEGFR gene. In some embodiments, the dsRNA also targets a wildtype mRNA transcript of the EGFR gene.

In one embodiment, a dsRNA for inhibiting expression of a deltaEGFR gene includes at least two sequences that are complementary to each other. The dsRNA includes a sense strand having a first sequence and an antisense strand having a second sequence. The antisense strand includes a nucleotide sequence that is substantially complementary to at least part of an mRNA encoding deltaEGFR, and the region of complementarity is less than 30 nucleotides in length, and at least 15 nucleotides in length. Generally, the dsRNA is 19 to 24, e.g., 19 to 21 nucleotides in length. In some embodiments the dsRNA is from about 10 to about 15 nucleotides in length, and in other embodiments the dsRNA is from about 25 to about 30 nucleotides in length. The dsRNA, upon contacting with a cell expressing deltaEGFR, inhibits the expression of the deltaEGFR gene by at least 20%, at least 25%, at least 30%, at least 35%, or at least 40%, such as when assayed by a method as described herein. In one embodiment, the deltaEGFR dsRNA is formulated in a stable nucleic acid particle (SNALP).

For example, the dsRNA molecules featured herein can include a first sequence of the dsRNA that is selected from the group consisting of the sense sequences of Tables 2, 3 and 4, and a second sequence that is selected from the group consisting of the antisense sequences of Tables 2, 3 and 4. The dsRNA molecules featured herein can include naturally occurring nucleotides or can include at least one modified nucleotide, such as a 2'-O-methyl modified nucleotide, a nucleotide having a 5'-phosphorothioate group, and a terminal nucleotide linked to a conjugate group, such as a cholesteryl derivative or a vitamin E group. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such modified sequence will be based on a first sequence of said dsRNA selected from the group consisting of the sense sequences of Tables 2, 3 and 4 and a second sequence selected from the group consisting of the antisense sequences of Tables 2, 3 and 4.

In one aspect, an interleukin-6 (IL6) dsRNA is also featured in the invention, and the IL-6 dsRNA is capable of decreasing levels of IL6 protein secretion in cultured cells, e.g., human cultured cells. In one embodiment, the cultured cells are U87-ΔEGFR cells. In another embodiment, the IL-6 dsRNA is capable of decreasing IL6 secretion into culture supernatant by 20%, 30%, 40%, 50%, 60%, 70%, 80%, 85%, 90% or more. In yet another embodiment, the IL6 dsRNA is capable of reducing tumor volume in an animal model, such as in a mouse, rat, or primate model. In another embodiment, a first sequence of an IL6 dsRNA is selected from the group consisting of the sense sequences of Tables 5, 6, 7, and 8, a second sequence is selected from the group consisting of the antisense sequences of Tables 5, 6, 7, and 8.

In another aspect, the invention provides a cell containing at least one of the dsRNAs featured in the invention. The cell is generally a mammalian cell, such as a human cell.

In yet another aspect, the invention provides a pharmaceutical composition for inhibiting the expression of a deltaEGFR gene in an organism, generally a human subject. The composition typically includes one or more of the dsRNAs described herein and a pharmaceutically acceptable carrier or delivery vehicle. In one embodiment, the composition is used for treating cancer, e.g., a glioma.

In another embodiment, the pharmaceutical composition is formulated for administration of a dosage regimen described herein, e.g., not more than once every four weeks, not more than once every three weeks, not more than once every two weeks, or not more than once every week. In another embodiment, the pharmaceutical composition can be maintained for a month or longer, e.g., one, two, three, or six months, or one year or longer.

In another embodiment, a composition containing a dsRNA featured in the invention, e.g., a dsRNA targeting deltaEGFR, is administered with a non-dsRNA therapeutic agent, such as an agent known to treat a cancer, such as a glioma. For example, a dsRNA featured in the invention can be administered with, e.g, a chemotherapeutic agent, such as temozolomide, or with radiation therapy.

In one embodiment, the composition further includes a dsRNA having at least two sequences that are complementary to each other, and where a sense strand includes a region of complementarity that is substantially complementary to at least a part of an mRNA encoding an IL6 protein, and where the region of complementarity is less than 30 nucleotides in length and at least 15 nucleotides in length. Generally, the IL6 dsRNA is 19 to 24, e.g., 19 to 21 nucleotides in length. In some embodiments, the dsRNA is from about 10 to about 15 nucleotides in length, and in other embodiments the dsRNA is from about 25 to about 30 nucleotides in length. In another embodiment, a first sequence of the IL6 dsRNA is selected from the group consisting of the sense sequences of Tables 5, 6, 7, and 8, a second sequence is selected from the group consisting of the antisense sequences of Tables 5, 6, 7, and 8.

In another aspect, the deltaEGFR dsRNA is administered to a patient, and then a non-dsRNA agent is administered to the patient (or vice versa). In one embodiment, the deltaEGFR dsRNA and the non-dsRNA therapeutic agent are administered at the same time. In another embodiment, the deltaEGFR dsRNA is administered with an IL6 dsRNA, such as for the treatment of cancer.

In certain embodiments, the patient has a cancer, e.g., a tumor, such as an astrocytic tumor, or a glioma.

In one aspect, the invention provides a method for inhibiting the expression of a deltaEGFR gene in a cell by performing the following steps:
(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is substantially complementary to at least a part of a mRNA encoding deltaEGFR, and where the region of complementarity is less than 30 nucleotides in length, generally 19-24 nucleotides in length, and where the dsRNA, upon contact with a cell expressing the deltaEGFR, inhibits expression of the deltaEGFR gene by at least 40%; and
(b) maintaining the cell produced in step (a) for a time sufficient to obtain degradation of the mRNA transcript of deltaEGFR gene, thereby inhibiting expression of the deltaEGFR gene in the cell.

In one embodiment, the dsRNA that inhibits expression of the deltaEGFR gene also inhibits expression of a wildtype EGFR gene in the cell. Typically, such a dsRNA can inhibit both deltaEGFR expression and wildtype EGFR expression, because the antisense strand has a region of complementarity that is substantially complementary to at least a part of an mRNA encoding deltaEGFR and at least part of an mRNA encoding wildtype EGFR.

In another embodiment, the method is for inhibiting gene expression in a tumor cell.

In another aspect, the invention provides methods for treating, preventing or managing pathological processes mediated by deltaEGFR expression, e.g., a cancer, such as a glioma, e.g., a glial tumor of the central nervous system, such as a grade I, II, III, or IV glioma. For example, a dsRNA targeting deltaEGFR is used to treat a grade III glioma, such as anaplastic astrocytoma, or a grade IV glioma, such as a glioblastoma multiforme. In other embodiments, a dsRNA targeting deltaEGFR is used to treat a carcinoma of the breast, ovary, cervix, kidney, or squamous cell. In one embodiment, the deltaEGFR dsRNA is administered with a second dsRNA, such as an IL6 dsRNA, for treatment of a disorder associated with deltaEGFR expression. The IL6 and deltaEGFR dsRNAs can be administered in combination or sequentially. In yet another embodiment, an IL6 dsRNA alone is administered to treat a disorder associated with deltaEGFR expression.

A method featured in the invention can include administering to a patient in need of such treatment, prevention or management a therapeutically or prophylactically effective amount of one or more of the dsRNAs featured in the invention, e.g., one or both of a dsRNA targeting deltaEGFR or IL6. In one embodiment the patient has cancer. In another embodiment, administration of the dsRNA targeting deltaEGFR and/or the dsRNA targeting IL6, alleviates or relieves the severity of at least one symptom of the deltaEGFR-mediated disorder in the patient.

In another aspect, the invention provides a vector for inhibiting the expression of a deltaEGFR gene in a cell. In one embodiment, the vector includes at least one regulatory sequence operably linked to a nucleotide sequence that encodes at least one strand of one of a dsRNA featured in the invention.

In another aspect, the invention provides a vector for inhibiting the expression of an IL6 gene in a cell. In one embodiment, the vector includes at least one regulatory sequence operably linked to a nucleotide sequence that encodes at least one strand of one of a dsRNA featured in the invention.

In yet another aspect, the invention provides a cell containing a vector for inhibiting the expression of a deltaEGFR gene in a cell. The vector includes a regulatory sequence operably linked to a nucleotide sequence that encodes at least one strand of one of the deltaEGFR dsRNA featured in the invention. In one embodiment, the cell also contains a vector for inhibiting expression of an IL6 gene in a cell. This vector also has a regulatory sequence operably linked to a nucleotide sequence that encodes at least one strand of an IL6 dsRNA featured in the invention.

In yet another aspect, the invention provides a composition containing a deltaEGFR dsRNA, in combination with a second dsRNA targeting a second gene involved in a pathological disease, and useful for treating the disease, e.g., cancer. In one embodiment, the second dsRNA is a dsRNA targeting IL6.

The details of one or more embodiments of the invention are set forth in the description below. Other features, objects, and advantages of the invention will be apparent from the description and the drawings, and from the claims.

BRIEF DESCRIPTION OF THE FIGURES

FIG. 2A is H&E staining of brain cryo-sections from nude mice injected intracranially with cells, and FIG. 2B shows H&E staining of brain cryo-sections of mice injected intracranially with cells either alone or mixed with deltaEGFR over-expressing astrocytes (upper panel). The lower panel shows the presence of wtEGFR astrocytes within the tumor by immunofluorescence (GFP IF).

FIG. 6B shows the activity of siRNAs specific for deltaEGFR (AD-13375) or wtEGFR (AD-13377) in U87-deltaEGFR cells or U87-wtEGFR cells, respectively. Luc and (−) indicate negative controls (cells transfected with an irrelevant gene siRNA (targeting luciferase) and untransfected cells, respectively).

FIGS. 7A and 7B are Western blots showing dose response activity of siRNA activity in U87-deltaEGFR cells (FIG. 7A) and in U87-wtEGFR cells (FIG. 7B). U87-deltaEGFR cells were transfected with siRNAs specific for deltaEGFR, and for both mutant and wildtype receptors. U87-wtEGFR cells were transfected with siRNAs specific for wtEGFR, and for both mutant and wildtype receptors. C1, C2, C3, C4, C5, and C6 indicate negative controls (untransfected cells).

In FIGS. 8A and 8C, U87-deltaEGFR cells were transfected with non-stabilized (FIG. 8A) or stabilized (FIG. 8C) siRNAs. In FIGS. 8B and 8D, U87-wtEGFR cells were transfected with unstabilized (FIG. 8B) or stabilized (FIG. 8D) siRNAs. Lysates were prepared and Western blots were performed at the indicated day post-transfection. Luc and (−) indicate negative controls (cells transfected with an irrelevant gene siRNA (targeting luciferase) and untransfected cells, respectively).

FIG. 11 is the mRNA sequence of IL-6 reported at GenBank Accession No. NM_000600.2 (record dated Jan. 4, 2009, GI No. 155369258; SEQ ID NO:274).

FIG. 12A demonstrates the effect of the siRNAs on their target cytokines. Specificity of the siRNAs for IL-6 was assessed by quantifying IL-8 levels (FIG. 12B). Values are mean±SE of 2 independent samples. ("Neg": siRNA targeting an irrelevant sequence).

FIGS. 21A and 21B represent the mRNA sequence of wtEGFR (SEQ ID NO:1) (GenBank Accession No. NM_005228; record dated Aug. 24, 2008, GI No. 41327737). The underlined nucleotides are deleted in deltaEGFR mRNA sequence.

DETAILED DESCRIPTION OF THE INVENTION

Figure 1A:
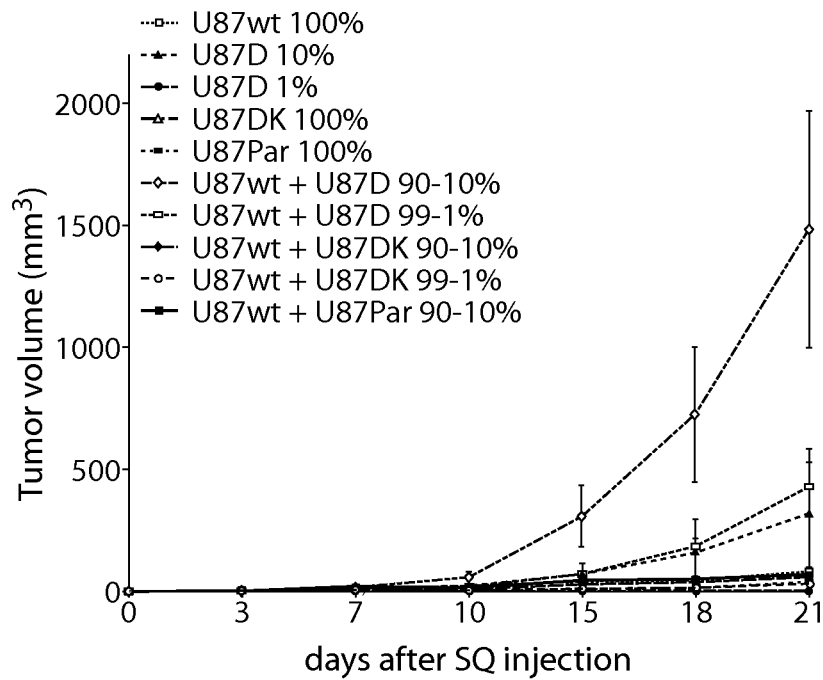
FIGS. 1A and 1B are graphs showing tumor growth kinetics (FIG. 1A) and tumor volume (FIG. 1B) following injection of cells subcutaneously into the right flank of 4 to 5 weeks-old female athymic nude mice.

The invention provides dsRNAs and methods of using the dsRNAs for inhibiting the expression of a deltaEGFR gene in a cell or a mammal where the dsRNA targets the deltaEGFR gene. In some embodiments, the dsRNAs featured in the invention target both a deltaEGFR gene and a wildtype EGFR (wtEGFR) gene. The invention also provides dsRNAs and methods of using the dsRNAs for inhibiting the expression of an IL6 gene in a cell or a mammal where the dsRNA targets the IL6 gene. The invention provides compositions and methods for treating pathological conditions and diseases, such as a cancer, in a mammal caused by the expression of the deltaEGFR or IL6 genes. dsRNA directs the sequence-specific degradation of mRNA through a process known as RNA interference (RNAi).

The dsRNAs of the compositions featured herein include an RNA strand (the antisense strand) having a region which is less than 30 nucleotides in length, generally 19-24 nucleotides in length, and is substantially complementary to at least part of an mRNA transcript of the deltaEGFR gene. The use of these dsRNAs enables the targeted degradation of mRNAs of genes that are implicated in replication or maintenance of cancer cells in mammals. Very low dosages of deltaEGFR or IL6 dsRNAs in particular can specifically and efficiently mediate RNAi, resulting in significant inhibition of expression of the deltaEGFR and IL6 genes. Using cell-based and animal assays, the present inventors have demonstrated that dsRNAs targeting deltaEGFR alone, or targeting both deltaEGFR and wtEGFR, can specifically and efficiently mediate RNAi, resulting in significant inhibition of expression of one or both of the deltaEGFR or EGFR genes. Thus, methods and compositions including these dsRNAs are useful for treating pathological processes that can be mediated by down regulating deltaEGFR and EGFR, such as in the treatment of cancer.

Using cell-based and animal assays, the present inventors have also demonstrated that dsRNAs targeting IL6 can also specifically and efficiently mediate RNAi, resulting in significant inhibition of expression of an IL6 gene. Thus, methods and compositions including these dsRNAs are useful for treating pathological processes that can be mediated by down regulating IL6, such as in the treatment of cancer.

The methods and compositions containing the deltaEGFR or IL6 dsRNA featured in the invention are useful for treating pathological processes mediated by deltaEGFR or IL6 expression, e.g., cancer, such as glioma.

The following detailed description discloses how to make and use the compositions containing dsRNAs to inhibit the expression of the deltaEGFR or IL6 genes, as well as compositions and methods for treating diseases and disorders caused by the expression of these genes, such as leukemia. The pharmaceutical compositions featured in the invention include a dsRNA having an antisense strand comprising a region of complementarity which is less than 30 nucleotides in length, generally 19-24 nucleotides in length, and is substantially complementary to at least part of an RNA transcript of the deltaEGFR or IL6 gene, together with a pharmaceutically acceptable carrier. The compositions featured in the invention also include a dsRNA having an antisense strand having a region of complementarity which is less than 30 nucleotides in length, generally 19-24 nucleotides in length, and which is substantially complementary to at least part of an RNA transcript of the deltaEGFR or IL6 gene.

Accordingly, in some aspects, pharmaceutical compositions containing the deltaEGFR dsRNA and a pharmaceutically acceptable carrier, methods of using the compositions to inhibit expression of the deltaEGFR gene, and methods of using the pharmaceutical compositions to treat diseases caused by expression of the deltaEGFR gene are featured in the invention.

In other aspects, pharmaceutical compositions containing the IL6 dsRNA and a pharmaceutically acceptable carrier, methods of using the compositions to inhibit expression of an IL6 gene, and methods of using the pharmaceutical compositions to treat diseases caused by expression of the IL6 gene are featured in the invention.

I. DEFINITIONS

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, thymidine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

As used herein, "deltaEGFR" refers to an in-frame deletion of exons 2-7 from the EGFR gene. deltaEGFR is also known as "de 2-7 EGFR" (Nishikawa et al. "A mutant epidermal growth factor receptor common in human glioma confers enhanced tumorigenicity" Proc. Natl. Acad. Sci. USA 91:7727-7731, 1994), "EGFR-de2-7", "EGFR*", "ΔEGFR", and "EGFRvIII." The sequence of deltaEGFR is equivalent to the sequence shown at FIGS. 21A and 21B carrying a deletion of nucleotides 335 through 1135.

As used herein, "wild-type EGFR" ("wtEGFR") refers to a non-mutant EGFR gene (e.g., an endogenous EGFR gene) in a cell, such as in a non-transformed, or non-cancerous cell in a human. EGFR is also known as EC2.7.10.1 (Epidermal Growth Factor Receptor Precursor), ERBB (Receptor Protein Tyrosine Kinase ErbB1), ERBB1, HER1, PIG61 (cell proliferation-inducing protein 61), mENA, avian erythroblastic leukemia viral (v-erb-b) oncogene homolog, and cell growth inhibiting protein 40. The sequence of four alternative wild-type EGFR mRNA transcripts can be found at Genbank Accession Numbers NM_005228.3 (record dated Aug. 24, 2008, GI No. 41327737; see FIGS. 21A and 21B), NM_201282.1 (record dated Aug. 24, 2008, GI No. 41327731), NM_201283.1 (record dated Aug. 24, 2008, GI No. 41327733), and NM_201284.1 (record dated Aug. 24, 2008, GI No. 41327735).

As used herein "Interleukin-6" ("IL-6") refers to an IL-6 gene (e.g., an endogenous IL-6 gene) in a cell, such as in a non-transformed, or non-cancerous cell in a human.

IL-6 is also known as Interleukin 6; IFNB2 (Interferon beta 2, or interferon, beta 2); BSF-2 (B-cell stimulatory factor 2); BSF2; CDF (CTL differentiation factor); HGF (hybridoma growth factor); HSF. The mRNA sequence of IL-6 is at GenBank Accession No. NM_000600.2 (FIG. 11) (record dated Jan. 4, 2009, GI No. 155369258).

As used herein, "target sequence" of a dsRNA refers to a contiguous portion of the nucleotide sequence of an mRNA molecule formed during the transcription of the target gene, e.g., a deltaEGFR gene or an IL-6 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, insofar as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of an mRNA of interest (e.g., encoding deltaEGFR or IL6). For example, a polynucleotide is complementary to at least a part of a deltaEGFR mRNA if the sequence is substantially complementary to a non-interrupted portion of an mRNA encoding deltaEGFR. Similarly, a polynucleotide is complementary to at least a part of a wtEGFR mRNA if the sequence is substantially complementary to a non-interrupted portion of an mRNA encoding wtEGFR.

The term "double-stranded RNA" or "dsRNA," as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop." Where the two strands are connected covalently by means other than an uninterrupted chain of nucleotides between the 3'-end of one strand and the 5' end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The term "identity" is the relationship between two or more polynucleotide sequences, as determined by comparing the sequences. Identity also means the degree of sequence relatedness between polynucleotide sequences, as determined by the match between strings of such sequences. While there exist a number of methods to measure identity between two polynucleotide sequences, the term is well known to skilled artisans (see, e.g., Sequence Analysis in Molecular Biology, von Heinje, G., Academic Press (1987); and Sequence Analysis Primer, Gribskov., M. and Devereux, J., eds., M. Stockton Press, New York (1991)). "Substantially identical," as used herein, means there is a very high degree of homology (e.g., 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. The dsRNA is typically 100% complementary to the target RNA, but in some embodiments, the dsRNA may contain single or multiple base-pair random mismatches between the RNA and the target gene.

As used herein, the term "SNALP" refers to a stable nucleic acid-lipid particle. A SNALP represents a vesicle of lipids coating a reduced aqueous interior comprising a nucleic acid such as an iRNA agent or a plasmid from which an iRNA agent is transcribed. SNALPs are described, e.g., in U.S. Patent Application Publication Nos. 20060240093, 20070135372, and U.S. Ser. No. 61/045,228 filed Apr. 15, 2008. These applications are hereby incorporated by reference.

"Introducing into a cell," when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell," wherein the cell is part of a living organism. In such instance, introduction into the cell will include the delivery to the organism. For example, for in vivo delivery, dsRNA can be injected into a tissue site or administered systemically. In vivo delivery can also be by a beta-glucan delivery system, such as those described in U.S. Pat. Nos. 5,032,401 and 5,607,677, and U.S. Publication No. 2005/0281781. U.S. Pat. Nos. 5,032,401 and 5,607,677, and U.S. Publication No. 2005/0281781 are hereby incorporated by reference in their entirety. In vitro introduction into a cell includes methods known in the art such as electroporation and lipofection.

The terms "silence," "inhibit the expression of," "down-regulate the expression of," "suppress the expression of," and the like, insofar as they refer to a deltaEGFR or IL6 gene, refer to the at least partial suppression of expression of the deltaE-GFR or IL6 gene, as manifested by a reduction of the amount of deltaEGFR or IL6 mRNA which may be isolated or detected from a first cell or group of cells in which the deltaEGFR or IL6 gene is transcribed and which has or have been treated such that the expression of the deltaEGFR or IL6 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to gene expression, e.g., the amount of protein encoded by the deltaEGFR or IL6 gene which is secreted by a cell, or the number of cells displaying a certain phenotype, e.g., apoptosis. In principle, gene silencing may be determined in any cell expressing the target gene, either constitutively or by genomic engineering, and by any appropriate assay. However, when a reference is needed in order to determine whether a given dsRNA inhibits the expression of a deltaE-GFR gene or an IL6 gene by a certain degree and therefore is encompassed by the instant invention, the assays provided in the Examples below shall serve as such reference. For example, deltaEGFR gene silencing may be determined in U87-deltaEGFR (Nishikawa et al., *PNAS* 91:7727-7731, 1994) or U87-wtEGFR (Nagana et al., *Cancer Research* 56:5079-5086, 1996) cells.

In some embodiments, expression of the deltaEGFR gene or IL6 gene is suppressed by at least about 20%, 25%, 30%, 35%, 40%, 45%, or 50% by administration of a double-stranded oligonucleotide featured in the invention. In some embodiments, the deltaEGFR or IL6 gene is suppressed by at least about 60%, 70%, or 80% by administration of the double-stranded oligonucleotide featured in the invention. In some embodiments, the deltaEGFR gene is suppressed by at least about 85%, 90%, or 95% by administration of the double-stranded oligonucleotide featured in the invention. Table 4, for example, and FIGS. 7-9 indicate a range of inhibition of expression obtained in in vitro and ex vivo assays using various deltaEGFR dsRNA molecules at various concentrations.

As used herein in the context of deltaEGFR or IL6 expression, the terms "treat," "treatment," and the like, refer to relief from or alleviation of pathological processes mediated by deltaEGFR or IL6 gene expression. Insofar as they relate to any of the other conditions recited herein below (other than pathological processes mediated by deltaEGFR expression), the terms "treat," "treatment," and the like mean to relieve or alleviate at least one symptom associated with such condition, or to slow or reverse the progression of such condition, such as the slowing and progression of glioma.

As used herein, the phrases "therapeutically effective amount" and "prophylactically effective amount" refer to an amount that provides a therapeutic benefit in the treatment, prevention, or management of pathological processes mediated by deltaEGFR or IL6 expression or an overt symptom of pathological processes mediated by deltaEGFR or IL6 expression. The specific amount that is therapeutically effective can be readily determined by an ordinary medical practitioner, and may vary depending on factors known in the art, such as, for example, the type of pathological processes mediated by deltaEGFR or IL6 expression, the patient's history and age, the stage of pathological processes mediated by deltaEGFR or IL6 expression, and the administration of other anti-pathological processes mediated by deltaEGFR or IL6 expression agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. DOUBLE-STRANDED RIBONUCLEIC ACID (dsRNA)

In one embodiment, the invention provides double-stranded ribonucleic acid (dsRNA) molecule for inhibiting expression of a deltaEGFR gene in a cell or mammal, e.g., in a human having a cancer, such as a glioma, where the dsRNA includes an antisense strand having a region of complementarity which is complementary to at least a part of an mRNA formed in the expression of the deltaEGFR gene, and where the region of complementarity is less than 30 nucleotides in length, generally 19-24 nucleotides in length, and where said dsRNA, upon contact with a cell expressing said deltaEGFR gene, inhibits the expression of said deltaEGFR gene by at least 30% as assayed by, for example, a PCR or branched DNA (bDNA)-based method, or by a protein-based method, such as by Western blot. Expression of the deltaEGFR gene can be reduced by at least 30% when measured by an assay as described in the Examples below. The expression of wtEGFR may also be reduced by at least 30%, e.g., as assayed by a method described herein, and the level of reduced expression of deltaEGFR and wtEGFR may be different. The reduction in deltaEGFR or wtEGFR expression can also be assayed by measuring protein levels, such as by Western blot analysis.

In one embodiment, the invention provides a double-stranded ribonucleic acid (dsRNA) molecule for inhibiting expression of an IL6 gene in a cell or mammal, e.g., in a human having a cancer, such as a glioma, where the dsRNA includes an antisense strand having a region of complementarity which is complementary to at least a part of an mRNA formed in the expression of the IL6 gene, and where the region of complementarity is less than 30 nucleotides in length, generally 19-24 nucleotides in length, and where the dsRNA, upon contact with a cell expressing the IL6 gene, inhibits the expression of the gene by at least 30% as assayed by, for example, a PCR or branched DNA (bDNA)-based method, or by a protein-based method, such as by Western blot.

A dsRNA featured in the invention, e.g., a dsRNA targeting deltaEGFR or IL6 mRNA, includes two RNA strands that are sufficiently complementary to hybridize to form a duplex structure. One strand of the dsRNA (the antisense strand) includes a region of complementarity that is substantially complementary, and generally fully complementary, to a target sequence, derived from the sequence of an mRNA formed during the expression of the target gene, the other strand (the sense strand) includes a region that is complementary to the antisense strand, such that the two strands hybridize and form a duplex structure when combined under suitable conditions. Optionally, the region of the antisense strand that is substantially complementary to a sequence of a deltaEGFR mRNA is also substantially complementary to a wtEGFR mRNA.

Generally, the duplex structure of a dsRNA featured herein is between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. In some embodiments, the dsRNA is between 10 and 15 nucleotides in length, and in other embodiments, the dsRNA is between 25 and 30 nucleotides in length. The dsRNA featured in the invention may further include one or more single-stranded nucleotide overhangs. The dsRNA can be synthesized by standard methods known in the art as further discussed below, e.g., by use of an automated DNA synthesizer, such as are commercially available from, for example, Biosearch, Applied Biosystems, Inc. In one embodiment, the deltaEGFR gene is a human deltaEGFR gene, and the wtEGFR gene is a human wtEGFR gene. In specific embodiments, the first sequence is a sense strand of the dsRNA that includes a sense sequence from Tables 2 or 3, and the second sequence is an antisense strand that includes an antisense sequence from Tables 2 or 3. Alternative antisense agents that target elsewhere in the target sequence provided in Tables 2 or 3 can readily be determined using the target sequence and the flanking deltaEGFR sequence.

The dsRNA targeting deltaEGFR will include at least two nucleotide sequences selected from the groups of sequences provided in Tables 2 or 3. One of the two sequences is complementary to the other of the two sequences, with one of the sequences being substantially complementary to a sequence of an mRNA generated in the expression of the deltaEGFR gene. As such, the dsRNA will include two oligonucleotides, where one oligonucleotide is described as the sense strand in Tables 2 or 3 and the second oligonucleotide is described as the antisense strand in Tables 2 or 3.

In some embodiments, the dsRNA will target an IL-6 gene, e.g., a human IL-6 gene. In certain embodiments, the first sequence of the dsRNA is a sense strand that includes a sense sequence from Tables 5-8, and the second sequence is an antisense strand that includes an antisense sequence from Tables 5-8. Alternative antisense agents that target elsewhere in the target sequence provided in Tables 5-8 can readily be determined using the target sequence and the flanking IL-6 sequence.

A dsRNA targeting IL-6 will include at least two nucleotide sequences selected from the groups of sequences provided in Tables 5-8. One of the two sequences is complementary to the other of the two sequences, with one of the sequences being substantially complementary to a sequence of an mRNA generated in the expression of the IL-6 gene. As such, the dsRNA will include two oligonucleotides, where one oligonucleotide is described as the sense strand in Tables 6-10 and the second oligonucleotide is described as the antisense strand in Tables 6-10.

In certain embodiments, the IL-6 dsRNA does not have a sense or antisense strand consisting of the sequences shown in Tables 6A or 6B of WO 2007/064846. In other embodiments, the dsRNA does not consist of the sequence of SEQ ID NO:1 of US2008/0234218, and its complementary sequence of SEQ NO:2; the sequence of SEQ ID NO:3 of US2008/0234218, and its complementary sequence of SEQ NO:4; or the sequence of SEQ ID NO:5 of US2008/0234218, and its complementary sequence of SEQ NO:6.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 2 and 3, and 5-8, the dsRNAs featured in the invention can include at least one strand of a length of minimally 21 nt. It can be reasonably expected that shorter dsRNAs having one of the sequences of Tables 2 or 3, or 5-8 minus only a few nucleotides on one or both ends may be similarly effective as compared to the dsRNAs described above. Hence, dsRNAs having a partial sequence of at least 15, 16, 17, 18, 19, 20, or more contiguous nucleotides from one of the sequences of Tables 2, 3 and 5-8, and differing in their ability to inhibit the expression of the respective target genes, e.g., as measured by a FACS assay as described herein below by not more than 5, 10, 15, 20, 25, or 30% inhibition from a dsRNA comprising the full sequence, are contemplated by the invention. Further, dsRNAs that cleave within the desired target sequence can readily be made using the corresponding deltaEGFR or IL6 antisense sequence and a complementary sense sequence.

In addition, the dsRNAs provided in Tables 2 and 3 identify a site in a deltaEGFR mRNA and the wtEGFR sequence that is susceptible to RNAi based cleavage, and the dsRNAs provided in Tables 5-8 identify a site in an IL6 mRNA susceptible to RNAi based cleavage As such, the present invention further provides dsRNAs that target within the sequence targeted by one of the other agents featured in the invention. As used herein, a second dsRNA is said to target within the sequence of a first dsRNA if the second dsRNA cleaves the message anywhere within the mRNA that is complementary to the antisense strand of the first dsRNA. Such a second dsRNA will generally consist of at least 15 contiguous nucleotides from one of the sequences provided in Tables 2, 3 or 5-8, coupled to an additional nucleotide sequence taken from the region contiguous to the selected sequence in the target gene, e.g., the deltaEGFR gene, the wtEGFR gene, or the IL6 gene. For example, the last 15 nucleotides of SEQ ID NO:2 combined with the next six nucleotides from the target deltaEGFR gene produces a single strand agent of 21 nucleotides that is based on one of the sequences provided in Tables 2 and 3.

The dsRNA featured in the invention can contain one or more mismatches to the target sequence. In one embodiment, the dsRNA contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the deltaEGFR gene, the dsRNA generally does not contain any mismatch within the central 13 nucleotides. The methods described within the invention can be used to determine whether a dsRNA containing a mismatch to a target sequence is effective in inhibiting the expression of the target gene, e.g., a deltaEGFR gene or an IL6 gene. Consideration of the efficacy of dsRNAs with mismatches in inhibiting expression of the target gene is important, especially if the particular region of complementarity in the target gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. In one embodiment, the antisense strand of the dsRNA has a 1-10 nucleotide overhang at the 3'-end and/or the 5' end. In another embodiment, the sense strand of the dsRNA has a 1-10 nucleotide overhang at the 3' end and/or the 5' end. In another embodiment, one or more of the nucleotides in the overhang is replaced with a nucleoside thiophosphate.

In yet another embodiment, the dsRNA is chemically modified to enhance stability. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Specific examples of dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is incorporated herein by reference Modified dsRNA backbones that do not include a phosphorus atom have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is incorporated herein by reference.

In other suitable dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, a dsRNA mimetic that has been shown to have excellent hybridization properties, is referred to as a peptide nucleic acid (PNA). In PNA compounds, the sugar backbone of a dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is incorporated herein by reference. Further teaching of PNA compounds can be found in Nielsen et al., Science, 1991, 254, 1497-1500.

Most embodiments featured in the invention include dsRNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the dsRNAs featured herein have morpholino backbone structures of the above-referenced U.S. Pat. No. 5,034,506.

Modified dsRNAs may also contain one or more substituted sugar moieties. The dsRNAs featured herein can have one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a dsRNA, or a group for improving the pharmacodynamic properties of a dsRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$, also described in examples hereinbelow.

Other modifications include 2'-methoxy (2'-O$CH_3$), 2'-aminopropoxy (2'-O$CH_2CH_2CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is incorporated herein by reference in its entirety.

DsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., DsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091;

5,614,617; and 5,681,941, each of which is herein incorporated by reference, and U.S. Pat. No. 5,750,692, also incorporated herein by reference.

Another modification of the dsRNAs featured in the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-5-tritylthiol (Manoharan et al., Ann N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim Biophys. Acta, 1995, 1264:229-237), or an octadecylamine or hexylamino-carbonyloxycholesterol moiety (Crooke et al., J. Pharmacol. Exp. Ther., 1996, 277:923-937).

Representative U.S. patents that teach the preparation of such dsRNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within a dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of a dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim Biophys. Acta, 1995, 1264:229), or an octadecylamine or hexylamino-carbonyloxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

Vector Encoded dsRNAs

In another aspect, dsRNA molecules featured in the invention, e.g., deltaEGFR and IL6 dsRNAs, are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In one embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., *Curr.*

Topics Micro. Immunol. (1992) 158:97-129)); adenovirus (see, for example, Berkner, et al., BioTechniques (1998) 6:616), Rosenfeld et al. (1991, Science 252:431-434), and Rosenfeld et al. (1992), Cell 68:143-155)); or alphavirus as well as others known in the art. Retroviruses have been used to introduce a variety of genes into many different cell types, including epithelial cells, in vitro and/or in vivo (see, e.g., Eglitis, et al., Science (1985) 230:1395-1398; Danos and Mulligan, Proc. Natl Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Nad. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the dsRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors featured in the invention can be pseudotyped with surface proteins from vesicular stomatitis virus (VSV), rabies, Ebola, Mokola, and the like. AAV vectors featured in the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Viral vectors can be derived from AV and AAV. In one embodiment, the dsRNA featured in the invention is expressed as two separate, complementary single-stranded RNA molecules from a recombinant AAV vector having, for example, either the U6 or H1 RNA promoters, or the cytomegalovirus (CMV) promoter.

A suitable AV vector for expressing the dsRNA featured in the invention, a method for constructing the recombinant AV vector, and a method for delivering the vector into target cells, are described in Xia H et al. (2002), Nat. Biotech. 20: 1006-1010.

Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

The promoter driving dsRNA expression in either a DNA plasmid or viral vector featured in the invention may be a eukaryotic RNA polymerase I (e.g., ribosomal RNA promoter), RNA polymerase II (e.g., CMV early promoter or actin promoter or U1 snRNA promoter) or generally RNA polymerase III promoter (e.g., U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g., Oligofectamine) or non-cationic lipid-based carriers (e.g., Transit-TKO™). Multiple lipid transfections for dsRNA-mediated knockdowns targeting different regions of a single target gene or multiple target genes over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

The deltaEGFR- and IL6-specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. PHARMACEUTICAL COMPOSITIONS CONTAINING dsRNA

In one embodiment, the invention provides pharmaceutical compositions containing a dsRNA, as described herein, and a pharmaceutically acceptable carrier. The pharmaceutical composition containing the dsRNA is useful for treating a disease or disorder associated with the expression or activity of the deltaEGFR gene and/or the IL6 gene, such as pathological processes mediated by deltaEGFR or IL6 expression. Such pharmaceutical compositions are formulated based on the mode of delivery. One example is a composition formulated for direct delivery into the brain parenchyma, e.g., by infusion into the brain, such as by continuous pump infusion. Another example is a composition formulated for intraventricular or intrathecal delivery into the cerebrospinal fluid, e.g., by bolus or continuous pump infusion. Another example is a compositions formulated for systemic administration via parenteral delivery, e.g., by intravenous (IV) delivery.

The pharmaceutical compositions featured herein are administered in dosages sufficient to inhibit expression of the target gene, e.g, the deltaEGFR or IL6 gene. In general, a suitable dose of dsRNA will be in the range of 0.01 to 200.0 milligrams per kilogram body weight of the recipient per day, generally in the range of 0.02 to 50 mg per kilogram body weight per day. For example, the dsRNA can be administered at 0.01 mg/kg, 0.05 mg/kg, 0.1 mg/kg, 0.5 mg/kg, 1 mg/kg, 2 mg/kg, 3 mg/kg, 10 mg/kg, 20 mg/kg, 30 mg/kg, 40 mg/kg, or 50 mg/kg per single dose. The pharmaceutical composition may be administered once daily, or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for delivery of agents at a particular site, such as could be used with the agents featured in the invention. In this embodiment, the dosage unit contains a corresponding multiple of the daily dose.

The effect of a single dose of dsRNA on target RNA levels, e.g., deltaEGFR levels (or both deltaEGFR and wtEGFR levels) or IL6 levels, is long lasting, such that subsequent doses are administered at not more than 3, 4, or 5 day intervals, or at not more than 1, 2, 3, or 4 week intervals.

The present invention includes pharmaceutical compositions that can be delivered by injection directly into the brain. The injection can be by stereotactic injection into the brain tumor directly, or into a particular region of the brain (e.g., into white matter, such as the corona radiata, or the substantia nigra, cortex, hippocampus, striatum, or globus pallidus), or the dsRNA can be delivered into multiple regions of the central nervous system (e.g., into multiple regions of the brain, and/or into the spinal cord). The dsRNA can also be delivered into diffuse regions of the brain (e.g., diffuse delivery to the cortex of the brain).

In one embodiment, a dsRNA targeting deltaEGFR or IL-6 can be delivered by way of a cannula or other delivery device having one end implanted in a tissue, e.g., the brain, e.g., the white matter, such as the corona radiata, or the substantia nigra, cortex, hippocampus, striatum, corpus callosum or globus pallidus of the brain. In one embodiment, the cannula or other delivery device has one end implanted into a tumor in the brain. The cannula can be connected to a reservoir of the dsRNA composition. The flow or delivery can be mediated by a pump. In one embodiment, a pump and reservoir are implanted in an area distant from the tissue, e.g., in the abdomen, and delivery is effected by a conduit leading from the pump or reservoir to the site of release. Infusion of the dsRNA composition into the brain can be over several hours or for several days, e.g., for 1, 2, 3, 5, or 7 days or more. Devices for delivery to the brain are described, for example, in U.S. Pat. Nos. 6,093,180, and 5,814,014. In another embodiment, the pump is externalized (not implanted). Infusion of the dsRNA composition into the brain can be over several hours or for several days up to approximately 7 days, e.g., for 1, 2, 3, 5, or 7 days.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by deltaEGFR or IL6 expression. Such models are used for in vivo testing of dsRNA, as well as for determining a therapeutically effective dose.

The present invention also includes pharmaceutical compositions and formulations which include the dsRNA compounds featured in the invention. The pharmaceutical compositions may be administered in a number of ways depending upon whether local or systemic treatment is desired and upon the area to be treated. Administration may be topical (e.g., by transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the dsRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). DsRNAs featured in the invention may be encapsulated within liposomes or may form complexes thereto, in particular to cationic liposomes. Alternatively, dsRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference in its entirety.

In one embodiment, a deltaEGFR or an IL-6 dsRNA featured in the invention is fully encapsulated in the lipid formulation (e.g., to form a SPLP, pSPLP, SNALP, or other nucleic acid-lipid particle). As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids when present in the nucleic acid-lipid particles are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA), or a mixture thereof. The cationic lipid may comprise from about 20 mol % to about 50 mol % or about 40 mol % of the total lipid present in the particle.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($Ci_8$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (Formula 1), Cholesterol (Sigma-Aldrich), and PEG-Ceramide C16 (Avanti Polar Lipids) can be used to prepare lipid-siRNA nanoparticles (i.e., LNP01 particles). Stock solutions of each in ethanol can be prepared as follows: ND98, 133 mg/mL; Cholesterol, 25 mg/mL, PEG-Ceramide C16, 100 mg/mL. The ND98, Cholesterol, and PEG-Ceramide C16 stock solutions can then be combined in a, e.g., 42:48:10 molar ratio. The combined lipid solution can be mixed with aqueous siRNA (e.g., in sodium acetate pH 5) such that the final ethanol concentration is about 35-45% and the final sodium acetate concentration is about 100-300 mM. Lipid-siRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

factants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl Formula 1

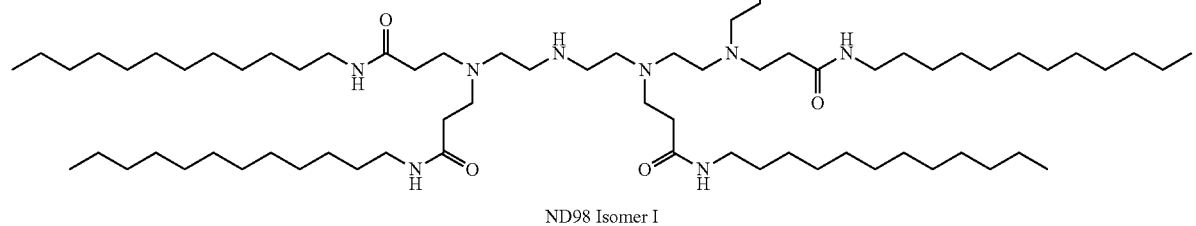

ND98 Isomer I

LNP01 formulations are described, e.g., in International Application Publication No. WO 2008/042973, which is hereby incorporated by reference.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total siRNA concentration in the formulation, as well as the entrapped fraction, is estimated using a dye exclusion assay. A sample of the formulated siRNA can be incubated with an RNA-binding dye, such as Ribogreen (Molecular Probes) in the presence or absence of a formulation disrupting surfactant, e.g., 0.5% Triton-X100. The total siRNA in the formulation can be determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable sur- 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference in their entirety.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions featured in the invention include, but are not limited to, solutions, emulsions, and liposome-containing formulations. These compositions may be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions may be formulated into any of many possible dosage forms such as, but not limited to, tablets, capsules, gel capsules, liquid syrups, soft gels, suppositories, and enemas. The compositions may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Emulsions

The compositions may be prepared and formulated as emulsions. Emulsions are typically heterogenous systems of one liquid dispersed in another in the form of droplets usually exceeding 0.1 .mu.m in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and antioxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271). The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations will facilitate the increased systemic absorption of dsRNAs and nucleic acids from the gastrointestinal tract, as well as improve the local cellular uptake of dsRNAs and nucleic acids.

Microemulsions may also contain additional components and additives such as sorbitan monostearate (Grill 3), Labrasol, and penetration enhancers to improve the properties of the formulation and to enhance the absorption of the dsRNAs and nucleic acids featured herein. Penetration enhancers used in the microemulsions may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_M1$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann N.Y. Acad. Sci., 1987, 507, 64) reported the ability of monosialoganglioside $G_M1$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_M1$ or a galactocerebroside sulfate ester. U.S. Pat. No. 5,543,152 (Webb et al.) discloses liposomes comprising sphingomyelin. Liposomes comprising 1,2-sn-dimyristoylphosphat-idylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}15G$, that contains a PEG moiety. Ilium et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the present invention employs various penetration enhancers to effect the efficient delivery of nucleic acids, particularly dsRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants:

In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty Acids:

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carryier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile Salts:

The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents:

Chelating agents, as used in connection with the present invention, can be defined as compounds that remove metallic ions from solution by forming complexes therewith, with the result that absorption of dsRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-Chelating Non-Surfactants:

As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions featured in the invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4' isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipient suitable for non-parenteral administration, which do not deleteriously react with nucleic acids, can also be used to formulate the compositions. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions featured in the invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions, such as dyes, flavoring agents, preservatives, antioxidants, opacifiers, thickening agents and stabilizers. However, such materials, when added, should not unduly interfere with the biological activities of the components of the compositions. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

In some embodiments, pharmaceutical compositions featured in the invention include (a) one or more dsRNA compounds and (b) one or more other chemotherapeutic agents which function by a non-RNAi mechanism. Examples of such chemotherapeutic agents include but are not limited to temozolomide, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the dsRNAs featured in the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions featured in the invention. See, generally, The Merck Manual of Diagnosis and Therapy, 15th Ed., Berkow et al., eds., 1987, Rahway, N.J., pages 2499-2506 and 46-49, respectively). Other non-RNAi chemotherapeutic agents are also within the scope of this invention. Two or more combined compounds may be used together or sequentially.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are generally preferred.

The data obtained from cell culture assays and animal studies can be used in formulation a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration, as discussed above, the dsRNAs featured in the invention can be administered in combination with other known agents effective in treatment of pathological processes mediated by deltaEGFR or IL6 expression. In any event, the administering physician can adjust the amount and timing of dsRNA administration on the basis of results observed using standard measures of efficacy known in the art or described herein.

Methods for Treating Diseases Caused by Expression of deltaEGFR or IL6 Genes

The invention relates in particular to the use of a dsRNA targeting deltaEGFR or IL6 and compositions containing at least one such dsRNA, for the treatment of a deltaEGFR-mediated disorder or disease. For example, a dsRNA targeting a deltaEGFR gene can be useful for the treatment of a proliferative disorder, such as cancer, such as glioma, e.g., a glial tumor of the central nervous system, such as a grade I, II, III, or IV glioma. For example, a composition containing a dsRNA targeting deltaEGFR can be used to treat a grade III glioma, such as anaplastic astrocytoma, or a grade IV glioma, such as a glioblastoma multiforme. The glioma can be an ependymoma, astrocytoma, oligodendroglioma, or a mixed glioma, such as an oligoastrocytoma. A composition containing a dsRNA targeting a mutant EGFR, e.g., deltaEGFR or an IL6, is used to treat a carcinoma of the breast, ovary, cervix, kidney, or a squamous cell. The dsRNA targeting deltaEGFR can also target wtEGFR.

A composition containing a dsRNA targeting a mutant EGFR, e.g., a deltaEGFR or an IL6, may also be used to treat other tumors and cancers, such as breast cancer, lung cancer, head and neck cancer, brain cancer, abdominal cancer, colon cancer, colorectal cancer, esophagus cancer, gastrointestinal cancer, tongue cancer, neuroblastoma, osteosarcoma, ovarian cancer, pancreatic cancer, prostate cancer, cervical cancer (e.g., squamous carcinoma of the cervix), lymphoid tumor, retinoblastoma, Wilm's tumor, multiple myeloma and for the treatment of skin cancer, like melanoma, for the treatment of lymphomas and blood cancer. The compositions featured herein can be used to treat a tumor of the brain or spine.

A dsRNA targeting deltaEGFR or IL6 may be used to treat a proliferative disorder or differentiative disorder. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including those of prostate, colon, lung, breast and liver origin. As used herein, the terms "cancer," "hyperproliferative," and "neoplastic" refer to cells having the capacity for autonomous growth, i.e., an abnormal state or condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoictic origin, e.g., arising from myeloid, lymphoid or erythroid lineages, or precursor cells thereof.

The invention further relates to the use of a dsRNA or a pharmaceutical composition thereof, e.g., for treating a cancer, in combination with other pharmaceuticals and/or other therapeutic methods, e.g., with known pharmaceuticals and/or known therapeutic methods, such as, for example, those which are currently employed for treating these disorders. In one example, administration of a dsRNA targeting deltaEGFR can be administered in combination with a chemotherapeutic agent, such as temozolomide, deoxycoformycin, cisplatin, cyclophosphamide, 5-fluorouracil, adriamycin, daunorubicin, tamoxifen aunorubicin, daunomycin, dactinomycin, doxorubicin, epirubicin, idarubicin, esorubicin, bleomycin, mafosfamide, ifosfamide, cytosine arabinoside, bischloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the dsRNAs featured in the invention, such chemotherapeutic agents may be used individually, sequentially (e.g., dsRNA for a period of time, followed by chemotherapy), or in combination with one or more other such agents (e.g., chemotherapy and dsRNA). Two or more combined compounds may be used together or sequentially.

In one embodiment, a deltaEGFR dsRNA is administered in combination with at least one additional therapeutic agent, such as a second dsRNA targeting a different nucleic acid, e.g., an IL6 dsRNA, for the treatment of a condition or a symptom of a condition, such as for the treatment of a cancer. In some embodiments, the second therapeutic agent is a chemotherapeutic agent.

The dsRNA and an additional therapeutic agent can be administered in the same combination, e.g., intracranially or parenterally, or the additional therapeutic agent can be administered as part of a separate composition, e.g., intracranially or parenterally, or by another method described herein.

Treatment with a dsRNA targeting deltaEGFR can also be performed in combination with radiation therapy, including external beam radiation, such as for treatment of tumors of the brain. A dsRNA featured herein may be administered before or after a surgical procedure to treat a cancer (e.g., to remove a tumor), such as resection of a brain tumor.

The invention also relates to the use of a dsRNA targeting IL6 and compositions containing at least one such dsRNA, for the treatment of a IL6 or a deltaEGFR-mediated disorder or disease. For example, an IL-6 dsRNA featured in the invention may be used to treat a hematological disorder, such as plasma cell dyscrasia, leukemia or lymphoma; proliferative glomerulonephritis; an inflammatory disease, such as rheumatoid arthritis, or an inflammatory bowel disease, such as Crohn's disease or ulcerative colitis; diabetes; septic shock; bacterial infections; viral infections, including HIV-1 infections; osteoporosis; autoimmune disorders, such as chronic immune deficiency syndrome or autoimmune deficiency syndrome (AIDS); neural disorders, such as multiple sclerosis, HTLV1-associated myelopathy or bacterial meningitis, systemic lupus erythematosus and vasculitis-associated central nervous system diseases; or other disorders of the central nervous system, including Alzheimer's disease, hypochondria, epilepsy, migraine, pain, Parkin's disease or schizophrenia.

An IL-6 dsRNA featured in the invention may also be used to prevent allograft rejection or xenograft rejection and ischemia/reperfusion injury in solid organ or tissue transplantation. For example, an IL-6 dsRNA can be administered to prevent rejection of a transplanted organ, such as a transplanted kidney, liver, lung, pancrease, heart, small bowel, cornea, epithelial cells, vascular endothelium, vascular smooth muscle cells, myocardium and passenger leukocytes resident in the organ at the time of transplantation.

Treatment with a dsRNA targeting IL-6 can be performed in combination with a second dsRNA also targeting IL-6, and which targets a different sequence than a first dsRNA targeting IL-6. A dsRNA targeting IL-6 can also be administered in combination with one or more dsRNAs targeting other cytokines, immunomodulatory or immunoeffector genes, such as the C3 (complement component 3) gene, ICAM1 (intercellular adhesion molecule 1), VCAM-1 (vascular cell adhesion molecule 1), IFN-gamma (interferon gamma), IL-1 (interleukin-1), IL-8 (interleukin-8), TNF-alpha (tumor necrosis factor-alpha), CD80, CD86, MHC-II (major histocombatibility complex-II), MHC-I (major histocombatibility complex-I), CD28, CTLA-4 (cytotoxic T-lymphocyte-associated protein 4) or PV-B19 (parvovirus B19). As stated above, the IL6 dsRNA can also be administered in combination with a dsRNA targeting deltaEGFR, and optionally, also targeting wtEGFR, such as for the treatment of a deltaEGFR mediated disease, such as a cancer.

Patients can be administered a therapeutic amount of dsRNA, such as 0.01 mg/kg, 0.02 mg/kg, 0.1 mg/kg, 0.5 mg/kg, 1.0 mg/kg, 1.5 mg/kg, 2.0 mg/kg, or 2.5 mg/kg dsRNA. The dsRNA can be administered by intracranial infusion over a period of time, such as over a 30 minute, 1 hour, 2 hour, 3 hour or 4 hour period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Intracranial infusion can be continuous. Administration of the dsRNA can reduce target RNA and protein levels, e.g., deltaEGFR or IL-6 levels, in the cerebrospinal fluid of the patient by at least 20%, 25%, 30%, 40%, 50%, 60%, 70%, 80% or 90% or more. Alternatively, the dsRNA can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the dsRNA can reduce deltaEGFR levels in the blood or urine of the patient by at least 20%, 25%, 30%, 40%, 50%, 60%, 70%, 80% or 90% or more.

Before administration of a full dose of the dsRNA, patients can be administered a smaller dose, such as 5% of the total dose, and monitored for adverse effects, such as an allergic reaction. Patients can be monitored for adverse effects depending on the formulation. For example, if the dsRNA is formulated in a lipid, the patient can be administered a smaller dose, and then monitored for elevated lipid levels or blood pressure. In another example, the patient can be monitored for unwanted immunostimulatory effects, such as increased cytokine (e.g., TNF-alpha or INF-alpha) levels.

Many EGFR- and IL6-associated diseases and disorders are hereditary. Therefore, a patient in need of a deltaEGFR dsRNA can be identified by taking a family history. A healthcare provider, such as a doctor, nurse, or family member, can take a family history before prescribing or administering a deltaEGFR dsRNA.

Owing to the inhibitory effects on deltaEGFR expression, and of the inhibitory effects of IL6 overexpression, a composition according to the invention or a pharmaceutical composition prepared therefrom can enhance the quality of life of a subject.

Methods for Inhibiting Expression of a deltaEGFR or IL6 Gene

In yet another aspect, the invention provides a method for inhibiting expression of a deltaEGFR gene in a mammal. The method includes administering a composition featured in the invention to the mammal such that expression of the target deltaEGFR gene and, optionally, a wtEGFR gene is decreased or silenced. In one aspect, the invention provides a method for inhibiting expression of an IL6 gene in a mammal. The method includes administering a composition featured in the invention to the mammal such that expression of the target IL6 gene is decreased or silenced.

When the organism to be treated is a mammal such as a human, the composition may be administered by any means known in the art including, but not limited to oral or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection. In other embodiments, the compositions are administered by intracranial infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the dsRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support is used for RNA synthesis. The modified solid support is prepared as follows:

Diethyl-2-azabutane-1,4-dicarboxylate AA

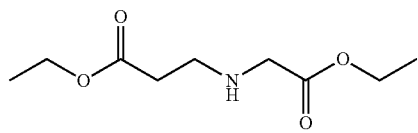

A 4.7 M aqueous solution of sodium hydroxide (50 mL) is added into a stirred, ice-cooled solution of ethyl glycinate hydrochloride (32.19 g, 0.23 mole) in water (50 mL). Then, ethyl acrylate (23.1 g, 0.23 mole) is added and the mixture is stirred at room temperature until completion of the reaction is ascertained by TLC. After 19 h the solution is partitioned with dichloromethane (3×100 mL). The organic layer is dried with anhydrous sodium sulfate, filtered and evaporated. The residue is distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

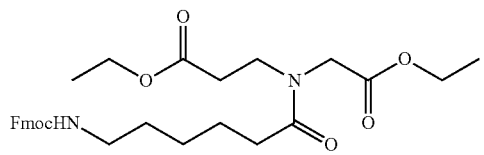

Fmoc-6-amino-hexanoic acid (9.12 g, 25.83 mmol) is dissolved in dichloromethane (50 mL) and cooled with ice. Diisopropylcarbodiimde (3.25 g, 3.99 mL, 25.83 mmol) is added to the solution at 0° C. It is then followed by the addition of Diethyl-azabutane-1,4-dicarboxylate (5 g, 24.6 mmol) and dimethylamino pyridine (0.305 g, 2.5 mmol). The solution is brought to room temperature and stirred further for 6 h. Completion of the reaction is ascertained by TLC. The reaction mixture is concentrated under vacuum and ethyl acetate is added to precipitate diisopropyl urea. The suspension is filtered. The filtrate is washed with 5% aqueous hydrochloric acid, 5% sodium bicarbonate and water. The combined organic layer is dried over sodium sulfate and concentrated to give the crude product which is purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

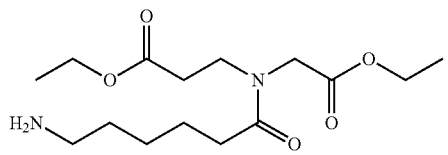

3-{Ethoxycarbonylmethyl-[6-(9H-fluoren-9-ylmethoxycarbonylamino)-hexanoyl]-amino}-propionic acid ethyl ester AB (11.5 g, 21.3 mmol) is dissolved in 20% piperidine in dimethylformamide at 0° C. The solution is continued stirring for 1 h. The reaction mixture is concentrated under vacuum, water is added to the residue, and the product is extracted with ethyl acetate. The crude product is purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

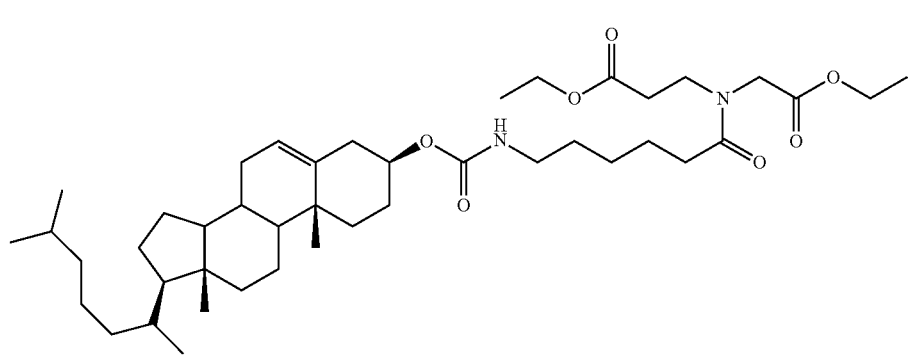

The hydrochloride salt of 3-[(6-Amino-hexanoyl)-ethoxy-carbonylmethyl-amino]-propionic acid ethyl ester AC (4.7 g, 14.8 mmol) is taken up in dichloromethane. The suspension is cooled to 0° C. on ice. To the suspension diisopropylethylamine (3.87 g, 5.2 mL, 30 mmol) is added. To the resulting solution cholesteryl chloroformate (6.675 g, 14.8 mmol) is added. The reaction mixture is stirred overnight. The reaction mixture is diluted with dichloromethane and ished with 10% hydrochloric acid. The product is purified by flash chromatography (10.3 g, 92%).

of phosphate buffer each, dried, and evaporated to dryness. The residue is dissolved in 60 mL of toluene, cooled to 0° C. and extracted with three 50 mL portions of cold pH 9.5 carbonate buffer. The aqueous extracts are adjusted to pH 3 with phosphoric acid, and extracted with five 40 mL portions of chloroform which are combined, dried and evaporated to dryness. The residue is purified by column chromatography using 25% ethylacetate/hexane to afford 1.9 g of b-ketoester (39%).

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

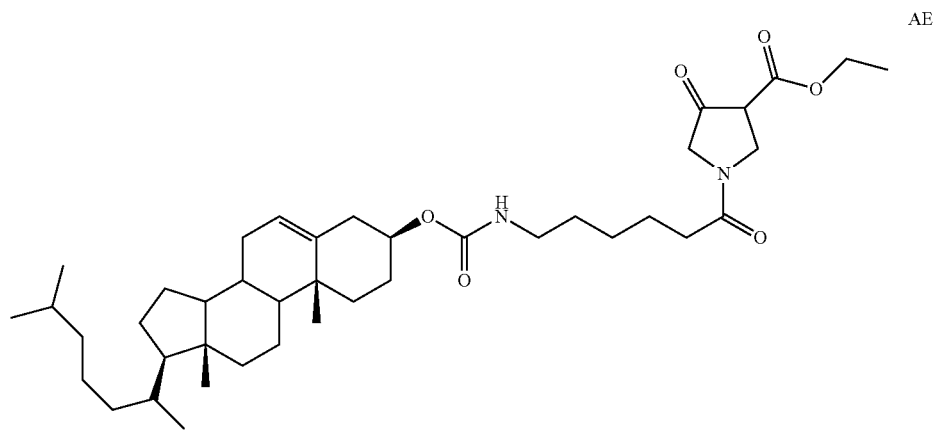 [SMILES: CCOC(=O)C1CN(C(=O)CCCCCNC(=O)O[C@H]2CC[C@@]3(C)C(=CCC4C3CC[C@@]3(C)C4CC[C@@H]3C(C)CCCC(C)C)C2)CC1=O]

Potassium t-butoxide (1.1 g, 9.8 mmol) is slurried in 30 mL of dry toluene. The mixture is cooled to 0° C. on ice and 5 g (6.6 mmol) of diester AD is added slowly with stirring within 20 mins. The temperature is kept below 5° C. during the addition. The stirring is continued for 30 mins at 0° C. and 1 mL of glacial acetic acid is added, immediately followed by 4 g of NaH$_2$PO$_4$.H$_2$O in 40 mL of water. The resultant mixture is extracted twice with 100 mL of dichloromethane each and the combined organic extracts are washed twice with 10 mL

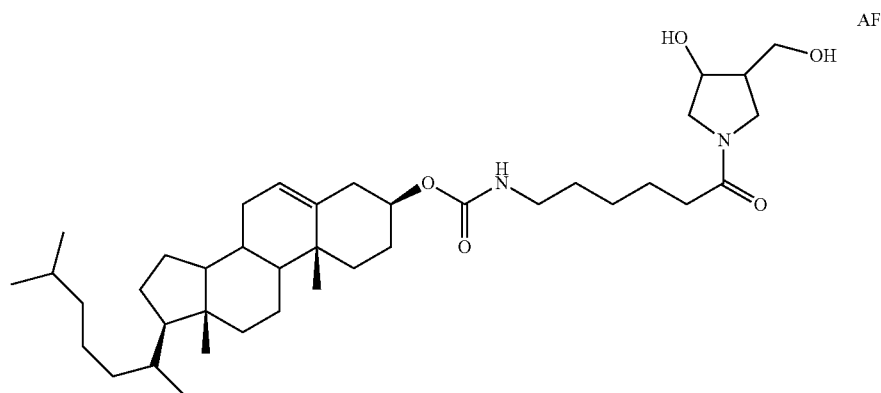 [SMILES: CC(C)CCCC(C)[C@H]1CCC2C3CC=C4C[C@@H](OC(=O)NCCCCCC(=O)N5CC(O)C(CO)C5)CC[C@]4(C)C3CC[C@@]21C]

Methanol (2 mL) is added dropwise over a period of 1 h to a refluxing mixture of b-ketoester AE (1.5 g, 2.2 mmol) and sodium borohydride (0.226 g, 6 mmol) in tetrahydrofuran (10 mL). Stirring is continued at reflux temperature for 1 h. After cooling to room temperature, 1 N HCl (12.5 mL) is added, the mixture is extracted with ethylacetate (3×40 mL). The combined ethylacetate layer is dried over anhydrous sodium sulfate and concentrated under vacuum to yield the product which is purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

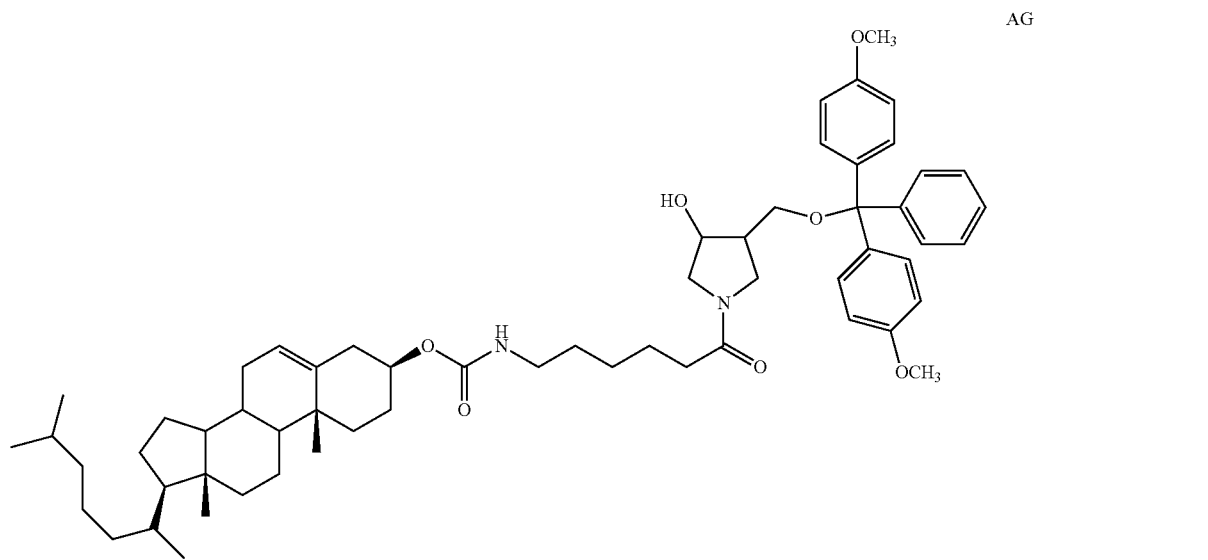 [SMILES: COc1ccc(C(OCC2CN(C(=O)CCCCCNC(=O)O[C@H]3CC[C@@]4(C)C(=CCC5C4CC[C@@]4(C)C5CC[C@@H]4C(C)CCCC(C)C)C3)CC2O)(c2ccccc2)c2ccc(OC)cc2)cc1]

Diol AF (1.25 gm 1.994 mmol) is dried by evaporating with pyridine (2×5 mL) in vacuo. Anhydrous pyridine (10 mL) and 4,4'-dimethoxytritylchloride (0.724 g, 2.13 mmol) are added with stirring. The reaction is carried out at room temperature overnight. The reaction is quenched by the addition of methanol. The reaction mixture is concentrated under vacuum and to the residue dichloromethane (50 mL) is added. The organic layer is washed with 1M aqueous sodium bicarbonate. The organic layer is dried over anhydrous sodium sulfate, filtered and concentrated. The residual pyridine is removed by evaporating with toluene. The crude product is purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

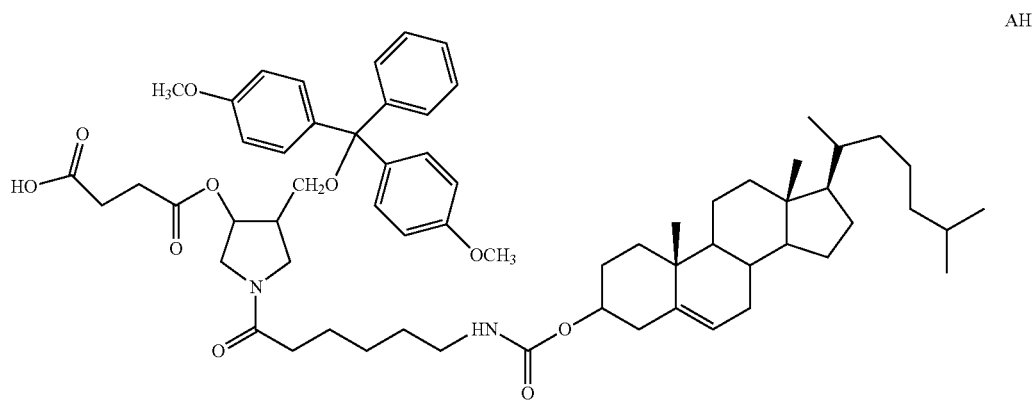

Compound AG (1.0 g, 1.05 mmol) is mixed with succinic anhydride (0.150 g, 1.5 mmol) and DMAP (0.073 g, 0.6 mmol) and dried in a vacuum at 40° C. overnight. The mixture is dissolved in anhydrous dichloroethane (3 mL), triethylamine (0.318 g, 0.440 mL, 3.15 mmol) is added and the solution is stirred at room temperature under argon atmosphere for 16 h. It is then diluted with dichloromethane (40 mL) and washed with ice cold aqueous citric acid (5 wt %, 30 mL) and water (2×20 mL). The organic phase is dried over anhydrous sodium sulfate and concentrated to dryness. The residue is used as such for the next step.

Cholesterol derivatised CPG AI

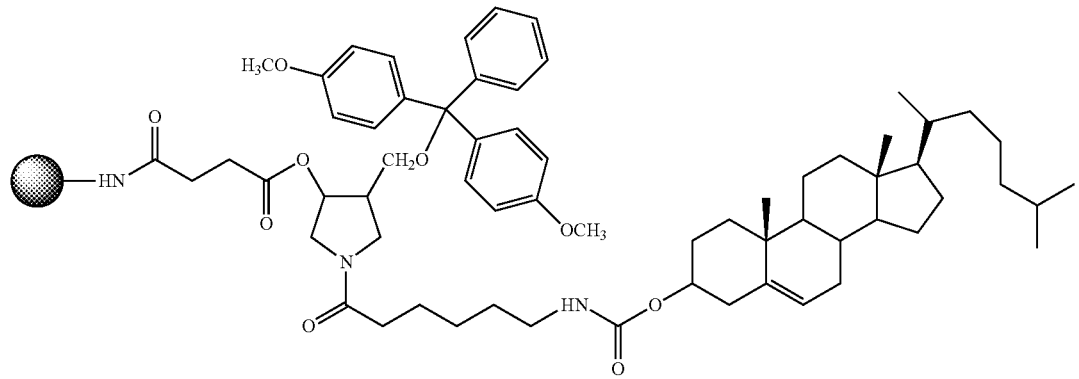

AI

Succinate AH (0.254 g, 0.242 mmol) is dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) are added successively. To the resulting solution triphenylphosphine (0.064 g, 0.242 mmol) in acetonitrile (0.6 ml) is added. The reaction mixture turned bright orange in color. The solution is agitated briefly using a wrist-action shaker (5 mins). Long chain alkyl amine-CPG (LCAA-CPG) (1.5 g, 61 mM) is added. The suspension is agitated for 2 h. The CPG is filtered through a sintered funnel and washed with acetonitrile, dichloromethane and ether successively. Unreacted amino groups are masked using acetic anhydride/pyridine. The achieved loading of the CPG is measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") is performed as described in WO 2004/065601, except that, for the cholesteryl derivative, the oxidation step is performed using the Beaucage reagent in order to introduce a phosphorothioate linkage at the 5'-end of the nucleic acid oligomer.

Nucleic acid sequences are represented below using standard nomenclature, and specifically the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | adenosine |
| C | cytidine |
| G | guanosine |
| T | thymidine |
| U | uridine |
| N | any nucleotide (G, A, C, or T) |

TABLE 1-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| a | 2'-O-methyladenosine |
| c | 2'-O-methylcytidine |
| g | 2'-O-methylguanosine |
| u | 2'-O-methyluridine |
| sT | phosphorothioate linkage |

Example 2

Figure 1B:
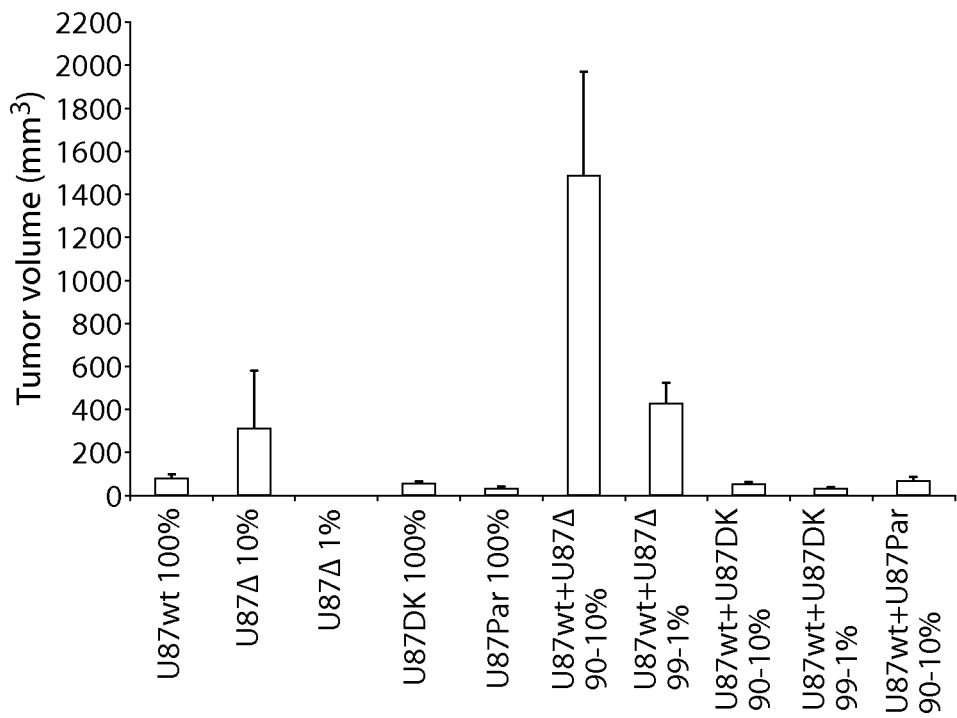

ΔEGFR Enhances Tumorigenicity of Wt EGFR Over-Expressing Cells After Subcutaneous Injection into Nude Mice U87MG (U87 Par) cells were engineered to over-express wtEGFR (U87wt), mutant EGFR (de 2-7EGFR, deltaEGFR, ΔEGFR or EGFRvIII) (U87Δ) or the kinase-deficient ΔEGFR (U87ΔK) Cell lines that were mixed with U87wt were engineered to express the LacZ gene and so could be distinguished by X-Gal staining. Cell populations expressing equivalent levels of over-expressed receptors were selected by FACS. $1 \times 10^6$ U87wt cells (U87wt 100%), or these cells mixed with U87 Par, U87ΔK or U87Δ in ratios 90-10% or 99-1%, were injected subcutaneously into the right flank of 4 to 5 weeks-old female athymic nude mice and tumor volume was measured periodically. Tumor growth kinetics (FIG. 1A) and tumor volume at the end of the experiment (FIG. 1B) were measured.

A strong tumor growth enhancement was observed when U87wt cells were co-injected with U87Δ at either 90-10% or 99-1% ratios. This tumor potentiation was not observed when U87wt cells were injected together with U87 Par or U87ΔK, corroborating our hypothesis that deltaEGFR induces enhanced proliferation, and that the enhanced proliferation is dependent on the kinase activation of deltaEGFR. Tumor volumes at day 21 after injection of U87wt+U87delta cells were significantly bigger than the theoretical volume of the sum of two different population volumes.

Example 3 deltaEGFR Enhanced Tumorigenicity of wtEGFR Over-Expressing U87 (A) and Ink4/Arf$^{-/-}$ Murine Astrocyte Cells (B)

Figure 2A:
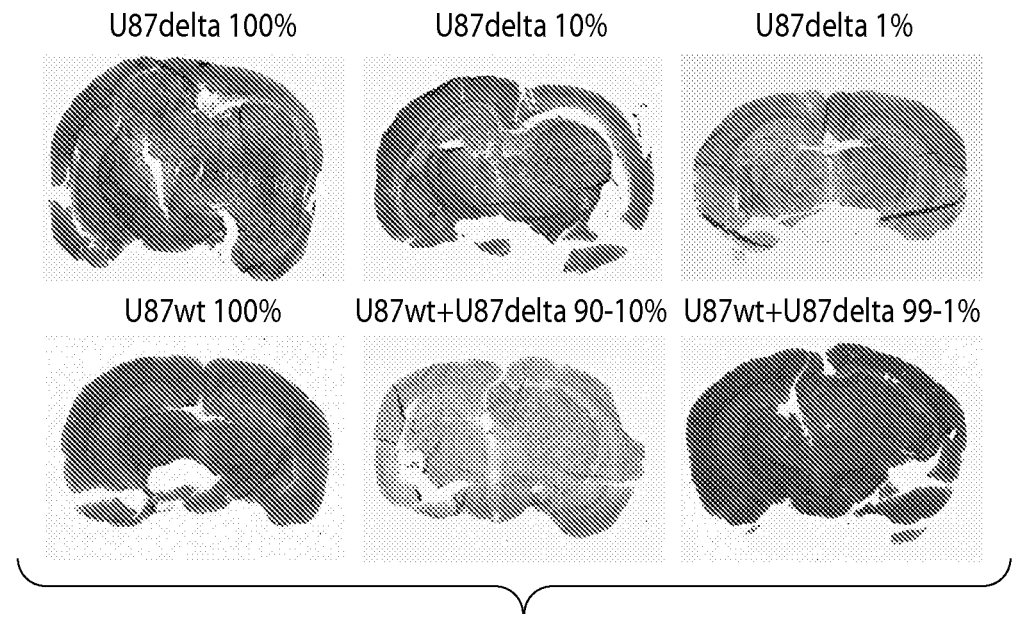
FIGS. 2A and 2B show hematoxylin and eosin (H&E) staining of brain cryo-sections from mice.

$0.5 \times 10^6$ cells (100%) were injected intracranially into nude mice using a guide-screw system as described by Lal S. et al. (*J Neurosurg* 92(2):326-333, 2000). Time matched mice were sacrificed and brains were removed, fixed in 4% PFA and embedded in OCT. H&E stain was performed on 6 μm cryosections in order to compare tumor size between U87wt, U87Δ and mixtures 90-10% or 99-1% of U87wt and U87Δ, respectively. Similar to the results in FIGS. 1A and 1B, a strong tumor growth potentiation was observed when U87wt cells were mixed with U87Δ. This effect was more evident when injections were performed with 99% U87wt with 1% U87Δ (FIG. 2A). No tumor enhancement was observed when U87wt cells were mixed with U87 Par or U87ΔK, confirming the role of catalytically active ΔEGFR in the tumorigenic growth promotion of glioma cells expressing wtEGFR. These results indicated that U87Δ not only can enhance heterogeneous tumor growth subcutaneously, but also intracranially.

Figure 2B:
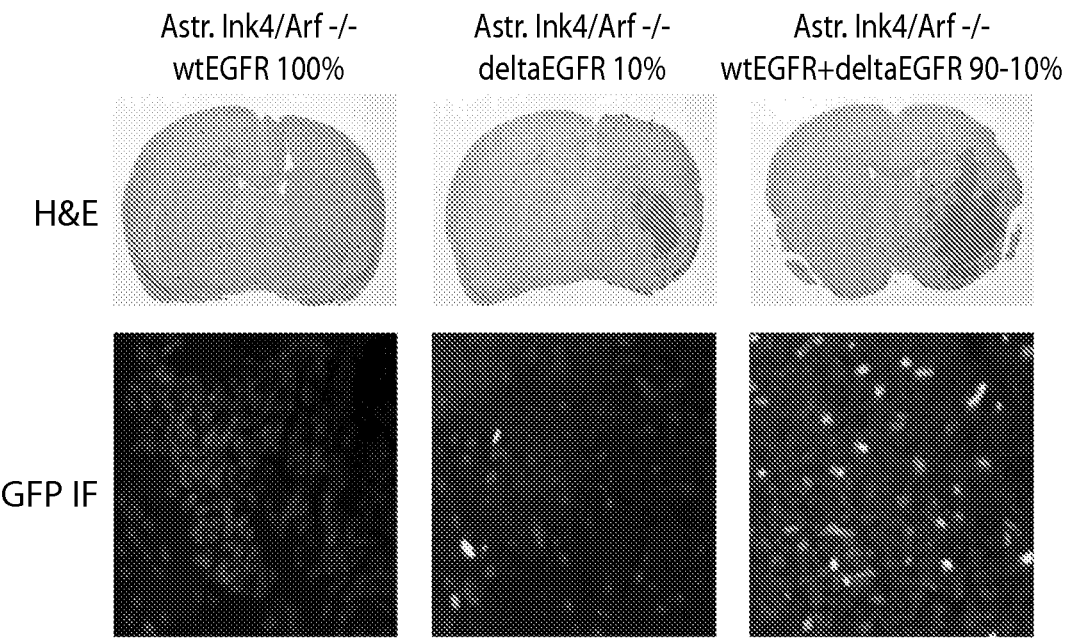

To confirm that these results were not cell line specific, the trans-proliferation model was further tested with murine Ink4/Arf$^{-/-}$ astrocytes engineered to over-express wt and deltaEGFR. Previously it had been shown that Ink4/Arf$^{-/-}$ deltaEGFR astrocytes are tumorigenic upon intracranial injection in nude mice. However Ink4/Arf$^{-/-}$ wtEGFR astrocytes require the introduction of EGF to elicit this effect (Bachoo et al., *Cancer Cell* 1:269-77, 2002). It was therefore hypothesized that deltaEGFR over-expressing astrocytes might be able to promote the tumorigenicity of wtEGFR over-expressing astrocytes if the cells were co-injected. In order to demonstrate the presence of wtEGFR astrocytes within the tumor, these cells were tagged with nuclear GFP and injected either alone or mixed with deltaEGFR over-expressing astrocytes (FIG. 2B). As shown in the upper panel of FIG. 2B, tumor size at day 22 after injection was significantly bigger in mice co-injected with 90% wtEGFR and 10% deltaEGFR Ink4/Arf$^{-/-}$ murine astrocytes than with 10% of deltaEGFR Ink4/Arf$^{-/-}$ astrocytes alone. It was also confirmed that wtEGFR astrocytes did not form tumors. These results not only demonstrated that there was tumor growth potentiation when wtEGFR astrocytes were mixed with deltaEGFR astrocytes, but also showed the presence of wtEGFR astrocytes within the tumor by immunofluorescence (GFP IF) (FIG. 2B, lower panel). Interestingly, a small number of GFP positive cells were detected in mice injected with wtEGFR astrocytes only, which may represent dormant cells that could be activated upon activation of the receptor.

Example 4

Analysis of Tumor Composition by X-Gal Staining and Flow Cytometry

Figure 3A:
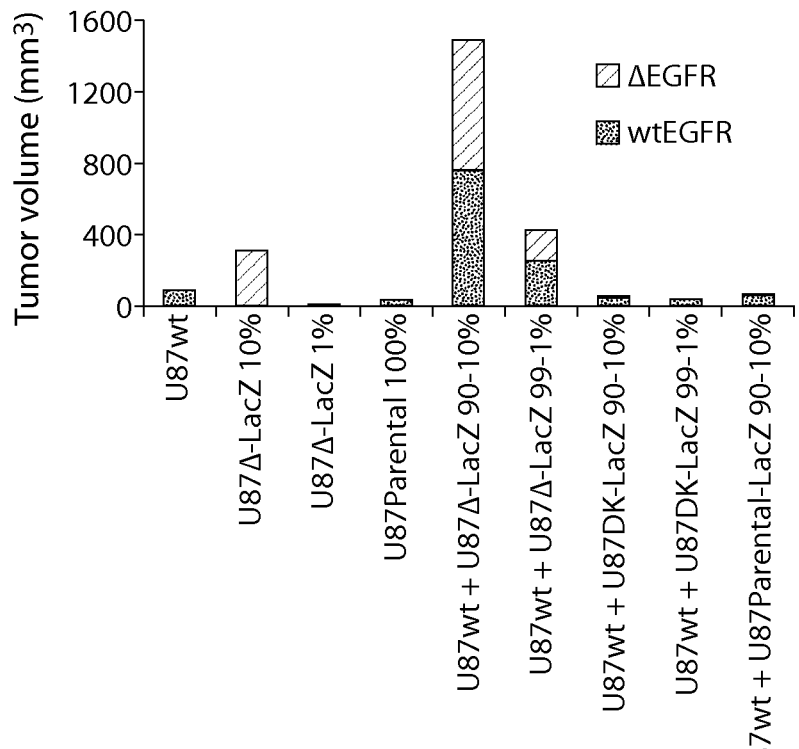
FIG. 3A is a graph showing the composition of various tumor samples in 4 to 5 week old mice injected with the indicated cell types, as assayed by X-Gal staining.

To determine the relative cell type composition of the mixed U87 xenografts, X-Gal staining was performed to detect LacZ-tagged U87delta cells. Representative images of X-Gal stained tumors obtained after injection of admixed U87wt and U87delta cells show a significant number of U87delta cells (LacZ positive) among U87wt cells (LacZ negative). Specifically, the large tumors that resulted from an initial inoculum ratio of 90% U87wt combined with 10% U87delta cells resulted in a final composition of 51.5% U87wt and 48.5% U87delta cells, while tumors from mice injected with 99% U87wt plus 1% U87delta were composed of 58.7% U87wt and a 41.3% U87delta cells. In contrast, the small tumors formed by the mixture of U87wt with U87ΔK or U87 Parental cells were predominantly composed of U87wt cells (FIG. 3A). Notably, the absolute tumor volume attributable to U87 wt cells was approximately 3-10-fold greater in tumors resulting from an injection of U87wt plus U87delta cells than in tumors resulting from an injection of U87wt cells alone, or U87wt with U87ΔK or U87 Parental cells, demonstrating the dramatic growth effect of U87Δ cells on U87wt cells within the same tumor.

Figure 3B:
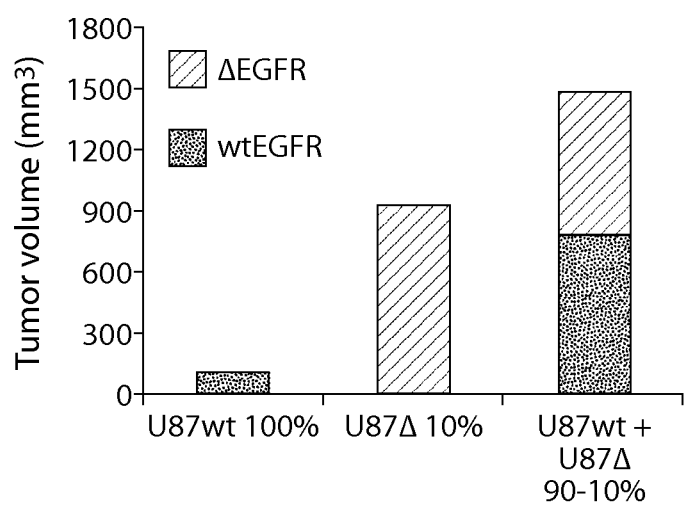
FIG. 3B is a graph showing the composition of tumor samples as assayed by flow cytometry using Ab-1 (FITC) and Ab-5 (APC) antibodies to stain tumors formed after infection of U87wt mixed with U87delta at the indicated ratios.

To more accurately quantify tumor composition, differential fluorescence activated cell sorting analysis was performed on single cell suspensions of subcutaneous xenografted mixed tumors stained with two different antibodies against EGFR, one antibody that recognizes the wt and mutant receptor (Ab-1) and another antibody that only recognizes the wt receptor (Ab-5). Using this approach, tumors generated 24 days post injection of 90% U87wt plus 10% U87delta cells were shown to consist of 52.8±17.3% (mean±SD) wt and 47.2±17.3% deltaEGF receptors (FIG. 3B), confirming the LacZ staining results. This further illustrates that DEGFR-expressing cells do not exert an overwhelmingly dominant growth advantage in heterogeneous tumors containing amplified levels of wtEGFR, but rather stimulate the latter to grow more robustly.

Example 5

Treatment of U87 Wt Cells with U87Delta Conditioned Media (CM) Activates EGFR

To analyze the effect of deltaEGFR cells on wtEGFR activation, conditioned media was collected from 48 h-starved deltaEGFR cells and used to stimulate U87wt cells, also starved 48 h. Western blot analysis of EGFR activation and known signaling molecules downstream of the receptor was performed on lysates of U87wt cells stimulated for 15 minutes with serial dilutions of U87delta CM, negative control U87 Par CM or positive control EGF ligand. Membranes were interrogated with anti-pTyr monoclonal antibody (4G10) to check the activation of the EGFR, and with phospho-specific antibodies directed to the major known transduction proteins involved in tumorigenesis in GBMs (gliobastoma multiformes): Akt, ERK1/2 (a.k.a., MAPK) and STAT3.

Figure 4:
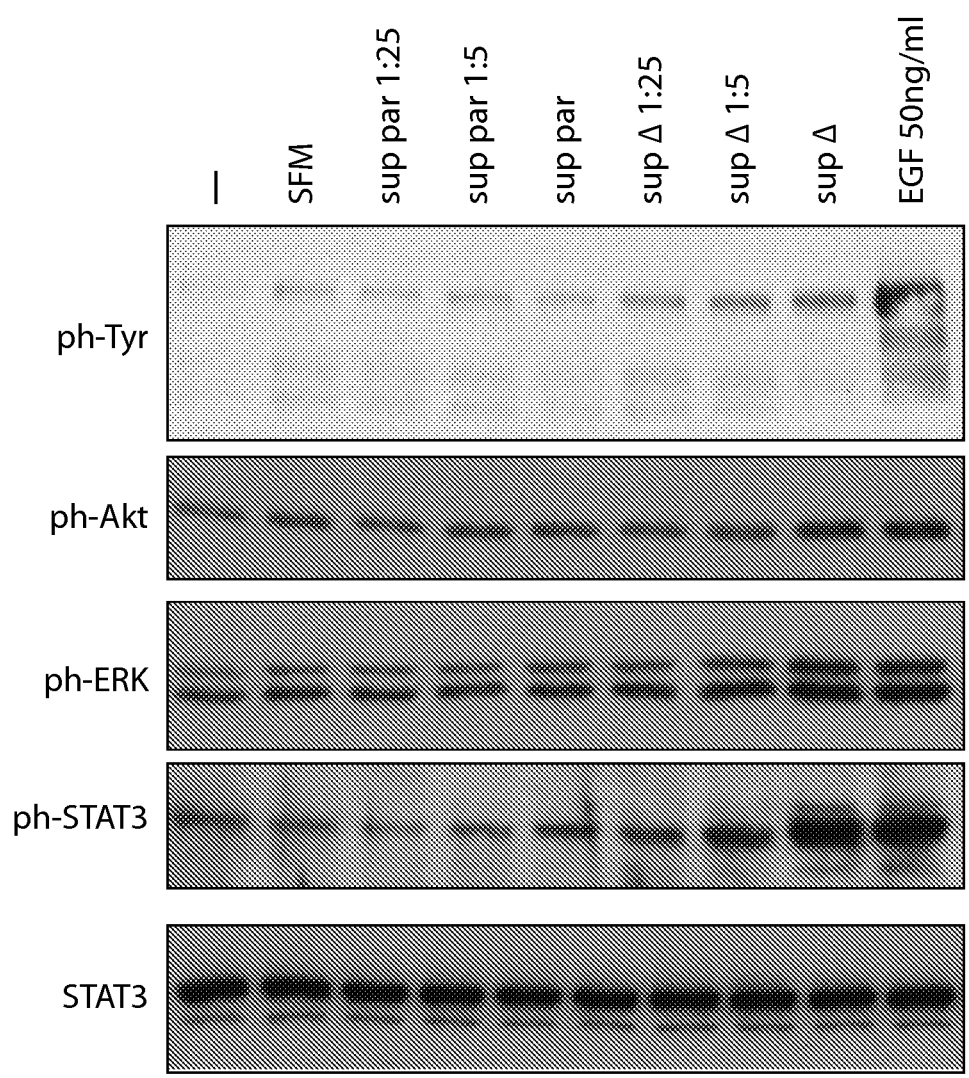
FIG. 4 is a panel of Western blots showing analysis of EGFR activation and known downstream signaling molecules in U87wt cells stimulated with serial dilutions of U87delta CM or negative control U87 Par CM, or positive control EGF ligand.

FIG. 4 shows that these pathways were activated in response to the U87Δ CM stimulation, as shown by the increase of the phosphorylated forms of those proteins in a dose-dependent manner. In contrast, CM from U87 Par cells failed to activate EGFR or any of these pathways. Notably the level of phosphorylation of these proteins, except EGFR, is at the same extent for the undiluted conditioned medium and the high dose of EGF that was used, indicating that activation of EGFR downstream signaling is efficiently mimicked by factors secreted from U87Δ. Activation of these pathways was also elicited in part by abundant IL-6 produced and secreted by the deltaEGFR-expressing cells.

Similarly, wtEGFR phosphorylation was observed to be significantly higher (p<0.05) in mixed tumors than in tumors obtained after injection of U87wt alone (0.576±0.166 vs 0.19±0.007), while no differences in phosphorylation were detected for ΔEGFR in the mixed tumors compared to the tumors generated from injection of U87Δ alone (1.215±0.225 vs 1.179±0.260).

To determine whether the activation of these intracellular pathways is dependent on the kinase activity of EGFR, the effect of Δ CM in the presence of the EGFR inhibitor AG1478 was analyzed. Pre-treating U87wt cells with this inhibitor for 30 minutes prior to Δ CM stimulation, completely abolished the activation of EGFR. Moreover, it was also observed that activation of Akt and ERK was maintained at the level of untreated cells. Conversely, the activation of STAT3 caused by exposure to the Δ CM was not affected by blocking the activity of EGFR with this inhibitor. These results suggested that at least two (or more) soluble factors exist in the Δ CM, producing different effects on target U87wt cells: (i) activation of EGFR and its intracellular signaling surrogates (Akt, ERK), via receptor kinase activity, and (ii) STAT3 activation independent of EGFR stimulation.

Example 6 wtEGFR Activation is not Caused by any of its Natural Ligands

The results obtained with Δ CM would suggested that U87Δ cells secrete one or more factors responsible for EGFR activation in wtEGFR cells. In order to test whether these were known ligands for the EGFR, neutralization using an EGFR ligand trap was performed. This recombinant ligand-binding protein consisted of the extracellular portion of the EGFR bound to a human Fc fragment and bound the known EGFR ligands with high affinity. Pre-incubation of recombinant EGF with 10 µg/ml of the ligand trap reduced the activation of EGFR as well as Akt and ERK, however, no effect on either EGFR or these two downstream pathways was observed when Δ CM was pretreated with the ligand trap. As expected, STAT3 activation was not affected in the presence of the ligand trap. To further demonstrate that EGFR ligands were not involved in the transactivation of U87wt by Δ CM, ELISA was used to quantify the concentrations of EGF, TGF-α, amphiregulin, HB-EGF and betacellulin in U87Δ CM as well as in control U87 Parental, U87wt and U87ΔK CM. All of these tested EGFR ligands were either undetectable or showed no significant increase in expression in CM when compared to the conditioned media from the other cell lines. Given the possibility that active soluble EGFR ligands may be released from the surface of the target cells by proteolytic cleavage of membrane-anchored precursors (Sanderson et al., 2006), Δ CM was tested for the ability to induce the release of EGFR ligands expressed on the surface of U87wt cells. U87wt cells were stimulated with serum-free medium, recombinant EGF and U87Δ CM, and then these media were collected to analyze by ELISA changes in EGFR ligand concentration after the stimulation. None of the tested ligands showed any significant change in concentration, indicating that EGFR is not stimulated by soluble factors shed from the membrane of wtEGFR cells. Confirmation of these results was achieved by incubation of Δ CM with neutralizing antibodies against each EGFR ligand; these also failed to block the ability of the CM to activate EGFR, while each antibody tested was able to block the activity of the respective recombinant ligand. In summary, U87Δ cells do not produce a detectable EGF family ligand activity, pointing to other factors driving inter-cellular activation of wtEGFR.

Example 7

IL-6 is Over-Expressed in U87Delta Cells and in deltaEGFR-Positive GBM Clinical Samples To identify soluble factors expressed by U87Δ cells that could potentially mediate intercellular communication with and promote the proliferation of U87wt cells, a cytokine array was used to qualitatively detect 79 human cytokines and growth factors in supernatants of cultured cells. With this approach, IL-6 was found to be significantly upregulated in U87Δ cells compared to the other U87 cell lines. To further quantify IL-6 upregulation in U87Δ CM, an ELISA assay was performed on supernatants from the different U87 cell lines collected after 48 hours starvation. The values obtained (pg/ml/4×105 cells) illustrate a 13-fold increase of IL-6 secretion for U87Δ (3813±2) compared to U87 Parental cells (299±25), while no significant increase was detected with U87wt (567±85) or U87ΔK (355±75) CM.

Nineteen GBM tumor samples, U87 cell lines and one normal brain sample were analyzed for ΔEGFR and IL-6 RNA expression by real time PCR. As expected, U87Δ demonstrated a significant higher (p<0.001) expression of IL-6, while no significant differences in IL-6 expression were observed between the rest of U87 cell lines. Notably, we observed a very significant correlation between ΔEGFR and IL-6 expression (p=0.0034) in the GBM tumor samples. All tumor samples that presented ΔEGFR expression also showed high IL-6 expression (8/8), while only three tumors that did not show ΔEGFR expression over-expressed IL-6 (3/11).

Example 8 siRNAs Specific for deltaEGFR or wtEGFR Reduced Tumor Growth After Subcutaneous Injection of Ex Vivo Transfected Cells The present inventors observed that in vitro treatment of cells expressing wtEGFR with conditioned media from cells overexpressing deltaEGFR resulted in activation of STAT3, Akt, Erk1/2 and wtEGFR. In vivo tumor growth potentiation was also observed when wtEGFR overexpressing cells were mixed with deltaEGFR expressing cells, but not when those cells were mixed with cells with normal levels of wtEGFR or overexpressing a dead kinase version of deltaEGFR. Based on these observations, siRNA technology was used to knock-down either wt or deltaEGFR to assess the effect of specific receptor ablation on tumorigenicity and contribution to heterogeneity. As shown below, siRNAs specific for deltaEGFR or wtEGFR were able to reduce tumor growth after subcutaneous injection of ex vivo transfected cells.

In Vitro siRNA Screening:

siRNAs non-stabilized (Table 2) and stabilized (Table 3), designed to be specific (i) to wtEGFR, (ii) to deltaEGFR, and (iii) to both receptors, were synthesized. U87-wtEGFR (Nagane et al, Cancer Research, 56: 5079-5086, 1996) and U87-deltaEGFR (Nishikawa et al, PNAS, 91: 7727-7731, 1994) cells were used as test cell lines to assess the specificity of these siRNA molecules. The term "deltaEGFR," as used in this example, refers to an EGFR gene construct deleted for exons 2-7. U87-deltaEGFR cells are recombinant cells expressing an EGFR gene deleted for exons 2-7 as described in Nishikawa et al. (1994). U87-wtEGFR cells are recombinant cells expressing a wtEGFR gene as described in Nishikawa et al. (1994).

Cells were seeded in 24 well plates at 48,000 cells per well in DMEM medium (Cellgro) supplemented with 10% fetal bovine serum and L-Glutamine. The following day, siRNAs were transfected at 100 nM, 10 nM and 1 nM concentrations using Lipofectamine™ 2000 (Invitrogen) and OptiMEM (Gibco). Twenty four hours after transfection, the medium was changed to DMEM supplemented with 10% fetal bovine serum, penicillin/streptomycin and L-Glutamine.

Cells non-transfected as well as transfected with a siRNA specific for GFP or Luciferase protein were included as negative controls.

Three days after transfection, protein lysates were prepared using RIPA buffer (150 mM NaCl, 50 mM Tris-HCl pH 7.5, 1 mM EDTA, 1% NP-40, 0.1% SDS and 0.5% sodium deoxycholate) supplemented with protease inhibitors (Roche) and 5 μg of protein were resolved on 12% NuPAGE Bis-Tris acrylamide gels (Invitrogen). Gels were blotted onto nitrocellulose membranes, blocked with 5% milk in TBS-Tween and probed with anti-EGFR monoclonal antibody, C13, which recognizes both wt and mutant EGFR (BD). Membrane bound C13 antibody was detected with HRP-conjugated anti-mouse IgG (Dako) followed by chemiluminiscence. Nitrocellulose membranes were also probed with anti-actin antibody as a positive control for protein loading.

In Vitro Specificity Test:

Specificity for the receptor for which each siRNA candidate was designed was assessed by transfecting siRNAs at 100 nM dose in the U87 cell line that expresses the other receptor. Expression knock-down was assessed by western blot as previously described.

To exclude that any reduction in the cytokine synthesis was caused by off-target effects of the siRNAs, the concentration of both IL-6 and IL-8 was measured in the samples where an siRNA was found to have a strong effect on the expression of IL-6, and compared to non-transfected cells as well as cells transfected with an siRNA against GFP or Luciferase Cells non-transfected as well as transfected with an siRNA against GFP or Luciferase protein were included as negative controls.

In Vitro Dose-Response Analysis:

siRNAs determined to be specific and able to knock-down the expression of the receptor for which they were designed were tested again in U87-deltaEGFR and U87-wtEGFR to determine the minimal effective dose to achieve receptor expression knock-down. Cells were seeded in 24 well plates at 48,000 cells per well and siRNAs were transfected the following day at 100, 25, 5 and 1 nM concentrations using Lipofectamine™ 2000. Twenty four hours after transfection, medium was changed and two days after protein lysates were obtained as described previously. Cells non-transfected as well as transfected with a siRNA against GFP or Luciferase protein were included as negative controls. Receptor expression was analyzed by western blot as described previously.

In Vitro Durability Test:

siRNAs determined to be robust in the ablation of deltaEGFR or wtEGFR expression, when transfected at low concentration, were tested for suppression durability using U87-deltaEGFR and U87-wtEGFR cell lines.

Cells were seeded in 24 well plates at 48,000 cells per well and siRNAs were transfected the following day at 25 nM concentration using Lipofectamine™ 2000. Protein lysates were obtained using RIPA buffer supplemented with protease inhibitors at days 3, 5, 7, 10, 14 and 17 post-transfection. Cells non-transfected as well as transfected with a siRNA against GFP or Luciferase protein were included as negative controls. Receptor expression was analyzed by western blot as described previously.

Ex Vivo Experiments:

To determine the effect of specific receptor knock-down on tumorigenicity, cells were transfected and then injected subcutaneously into nude mice.

Briefly, 25 cm$^2$ plates were seeded with $1.3 \times 10^6$ cells and one day after they were transfected with 25 nM or 100 nM siRNA using Lipofectamine™ 2000. The following day, the medium was changed and cells were split into larger dishes when they were almost confluent.

Cells non-transfected as well as transfected with a siRNA against GFP or Luciferase protein were included as negative controls.

One million U87-wtEGFR or $0.5 \times 10^6$ U87-deltaEGFR transfected cells were resuspended in 100 μl PBS. Cells were injected subcutaneously into the right flank of Nu/Nu mice using a 1 ml syringe with a 26G needle. Tumor volume was measured starting at day 5 after injection and was calculated using the formula $0.5 \times L \times W^2$. Mice were euthanized when tumor volume reached 1500 mm$^3$.

Protein lysates were prepared from the remaining cells of the injection using RIPA buffer supplemented with protease inhibitors. Receptor expression was analyzed by western blot as described previously.

Results

Figure 5A:
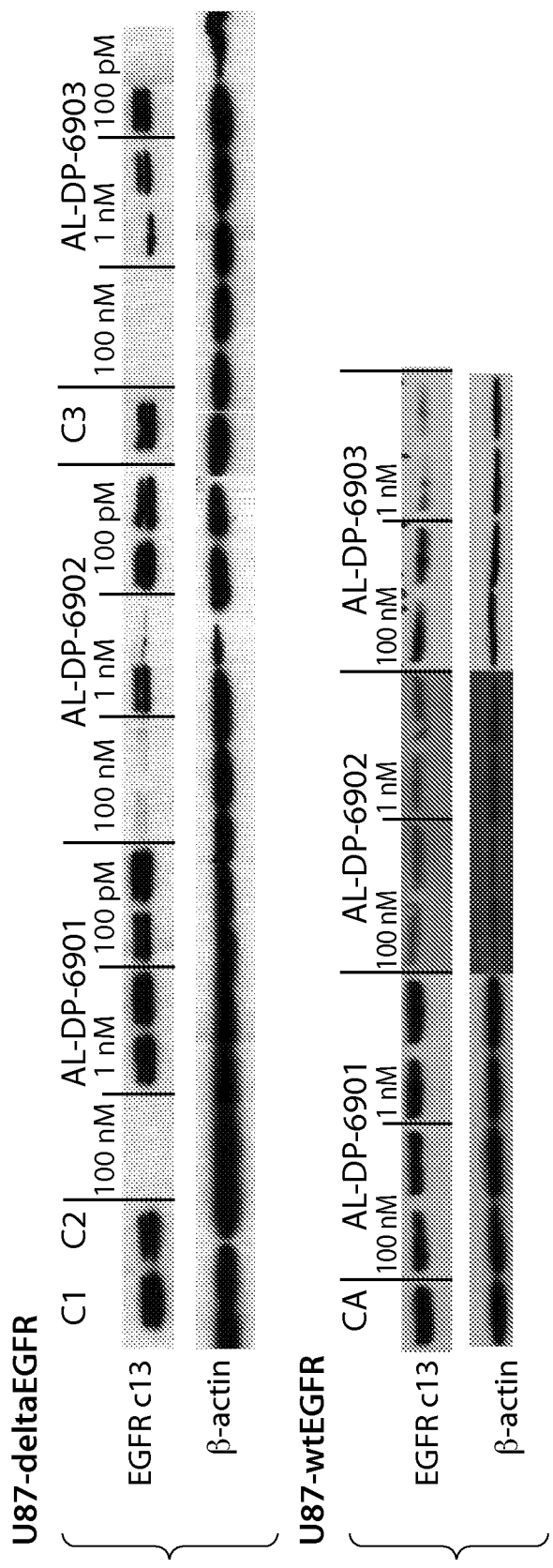
FIGS. 5A-5C are Western blots showing the activity of siRNAs targeting deltaEGFR (FIG. 5A), wildtype EGFR (FIG. 5B), or both mutant and wildtype receptors (FIG. 5C). C1, C2, C3, and CA indicate negative controls (untransfected cells).
Figure 5B:
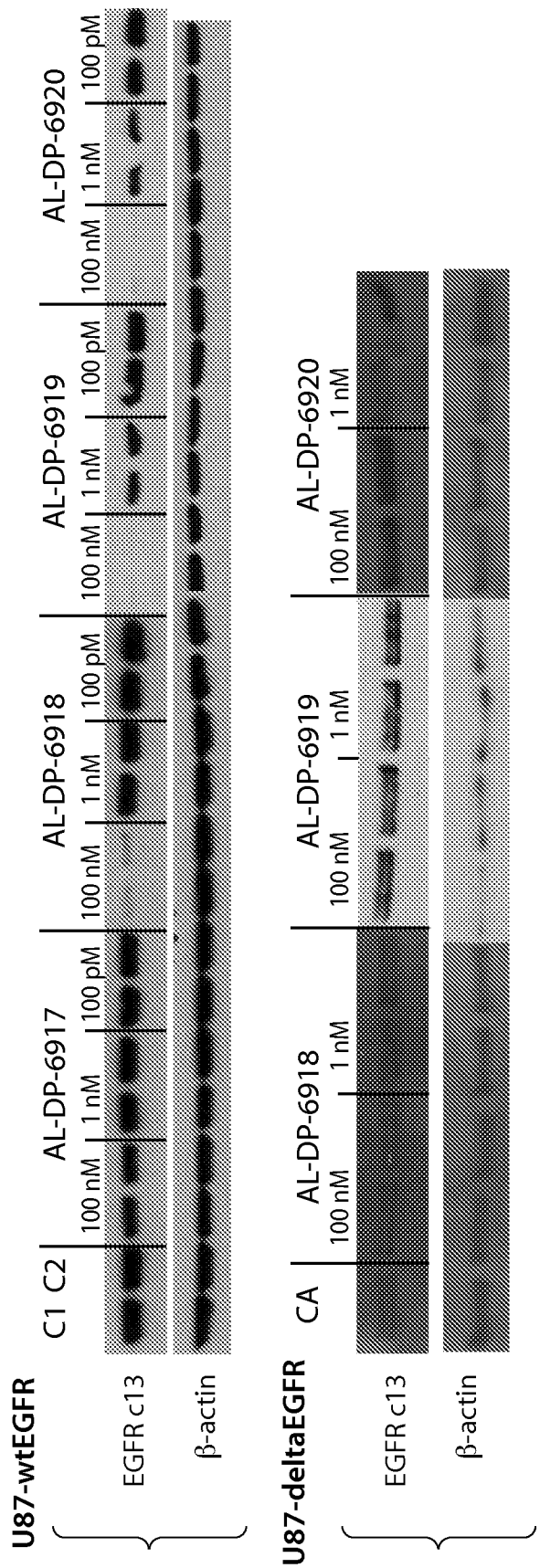

In Vitro siRNA Screening (Table 4):

Non-Stabilized siRNAs:

DeltaEGFR-Specific siRNAs:

Western blot analysis demonstrated that 7 of 8 deltaEGFR-specific siRNAs were capable of complete elimination of the mutant receptor expressed in U87-deltaEGFR cells when tested at 100 nM (AL-DP-6901-6907) while three (AL-DP-6902, -6903, -6906) were able to effect a modest receptor reduction as low as 1 nM concentration (Table 4 and FIG. 4A). One siRNA, AL-DP-6908, had no effect. To show specificity for the mutant receptor, each deltaEGFR-specific siRNA was tested against U87-wtEGFR cells. Only one of the siRNAs (AL-DP-6906) that reduced deltaEGFR expression was also able to reduce wtEGFR expression.

wtEGFR-Specific siRNAs:

As above, western blot analysis was used to demonstrate that 5 of 8 wtEGFR-specific siRNAs were capable of complete elimination of the wt receptor expressed in U87-wtEGFR cells when tested at 100 nM (AL-DP-6918-6921 and -6923), while two (AL-DP-6919 and -6920) were able to effect a modest receptor reduction as low as 1 nM concentration (Table 4 and FIG. 5B). Three siRNAs (AL-DP-6917, -6922, and -6924) had little or no effect. To show specificity for the wt receptor, each active wtEGFR-specific siRNA (AL-DP-6918-6921 and -6923) was tested against U87-deltaEGFR cells with none showing reduction of the mutant receptor.

Wt and deltaEGFR-Specific siRNAs:

As above, western blot analysis was used to demonstrate the specificity of 8 siRNAs designed to knock-down the expression of both wt and deltaEGFR. Of this series, three siRNAs were able to simultaneously knock-down both receptors (AL-DP-6913, -6915, and -6916) albeit the effect was stronger for suppressing deltaEGFR (Table 4 and FIG. 5C).

Figure 5C:
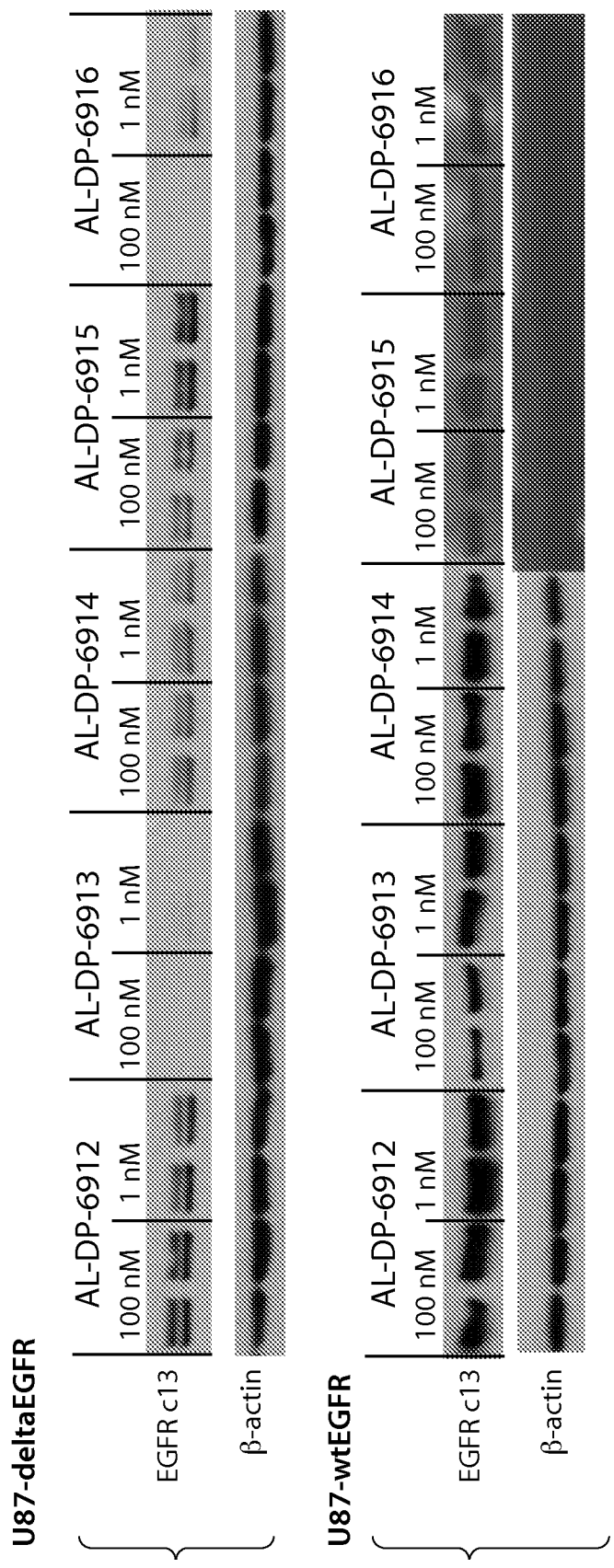

In FIGS. 5A-5C, two samples were run for each treatment condition. Membranes were blotted with c13 antibody to detect EGFR and beta-actin antibody to confirm equivalent loading between lanes.

Figure 6A:
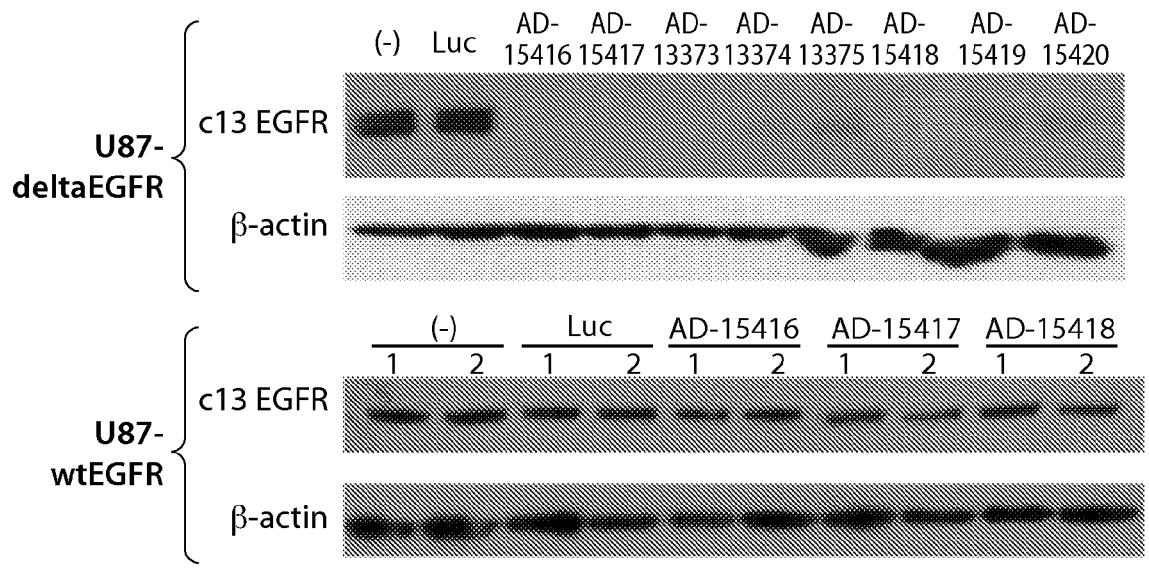
FIGS. 6A-6C are Western blots showing the activity of siRNAs targeting deltaEGFR (FIG. 6A) or wildtype EGFR (FIG. 6C).
Figure 6B:
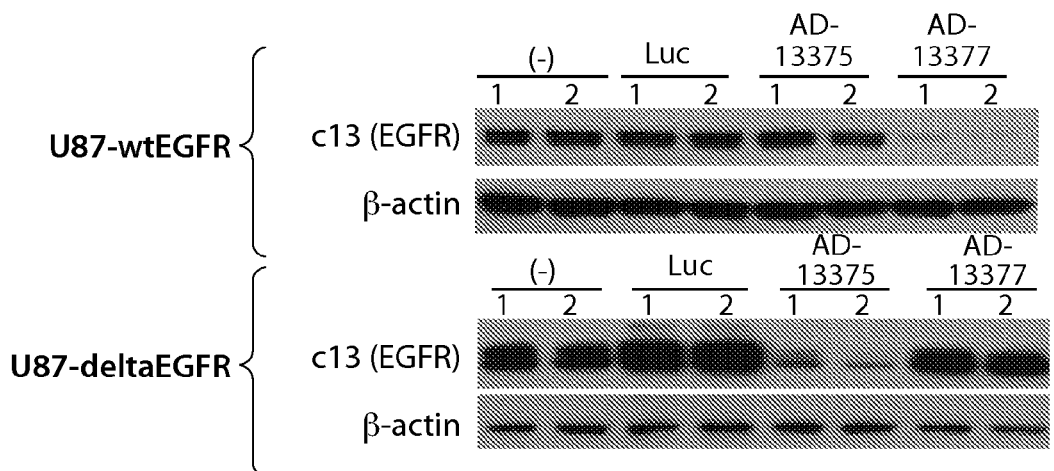
Figure 6C:
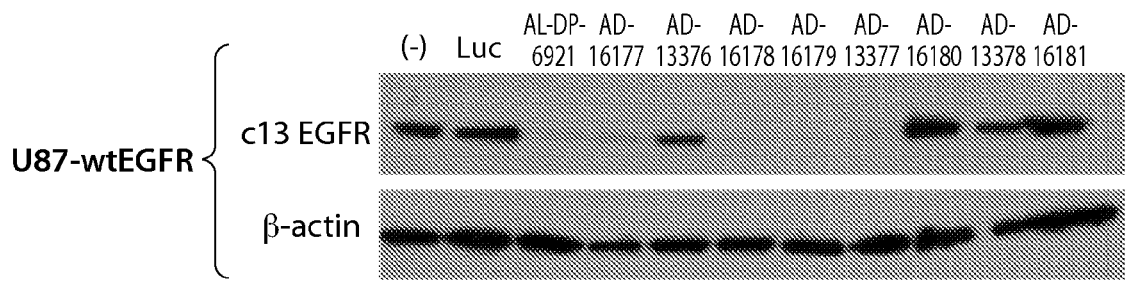

Stabilized siRNAs:

DeltaEGFR-Specific siRNAs:

Western blot analysis demonstrated that 8 of 8 deltaEGFR-specific siRNAs were capable of reducing mutant receptor expression in U87-deltaEGFR cells when tested at 25 nM (Table 4 and FIGS. 6A-B). To show specificity for the mutant receptor, deltaEGFR-specific siRNAs (AD-15416, AD-15417, AD-13375, AD-15418) were tested against U87-wtEGFR cells. None of siRNAs tested resulted in reduced wtEGFR expression.

wtEGFR-Specific siRNAs:

Western blot analysis demonstrated that 4 of 8 wtEGFR-specific siRNAs strongly suppress wtEGFR protein expression (AD-16177, AD-16178, AD-16179 and AD-13377), while 2 of these 8 siRNAs were able to moderately reduce wtEGFR protein expression (AD-13376 and AD-13378) (Table 4 and FIG. 6C). Two of the 8 siRNAs had little or no effect on wtEGFR protein levels (AD-16180 and AD-16181).

In FIGS. 6A-6C, two samples were run for each treatment condition. Membranes were blotted with c13 antibody to detect EGFR and beta-actin antibody to confirm equivalent loading between lanes.

In Vitro Dose-Response Analysis:
Non-Stabilized siRNAs:
DeltaEGFR-Specific siRNAs:

Western blot analysis demonstrate that the four deltaE-GFR-specific siRNAs tested (AL-DP-6901-6903, and -6905) were capable of complete elimination of the mutant receptor expressed in U87-deltaEGFR cells when transfected at 25 nM, nearly complete elimination at 5 nM and partial elimination at 1 nM (FIG. 7A).

wtEGFR-Specific siRNAs:

As above, western blot analysis was used to demonstrate that 4 of 4 wtEGFR-specific siRNAs (AL-DP-6918-6921) were capable to varying degrees of wt receptor elimination in U87-wtEGFR cells (FIG. 7B).

Wt and deltaEGFR-Specific siRNAs:

AL-DP-6913 and AL-DP-6916 were able to suppress expression of both wt and deltaEGFR protein in a dose-dependent manner (FIGS. 7A-B).

In FIGS. 7A and 7B, two samples were run for each treatment condition. Membranes were blotted with c13 antibody to detect EGFR.

Figure 8A:
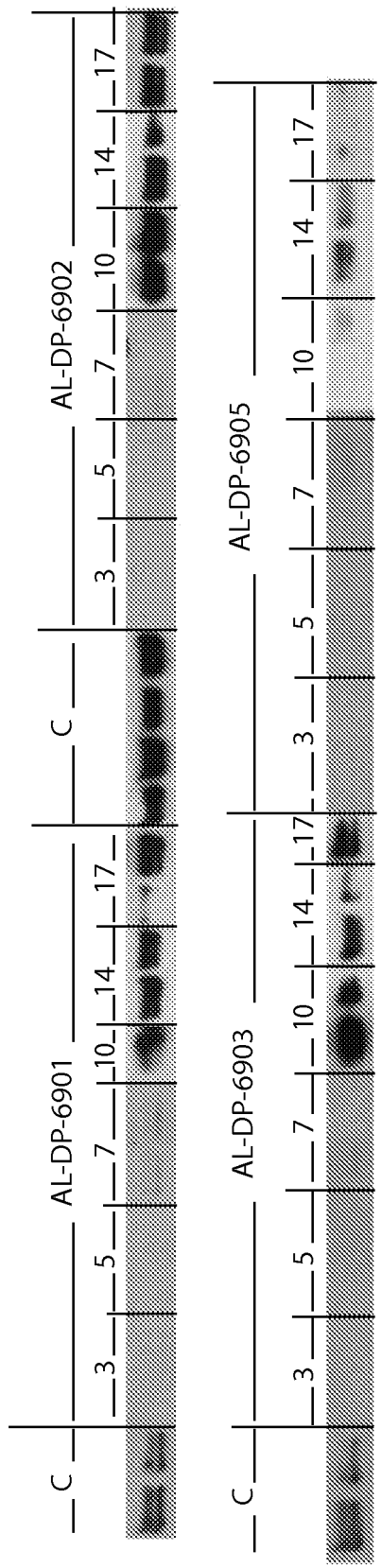
FIGS. 8A-8D are Western blots showing durability of the effect of unstabilized (FIGS. 8A and 8B) and stabilized (FIGS. 8C and 8D) siRNAs.
Figure 8B:
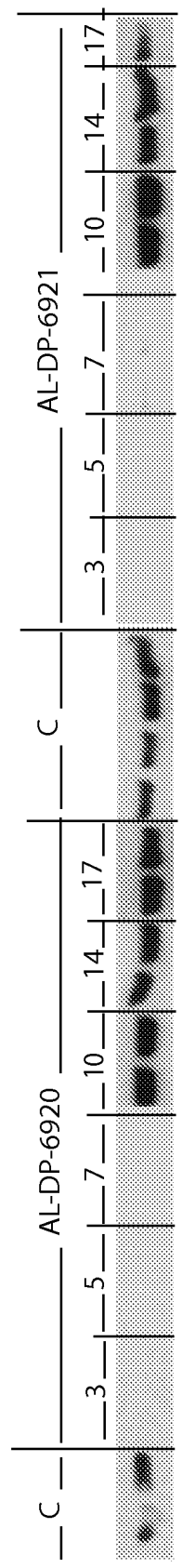

In Vitro Durability Test:
Non-Stabilized siRNAs:
DeltaEGFR-Specific siRNAs:

Western blot analysis demonstrated that 4 of 4 deltaEGFR-specific siRNAs analyzed (AL-DP-6901, AL-DP-6902, AL-DP-6903, AL-DP-6905) were capable of complete elimination of mutant receptor expression in U87-deltaEGFR cells at 7 days after siRNA transfection, while siRNA AL-DP-6905 was capable of durable suppression as far as 10 days after siRNA transfection (FIG. 8A).

wtEGFR-Specific siRNAs:

As above, western blot analysis was used to demonstrate that 2 of 2 wtEGFR-specific siRNAs analyzed (AL-DP-6920, AL-DP-6921) were capable of complete wt receptor expression elimination in U87-wtEGFR cells out to 7 days after siRNA transfection; however, for both siRNAs, receptor levels were restored to control levels by 10 days post transfection (FIG. 8B).

Figure 8C:
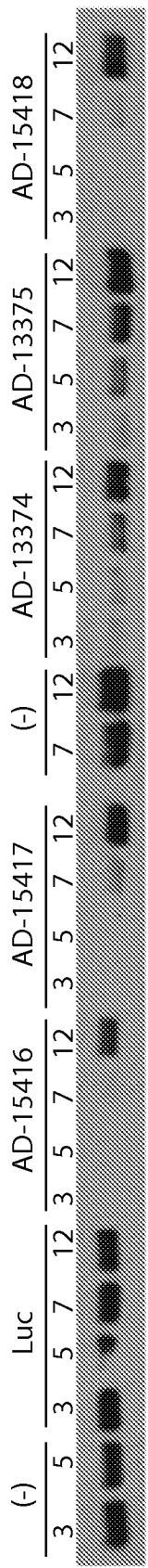
Figure 8D:
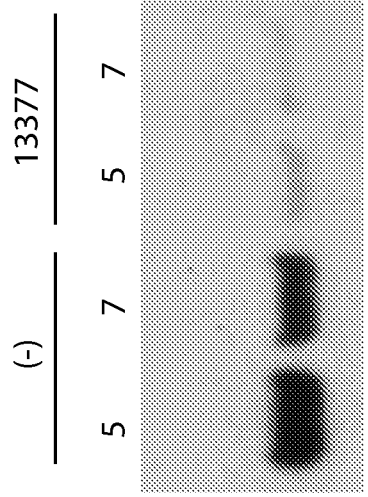

Stabilized siRNAs:
DeltaEGFR-Specific siRNAs:

Western blot analysis demonstrated that 3 of 5 deltaEGFR-specific siRNAs analyzed (AD-15416, AD15417, AD-13374, AD-13375, AD-15418) were capable of complete elimination of mutant receptor expression in U87-deltaEGFR cells 5 days post transfection, while siRNA AD-15416 was capable of durable and complete suppression as far as 7 days post transfection (FIG. 8C). Receptor expression levels were completely restored by day 12 post transfection for all stabilized siRNAs tested.

wtEGFR-Specific siRNAs:

As above, western blot analysis was used to demonstrate that AD-13377 wtEGFR-specific siRNA was capable of complete wt receptor protein elimination in U87-wtEGFR cells out to 7 days after transfection (FIG. 8D). However, receptor levels were restored to control levels by 10 days post transfection.

Figure 9A:
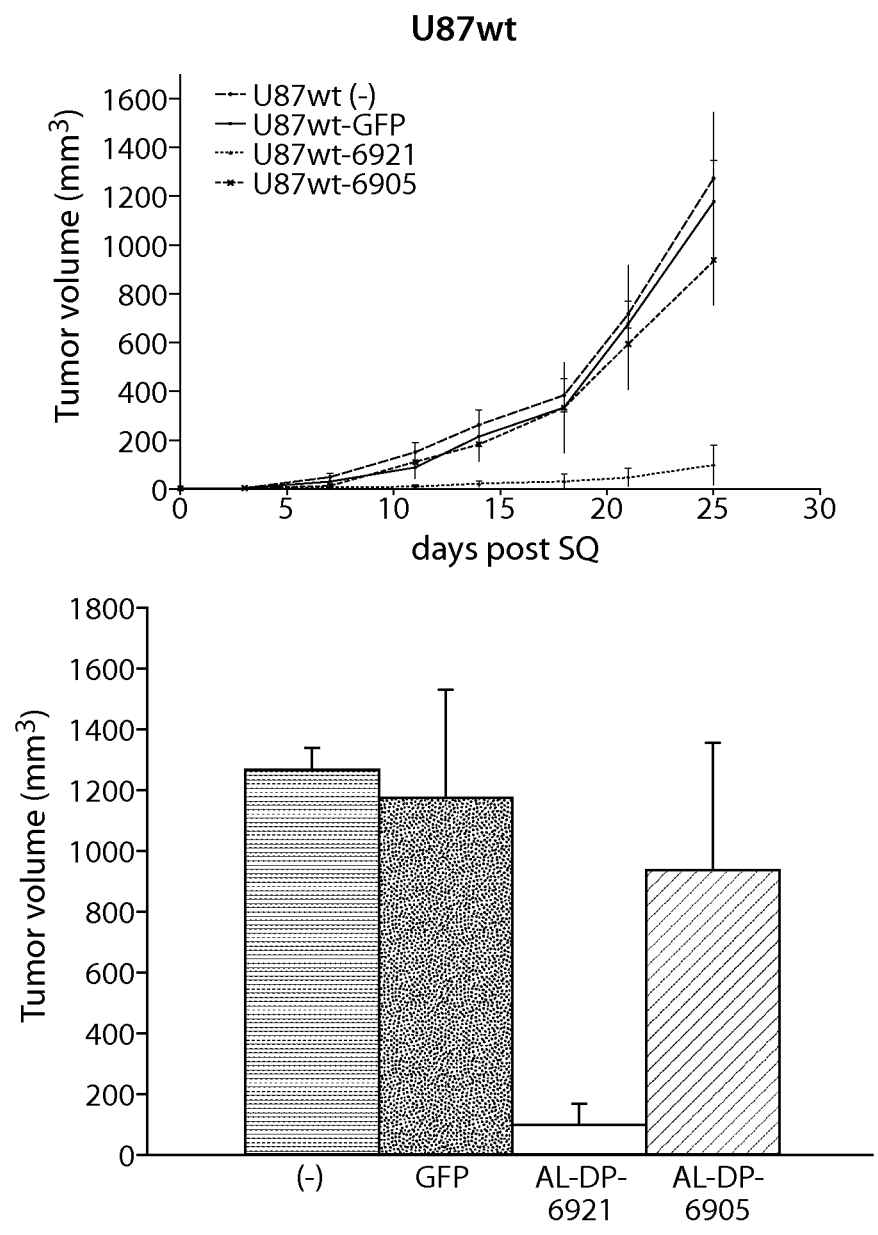
FIGS. 9A and 9B are graphs showing the effects of siRNAs on tumorigenicity in mice injected with U87-wtEGFR cells (FIG. 9A) and in mice injected with U87-deltaEGFR cells (FIG. 9B). Lysates were prepared and Western blots were performed at the indicated day post-transfection. Data are shown as mean±standard deviation (SD).
Figure 9B:
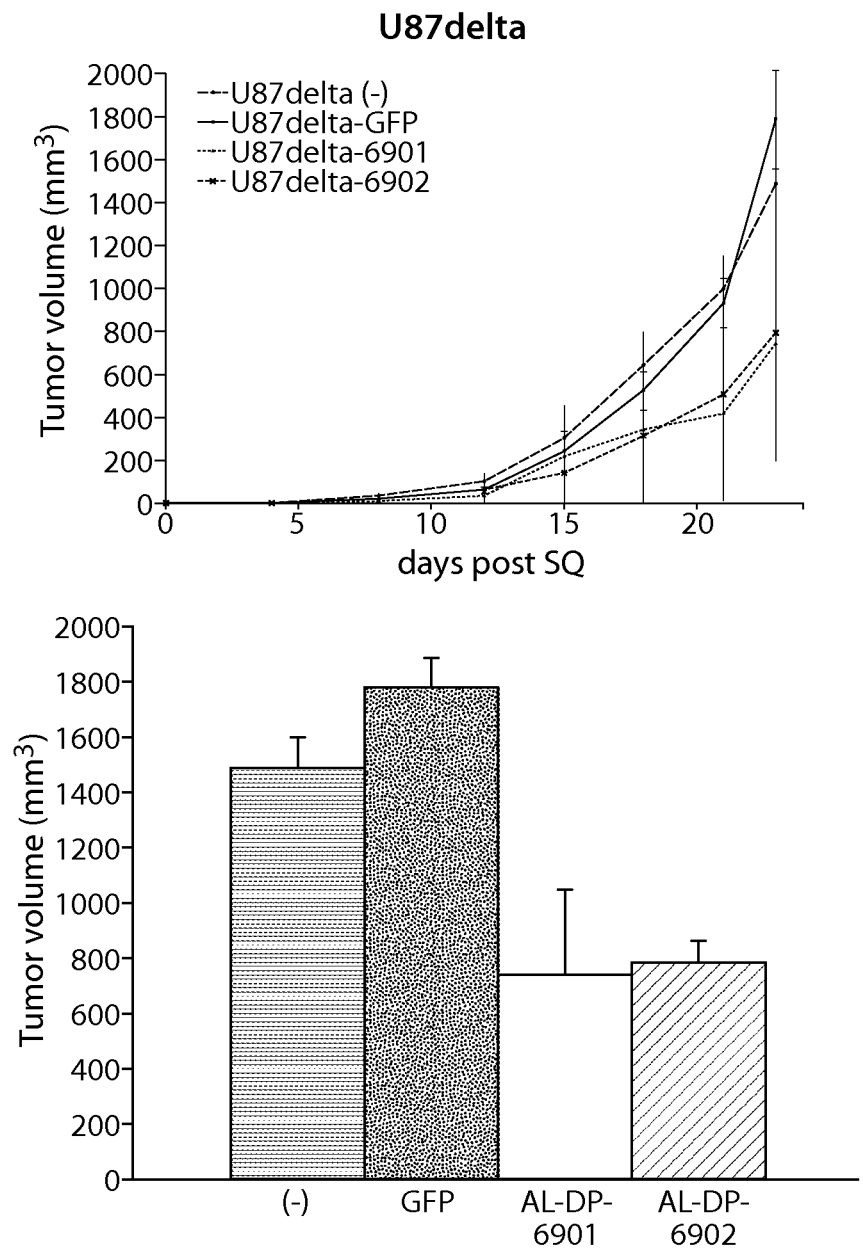

Ex Vivo Experiments:
Non-Stabilized siRNAs:
DeltaEGFR-Specific siRNAs:

U87-deltaEGFR cells were transfected with 100 nM siRNA and injected subcutaneously into nude mice. Treatment with siRNAs AL-DP-6901 and AL-DP-6902 (FIG. 9B) resulted in a substantial reduction of U87-deltaEGFR tumor growth. As a negative control, cells non transfected or transfected with an irrelevant GFP siRNA were included in the study (FIG. 9B). In both of these groups, substantial tumor growth occurred.

wtEGFR-Specific siRNAs:

U87-wtEGFR cells were transfected with 25 nM siRNA concentration and injected subcutaneously into nude mice. Treatment with siRNAs AL-DP-6920 and AL-DP-6921 (FIG. 9A) resulted in ablation of U87-wtEGFR tumor growth. As a negative control, cells non transfected or transfected with an irrelevant GFP siRNA were included in the study (FIG. 9A). In both of these groups, substantial tumor growth occurred.

In FIGS. 9A and 9B, each treatment group included six animals.

Figure 10A:
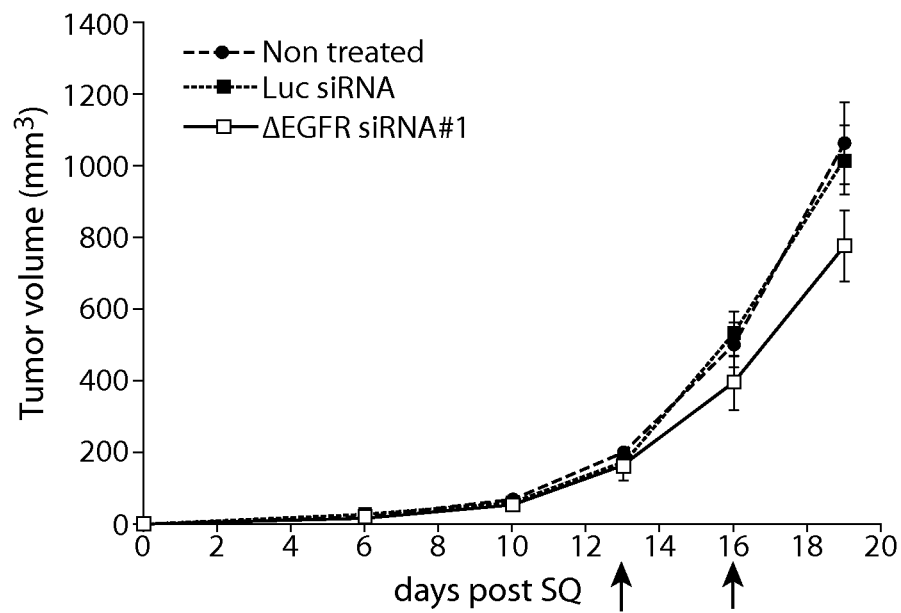
FIGS. 10A and 10B are graphs showing tumor kinetics (FIG. 10A) and volume (FIG. 10B) in nude mice injected with U87delta cells and then injected intratumorally with 5 mg of deltaEGFR siRNA#1 or irrelevant siRNA (siRNA luc).
Figure 10B:
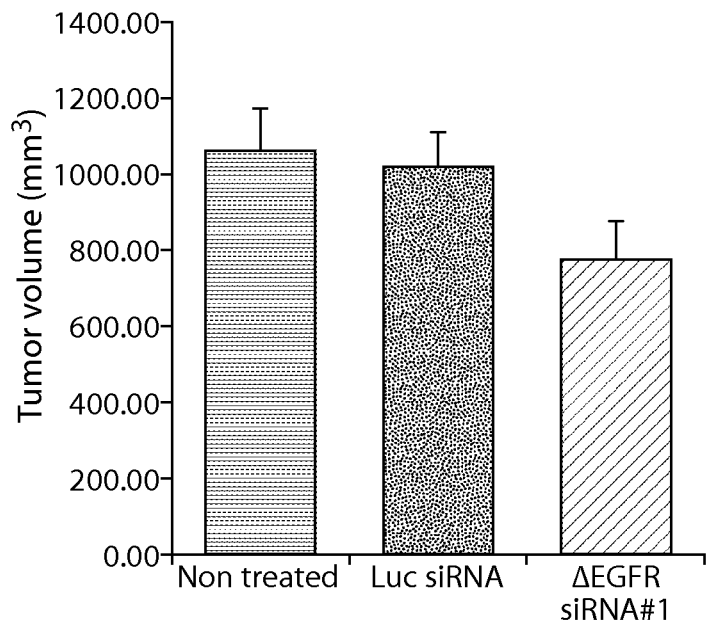

U87delta cells were injected into nude mice and at days 13 (approximately 160 mm$^3$) and 16, 5 mg of deltaEGFR siRNA#1 or irrelevant siRNA (siRNA luc) were administrated intratumorally using JetPei (Polyplus) following the manufacturer's instructions followed by the monitoring of tumor growth as above. These initial results illustrate modest tumor reduction can be achieved in vivo with siRNAs targeting deltaEGFR FIGS. 10A and 10B.

TABLE 2

Sequences of dsRNAs tested for deltaEGFR and wtEGFR gene expression inhibiting activity

| Duplex name | Target position of 5' base of sense strand (see FIGS. 21A and 21B) | Specificity | SEQ ID NO: | Sense strand sequence (5'-3') | SEQ ID NO: | Antisense strand sequence (5'-3') |
|---|---|---|---|---|---|---|
| AL-DP-6901 | 320 | deltaEGFR | 2 | UGGAGGAAAAGAAAGGUAATT | 3 | UUACCUUUCUUUUCCUCCATT |
| AL-DP-6902 | 321 | deltaEGFR | 4 | GGAGGAAAAGAAAGGUAAUTT | 5 | AUUACCUUUCUUUUCCUCCTT |

TABLE 2-continued

Sequences of dsRNAs tested for deltaEGFR and wtEGFR gene expression inhibiting activity

| Duplex name | Target position of 5' base of sense strand (see FIGS. 21A and 21B) | Specificity | SEQ ID NO: | Sense strand sequence (5'-3') | SEQ ID NO: | Antisense strand sequence (5'-3') |
|---|---|---|---|---|---|---|
| AL-DP-6903 | 322 | deltaEGFR | 6 | GAGGAAAAGAAAGGUAAUUTT | 7 | AAUUACCUUUCUUUUCCUCTT |
| AL-DP-6904 | 319 | deltaEGFR | 8 | CUGGAGGAAAAGAAAGGUATT | 9 | UACCUUUCUUUUCCUCCAGTT |
| AL-DP-6905 | 323 | deltaEGFR | 10 | AGGAAAAGAAAGGUAAUUATT | 11 | UAAUUACCUUUCUUUUCCUTT |
| AL-DP-6906 | 324 | deltaEGFR | 12 | GGAAAAGAAAGGUAAUUAUTT | 13 | AUAAUUACCUUUCUUUUCCTT |
| AL-DP-6907 | 330 | deltaEGFR | 14 | GAAAGGUAAUUAUGUGGUGTT | 15 | CACCACAUAAUUACCUUUCTT |
| AL-DP-6908 | 329 | deltaEGFR | 16 | AGAAAGGUAAUUAUGUGGUTT | 17 | ACCACAUAAUUACCUUUCUTT |
| AL-DP-6909 | 40 | deltaEGFR and wtEGFR | 18 | ACGGUGUGAGCGCCCGACGTT | 19 | CGUCGGGCGCUCACACCGUTT |
| AL-DP-6910 | 1150 | deltaEGFR and wtEGFR | 20 | ACAGAUCACGGCUCGUGCGTT | 21 | CGCACGAGCCGUGAUCUGUTT |
| AL-DP-6911 | 1156 | deltaEGFR and wtEGFR | 22 | CACGGCUCGUGCGUCCGAGTT | 23 | CUCGGACGCACGAGCCGUGTT |
| AL-DP-6912 | 117 | deltaEGFR and wtEGFR | 24 | CGACAGGCCACCUCGUCGGTT | 25 | CCGACGAGGUGGCCUGUCGTT |
| AL-DP-6913 | 1147 | deltaEGFR and wtEGFR | 26 | GUGACAGAUCACGGCUCGUTT | 27 | ACGAGCCGUGAUCUGUCACTT |
| AL-DP-6914 | 129 | deltaEGFR and wtEGFR | 28 | UCGUCGGCGUCCGCCCGAGTT | 29 | CUCGGGCGGACGCCGACGATT |
| AL-DP-6915 | 197 | deltaEGFR and wtEGFR | 30 | CCGUCCAGUAUUGAUCGGGTT | 31 | CCCGAUCAAUACUGGACGGTT |
| AL-DP-6916 | 1146 | deltaEGFR and wtEGFR | 32 | GGUGACAGAUCACGGCUCGTT | 33 | CGAGCCGUGAUCUGUCACCTT |
| AL-DP-6917 | 997 | wtEGFR | 34 | UGCCGCAAAUUCCGAGACGTT | 35 | CGUCUCGGAAUUUGCGGCATT |
| AL-DP-6918 | 683 | wtEGFR | 36 | GCGCCGUGCGGUUCAGCAATT | 37 | UUGCUGAACCGCACGGCGCTT |
| AL-DP-6919 | 999 | wtEGFR | 38 | CCGCAAAUUCCGAGACGAATT | 39 | UUCGUCUCGGAAUUUGCGGTT |
| AL-DP-6920 | 337 | wtEGFR | 40 | UGCCAAGGCACGAGUAACATT | 41 | UGUUACUCGUGCCUUGGCATT |
| AL-DP-6921 | 569 | wtEGFR | 42 | GAGGAAAUAUGUACUACGATT | 43 | UCGUAGUACAUAUUUCCUCTT |
| AL-DP-6922 | 668 | wtEGFR | 44 | AGGAAAUCCUGCAUGGCGCTT | 45 | GCGCCAUGCAGGAUUUCCUTT |
| AL-DP-6923 | 677 | wtEGFR | 46 | UGCAUGGCGCCGUGCGGUUTT | 47 | AACCGCACGGCGCCAUGCATT |
| AL-DP-6924 | 732 | wtEGFR | 48 | CCAGUGGCGGGACAUAGUCTT | 49 | GACUAUGUCCCGCCACUGGTT |

TABLE 3

Sequences of dsRNAs with stabilizing modifications tested for deltaEGFR and wtEGFR gene expression inhibiting activity

| Duplex name | Target position of 5' base of sense strand (see FIGS. 21A and 21B) | SEQ ID NO: | Sense strand sequence (5'-3') | SEQ ID NO: | Antisense strand sequence (5'-3') |
| --- | --- | --- | --- | --- | --- |
| AD-15416 | 320 | 50 | uGGAGGAAAAGAAAGGuAATsT | 51 | UuACCUUUCUUUUCCUCcATsT |
| AD-15417 | 321 | 52 | GGAGGAAAAGAAAGGuAAuTsT | 53 | AUuACCUUUCUUUUCCUCCTsT |
| AD-13373 | 322 | 54 | GAGGAAAAGAAAGGuAAuuTsT | 55 | AAUuACCUUUCUUUUCCUCTsT |
| AD-13374 | 319 | 56 | cuGGAGGAAAAGAAAGGuATsT | 57 | uACCUUUCUUUUCCUCcAGTsT |
| AD-13375 | 323 | 58 | AGGAAAAGAAAGGuAAuuATsT | 59 | uAAUuACCUUUCUUUUCCUTsT |
| AD-15418 | 324 | 60 | GGAAAAGAAAGGuAAuuAuTsT | 61 | AuAAUuACCUUUCUUUUCCTsT |
| AD-15419 | 325 | 62 | GAAAGGuAAuuAuGuGGuGTsT | 63 | cACcAcAuAAUuACCUUUCTsT |
| AD-15420 | 329 | 64 | AGAAAGGuAAuuAuGuGGuTsT | 65 | ACcAcAuAAUuACCUUUCUTsT |
| AD-16177 | 997 | 66 | uGccGcAAAuuccGAGAcGTsT | 67 | CGUCUCGGAAUUUGCGGcATsT |
| AD-13376 | 683 | 68 | GcGccGuGcGGuucAGcAATsT | 69 | UUGCUGAACCGcACGGCGCTsT |
| AD-16178 | 999 | 70 | ccGcAAAuuccGAGAcGAATsT | 71 | UUCGUCUCGGAAUUuGCGGTsT |
| AD-16179 | 337 | 72 | uGccAAGGcAcGAGuAAcATsT | 73 | UGUuACUCGUGCCUUGGcATsT |
| AD-13377 | 569 | 74 | GAGGAAAuAuGuAcuAcGATsT | 75 | UCGuAGuAcAuAUUUCCUCTsT |
| AD-16180 | 668 | 76 | AGGAAAuccuGcAuGGcGcTsT | 77 | GCGCcAUGcAGGAUUUCCUTsT |
| AD-13378 | 677 | 78 | uGcAuGGcGccGuGcGGuuTsT | 79 | AACCGcACGGCGCcAUGcATsT |
| AD-16181 | 732 | 80 | ccAGuGGcGGGAcAuAGucTsT | 81 | GACuAUGUCCCGCcACUGGTsT |

TABLE 4

Summary of the western blot results of the knock-down of delta or wtEGFR expression after transfection of non-stabilized or stabilized siRNAs.

| Unmodified siRNA | Specificity | U87-deltaEGFR | U87-wtEGFR | Durability (days) | Modified siRNA | U87-deltaEGFR | U87-wtEGFR | Durability (days) |
| --- | --- | --- | --- | --- | --- | --- | --- | --- |
| AL-DP-6901 | deltaEGFR | + | − | 7-10 | AD-15416 | + | − | 7-12 |
| AL-DP-6902 | deltaEGFR | + | − | 7-10 | AD-15417 | + | − | 7-12 |
| AL-DP-6903 | deltaEGFR | + | − | 7-10 | AD-13373 | + | x | x |
| AL-DP-6904 | deltaEGFR | + | − | x | AD-13374 | + | x | 5-7 |
| AL-DP-6905 | deltaEGFR | + | − | 10-14 | AD-13375 | + | − | 5-7 |
| AL-DP-6906 | deltaEGFR | + | + | x | AD-15418 | + | − | 7-12 |
| AL-DP-6907 | deltaEGFR | + | x | x | AD-15419 | + | x | x |
| AL-DP-6908 | deltaEGFR | − | x | x | AD-15420 | + | x | x |
| AL-DP-6909 | both | +/− | + | x | none | na | na | na |
| AL-DP-6910 | both | + | − | x | none | na | na | na |
| AL-DP-6911 | both | − | − | x | none | na | na | na |
| AL-DP-6912 | both | − | − | x | none | na | na | na |
| AL-DP-6913 | both | + | + | 7-10 | none | na | na | na |
| AL-DP-6914 | both | − | − | x | none | na | na | na |
| AL-DP-6915 | both | + | + | x | none | na | na | na |
| AL-DP-6916 | both | + | + | 7-10 | none | na | na | na |
| AL-DP-6917 | wtEGFR | x | +/− | x | AD-16177 | − | +/− | x |
| AL-DP-6918 | wtEGFR | − | + | x | AD-13376 | x | +/− | x |
| AL-DP-6919 | wtEGFR | − | + | x | AD-16178 | − | + | x |
| AL-DP-6920 | wtEGFR | − | + | 7-10 | AD-16179 | − | + | x |
| AL-DP-6921 | wtEGFR | − | + | 7-10 | AD-13377 | − | + | ≥7 |
| AL-DP-6922 | wtEGFR | x | − | x | AD-16180 | x | − | x |

TABLE 4-continued

Summary of the western blot results of the knock-down of delta or wtEGFR expression after transfection of non-stabilized or stabilized siRNAs.

| Unmodified siRNA | Specificity | U87-deltaEGFR | U87-wtEGFR | Durability (days) | Modified siRNA | U87-deltaEGFR | U87-wtEGFR | Durability (days) |
|---|---|---|---|---|---|---|---|---|
| AL-DP-6923 | wtEGFR | − | + | x | AD-13378 | x | − | x |
| AL-DP-6924 | wtEGFR | x | − | x | AD-16181 | x | − | x |

− = no reduction of expression
+ = reduction of expression
+/− = small reduction of expression
x = not determined
na = not available

Example 9 siRNAs Specific for IL-6 Reduced Tumor Growth In Vivo after Subcutaneous Injection of U87Δ Cells Methods In Vitro siRNA Screening:

U87-ΔEGFR (Nishikawa et al, PNAS 91: 7727-7731, 1994) cells over-express the IL-6 cytokine, and the importance of IL-6 secretion was underscored by demonstrating that the in vivo growth of wtEGFR-expressing cells could be enhanced when mixed with parental glioma cells engineered to overexpress IL-6 (see Example 10 below).

To further test the role of IL-6 in enhanced cell proliferation, 24 stabilized siRNAs were designed to be specific to IL-6 (AD-15637 to AD-15660) and were synthesized. The sequences of the siRNAs and their target position on the IL-6 mRNA (GenBank Accession No. NM_000600.2, version Jan. 4, 2009) (FIG. 11) are provided in Table 5.

Cells were seeded in 24 well plates at 48,000 cells per well in DMEM medium (Cellgro) supplemented with 10% fetal bovine serum and L-Glutamine. The following day, siRNAs were transfected at 100 nM using Lipofectamine™ 2000 (Invitrogen™) and OptiMEM® (Gibco™). Cells non-transfected as well as transfected with an siRNA specific for GFP or Luciferase were included as negative controls. Forty-eight hours after transfection, the medium was changed to DMEM-serum-free supplemented with penicillin/streptomycin and L-Glutamine after washing the cells with serum-free medium. After twenty-four hours of serum-starvation, supernatants were collected, centrifuged to remove cell debris, and either analyzed immediately or frozen at −80° C. Quantification of IL-6/IL-8 in supernatants was assessed by ELISA. Briefly, 96-well plates (MaxiSorp, Nunc) were coated overnight at room temperature with the capture antibody diluted in PBS. The following day, the plates were blocked in blocking buffer composed of PBS containing 1% BSA and 5% sucrose. The standards (recombinant human IL-6 and IL-8) and the samples were diluted in diluent buffer (1×TBS, 0.5% BSA, 0.05% Tween-20) and incubated 2 hours at room temperature. The plates were then washed with PBS 0.05% Tween-20 and incubated with the biotinylated detection antibody and then with streptavidin-HRP (Biosource) both diluted in diluent buffer. The HRP activity was determined by using Tetramethylbenzidine (Sigma) as substrate. The enzymatic reaction was stopped with 1 N sulfuric acid and the absorbance was measured at 450 nm with wavelength correction set to 540 nm using a Tecan Genios Pro microplate reader. The absorbance readings were converted using a four parameter logistic curve.

In Vitro Specificity Test:

To exclude that any reduction in the cytokine synthesis was caused by off-target effects of the siRNAs, the concentration of both IL-6 and IL-8 was measured in the samples where an siRNA was found to have a strong effect on the expression of IL-6, and compared to non-transfected cells as well as cells transfected with an siRNA against GFP or Luciferase.

In Vitro Dose-Response Analysis:

siRNAs determined to be specifically able to knock-down the secretion of IL-6 were tested again in U87-ΔEGFR to determine the minimal effective dose to achieve cytokine secretion knock-down. Cells were seeded in 24 well plates at 48,000 cells per well and siRNAs were transfected the following day at 100, 20, 4 and 0.8 nM concentrations using Lipofectamine™ 2000. Forty-eight hours after transfection the medium was changed to serum-free medium and twenty-four hours later the supernatants were collected and centrifuged as described previously. Cells non-transfected as well as transfected with an siRNA against GFP or Luciferase were included as negative controls. IL-6 or IL-8 secretion was analyzed by ELISA.

In Vitro Durability Test:

siRNAs determined to be robust in the ablation of IL-6 secretion, when transfected at low concentration, were tested for suppression durability using U87-ΔEGFR cells. Cells were seeded in 24 well plates at 48,000 cells per well and siRNAs were transfected the following day at 25 nM concentration using Lipofectamine™ 2000. Supernatants were collected at days 3, 7, and 11 or 14 days post-transfection (in each case after 24 hours serum-starvation). Cells non-transfected as well as transfected with an siRNA against GFP or Luciferase were included as negative controls. IL-6 secretion was analyzed by ELISA.

In Vitro Proliferation Test:

Cells were seeded in 24 well plates at 48,000 cells per well and siRNAs were transfected the following day at 25 nM concentration using Lipofectamine™ 2000. 48 hours after transfection the cells were trypsinized, counted, and seeded at the same density in larger dishes to allow them to grow. The cell proliferation was evaluated by counting the cells at day 4 and at day 6-8 as indicated. Three independent samples were counted for each treatment/time point.

Ex Vivo Experiments:

To determine the effect of specific IL-6 knock-down on tumorigenicity, U87-ΔEGFR cells were transfected with the different siRNAs (AD-15644 and AD-15660) and then injected subcutaneously into nude mice. Briefly, $1.3 \times 10^6$ cells were seeded in 10 cm plates and one day after they were transfected either with a control siRNA or with a specific siRNA at the concentration of 25 nM with Lipofectamine™ 2000. The following day, the medium was changed and cells were split into larger dishes. Transfected U87-ΔEGFR cells were injected subcutaneously into the right flank of Nu/Nu mice using a 1 ml syringe with a 26G needle. $5 \times 10^5$ cells resuspended in 100 μl of PBS were injected into each mouse. Tumor volume was measured starting at day 5 after injection and was calculated using the formula $0.5 \times L \times W^2$. Mice were euthanized according to our animal protocol when tumor volume reached 1500 mm$^3$.

In Vivo siRNA Delivery:

One million cells of U87-wtEGFR mixed with U87-ΔEGFR in a ratio 90:10% respectively were injected subcutaneously into 4 to 5 weeks-old female nude mice. Treatment of tumors was started after 13 days when the tumor volume reached approximately 80 mm3. JetPEI/siRNA complexes were prepared following manufacturer instructions (Polyplus Transfection, Illkirch, France) in 5% Glucose at N/P ratio of 15 and 70 μl of the complex was injected intratumorally at a dose of 10 μg siRNA/mouse every two days. Tumor volumes were measured every second day from the commencement of siRNA delivery through day 21 of treatment.

Results

Figure 12A:
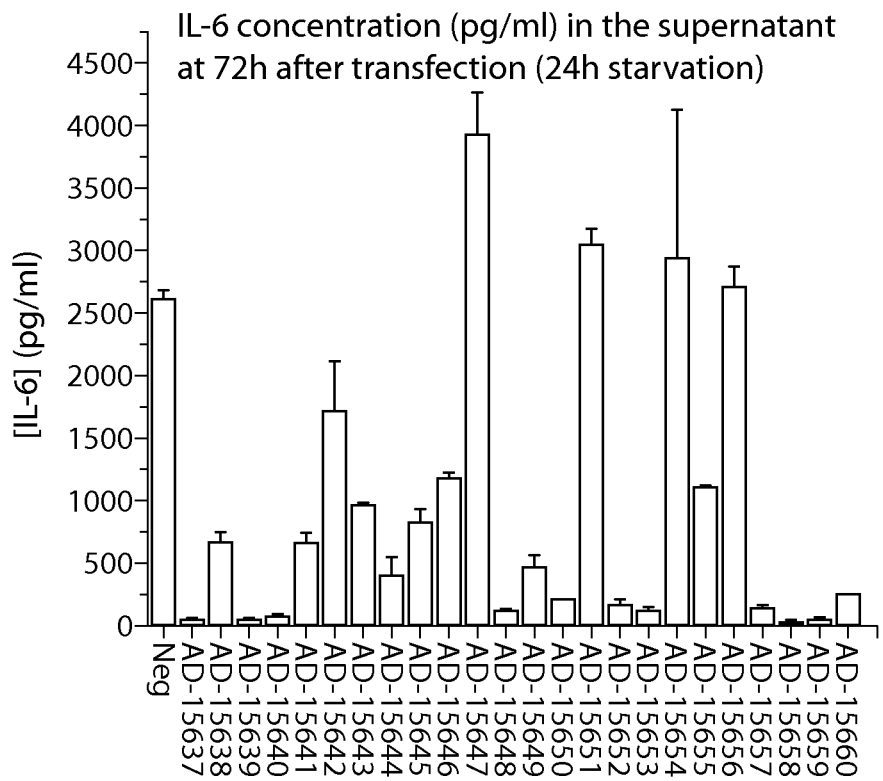
FIGS. 12A and 12B are graphs showing screening analysis of stabilized siRNAs designed for IL-6 by ELISA.
Figure 12B:
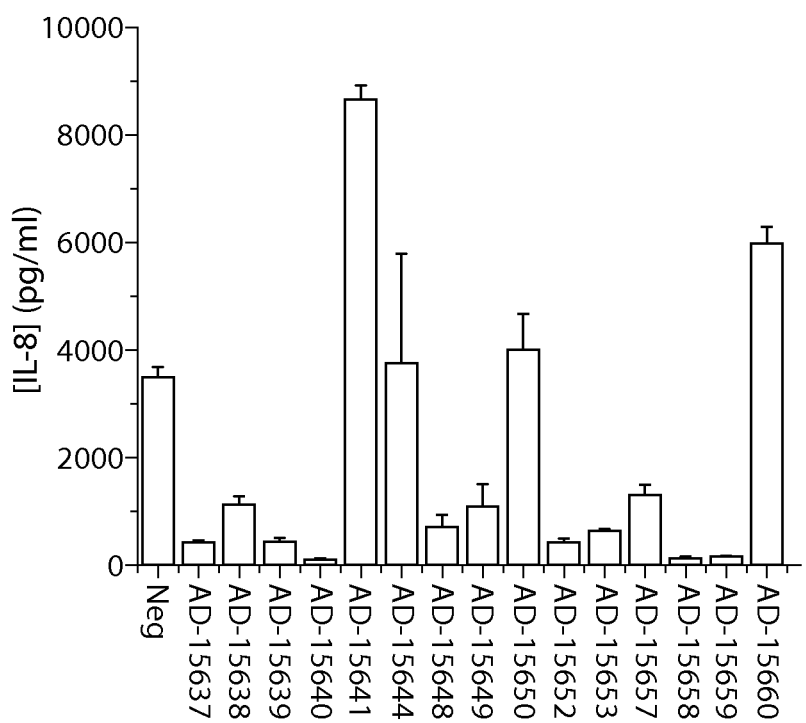

In Vitro siRNA Screening (Table 9):

ELISA analysis demonstrated that 20 of 24 siRNAs designed against IL-6 were capable of reducing IL-6 secretion in U87-ΔEGFR cells when tested at 100 nM (Table 9, and FIGS. 12A and 12B). Only siRNAs AD-15647, AD-15651, AD-15654, and AD-15656 were unable to reduce IL-6 secretion in U87-ΔEGFR cells (FIG. 12A). The strongest effect was obtained with AD-15658 (99.09%), and the weakest with AD-15642 (34.1%), with an average 82.4% reduction compared with cells transfected with the control siRNA. IL-8 concentration was tested in the 15 samples (FIG. 12B) where strongest reduction of IL-6 secretion was observed. IL-8 production was significantly reduced in 11 of the analyzed samples. In one case (AD-15641) there was a significant increase in IL-8 secretion. Two siRNAs designed against IL-6 (AD-15644, AD-15650), showed no significant effect on the IL-8 secretion in U87-ΔEGFR cells demonstrating specificity for IL-6. AD-15660 caused a moderate increase in IL-8 production.

In Vitro Dose-Response Analysis:

The five siRNAs that showed the least non-specific effects were selected, transfected into U87-ΔEGFR cells in serial 1:5 dilutions starting at 100 nM and compared to a control siRNA at 100 nM.

Figure 13A:
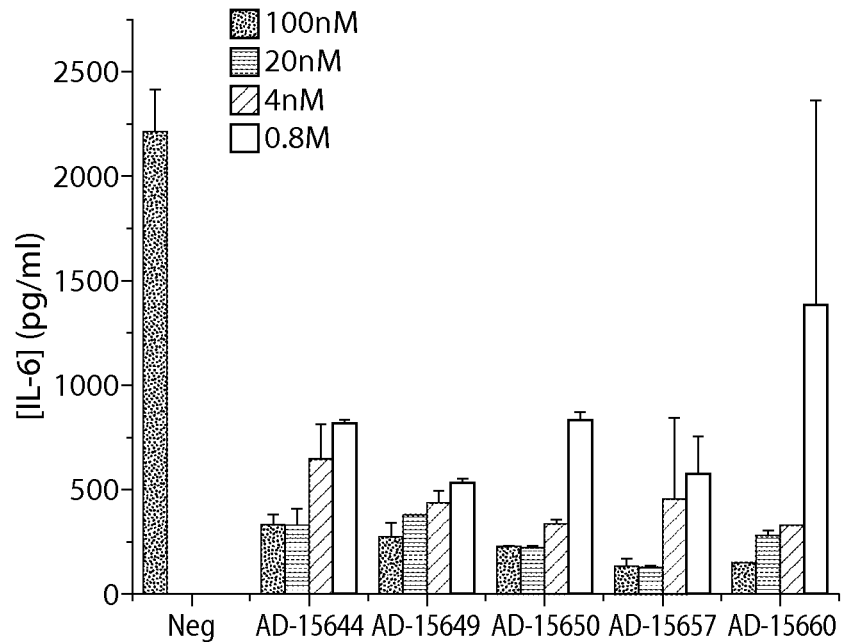
FIGS. 13A and 13B are graphs showing dose-response analysis of stabilized IL-6 siRNAs. Quantification of secreted IL-6 (FIG. 13A) and IL-8 (FIG. 13B) in supernatants from U87-ΔEGFR cells transfected with 100, 20, 4, and 0.8 nM of different IL-6 siRNAs was performed by ELISA. Values are mean±SE of 2 independent samples. ("Neg": siRNA targeting an irrelevant sequence).
Figure 13B:
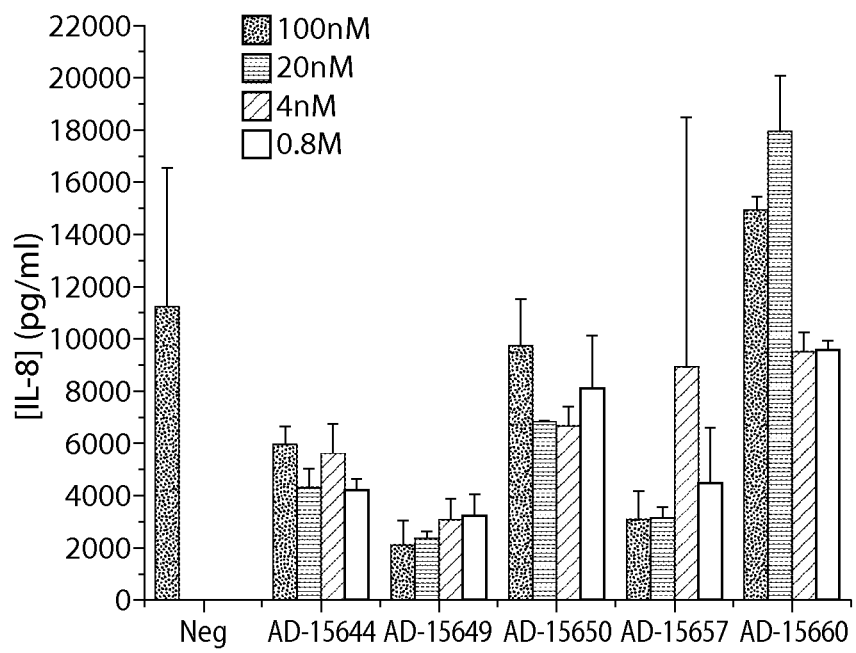

ELISA analysis demonstrated that the 5 IL-6-specific siRNAs tested (AD-15644, -15649, -15650, -15657 and -15660) reduced significantly the secretion of IL-6 when transfected into U87-ΔEGFR cells at doses as low as 0.8 nM (FIG. 13A). The concentration of IL-8 was also measured in these samples (FIG. 13B) showing that siRNAs AD-15650 and AD-15660 caused the least significant reduction in IL-8 secretion when compared to control siRNA.

Figure 14:
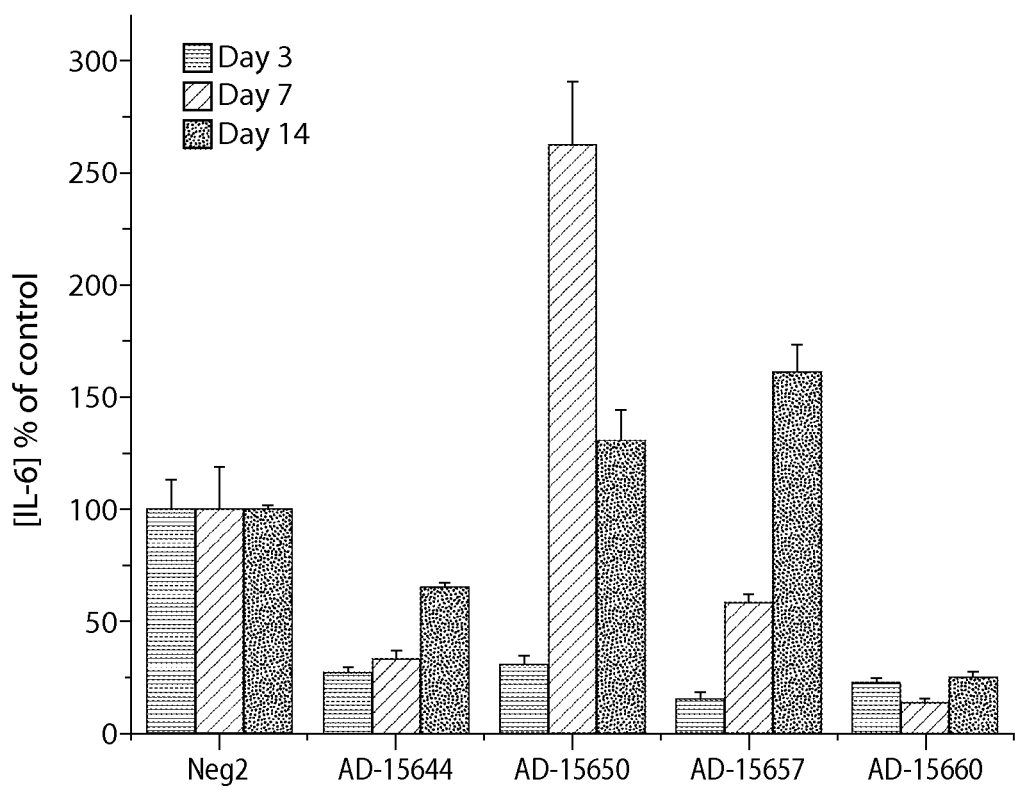
FIG. 14 is a graph illustrating durability analysis of stabilized IL-6 siRNAs. Quantification of secreted IL-6 in supernatants of U87-ΔEGFR cells at different days after transfection with the siRNAs was performed by ELISA. ("Neg2": siRNA targeting an irrelevant sequence).

In Vitro Durability Test:

ELISA analysis demonstrated that two out of four IL-6-specific siRNAs analyzed (AD-15644 and AD-15660) were capable of maximally reducing IL-6 secretion in U87-ΔEGFR cells as far as day 7 after siRNA transfection. At day 14 these two siRNAs were still able to suppress IL-6 expression. siRNA AD-15650 was capable of suppression of IL-6 secretion only until day three, and AD-15657 only until day 7 (FIG. 14).

In Vitro Proliferation Test:

The proliferation of U87-ΔEGFR transfected with siRNAs AD-15644, -15650, and -15660 was monitored in vitro for 6 days, and compared with cells non transfected or transfected with a control siRNA. Only AD-15644 and AD-15660 had no effect on cell proliferation, while AD-15650 almost completely blocked cell proliferation in vitro.

Figure 15A:
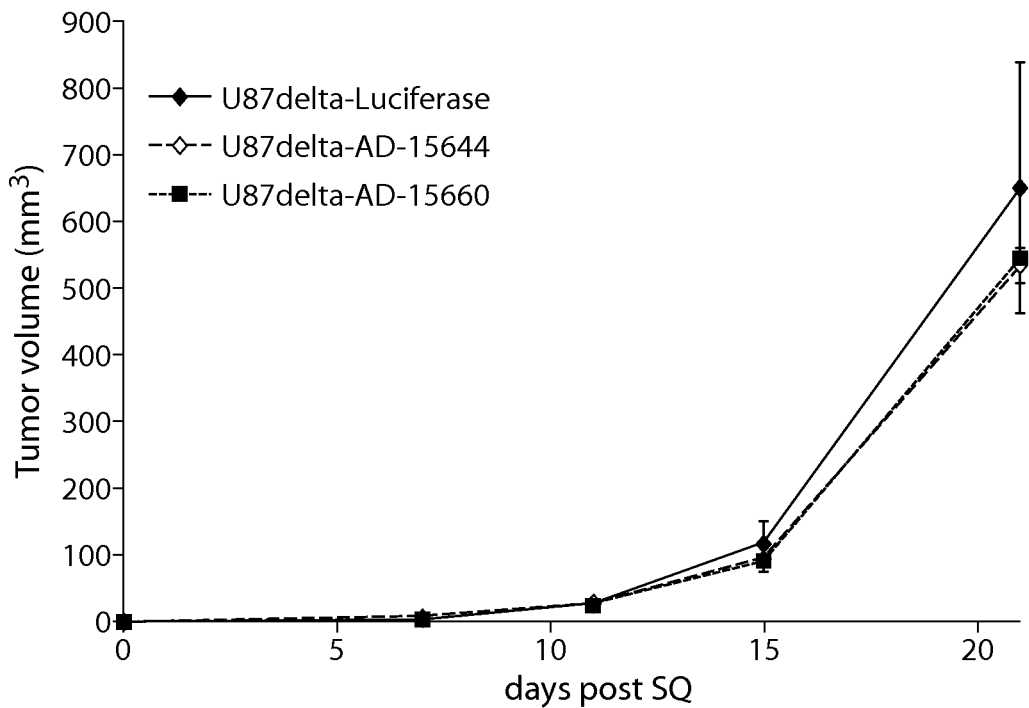
FIGS. 15A and 15B are two graphs illustrating ex vivo tumorigenicity test of IL-6-specific stabilized siRNAs. The graphs show tumor growth kinetics (top) and tumor volume at the end of the experiment (bottom) after injection into nude mice of U87-deltaEGFR cells transfected with stabilized siRNAs against luciferase or GFP, IL-6 (AD-15644 and AD-15660). The experimental group included 6 animals. Data are shown as mean±SE.
Figure 15B:
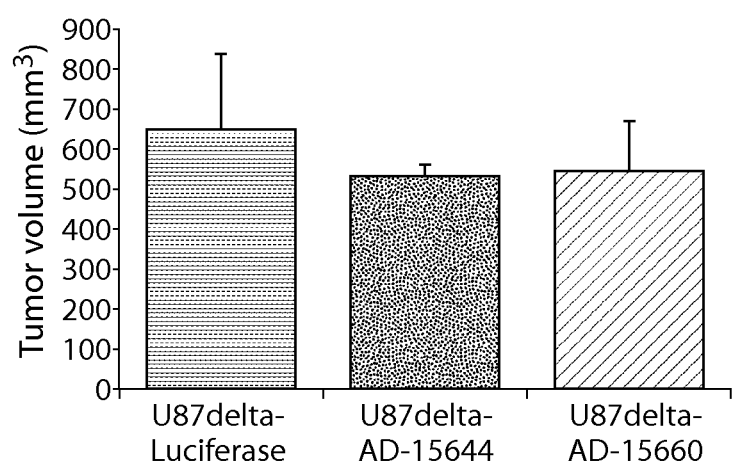

Ex Vivo Experiments:

U87-ΔEGFR cells were transfected with 25 nM siRNA and injected subcutaneously into nude mice. Treatment with siRNAs AD-15644 and AD-15660 resulted in no substantial reduction of U87-ΔEGFR tumor growth (FIGS. 15A and 15B). As a negative control, cells non transfected or transfected with an irrelevant Luciferase siRNA were included in the study. In both groups, substantial tumor growth occurred.

Figure 16A:
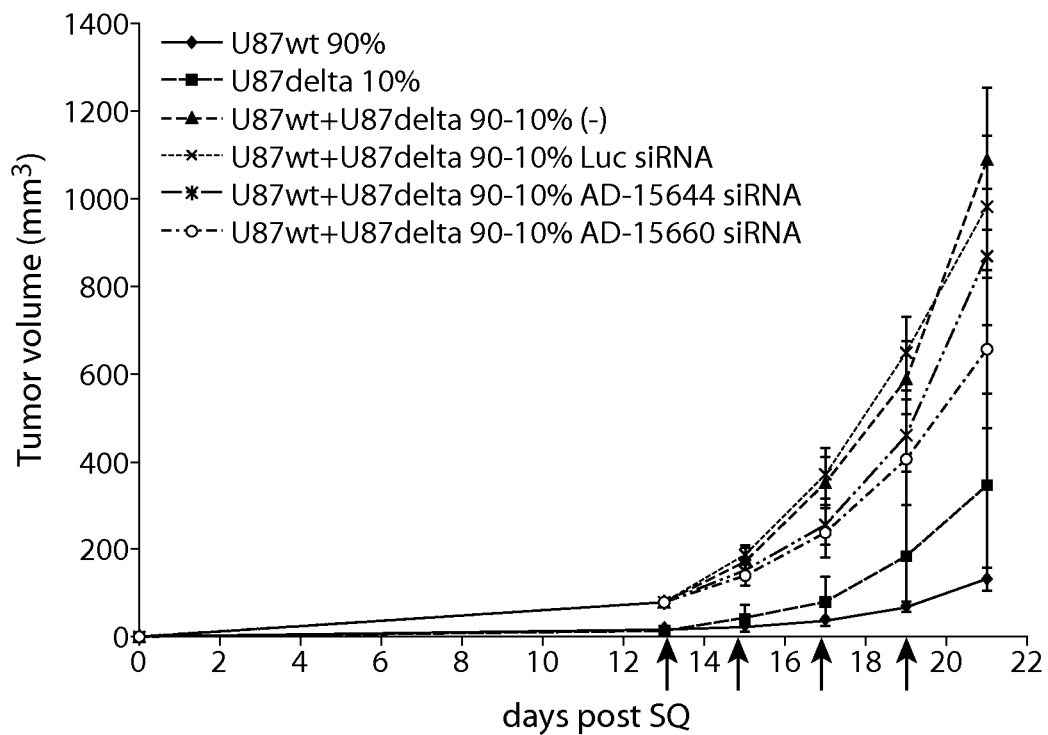
FIGS. 16A and 16B are graphs illustrating the efficacy of in vivo delivery of IL-6 siRNAs (AD-15644 and AD-15660). Tumor growth kinetics (FIG. 11A) and tumor volume at the end of the experiment (FIG. 11B) was reduced in tumors treated with IL-6 specific siRNA AD-15660, but not in tumors treated with a siRNA against luciferase. Each group included 4 animals. Data are shown as mean±SE.
Figure 16B:
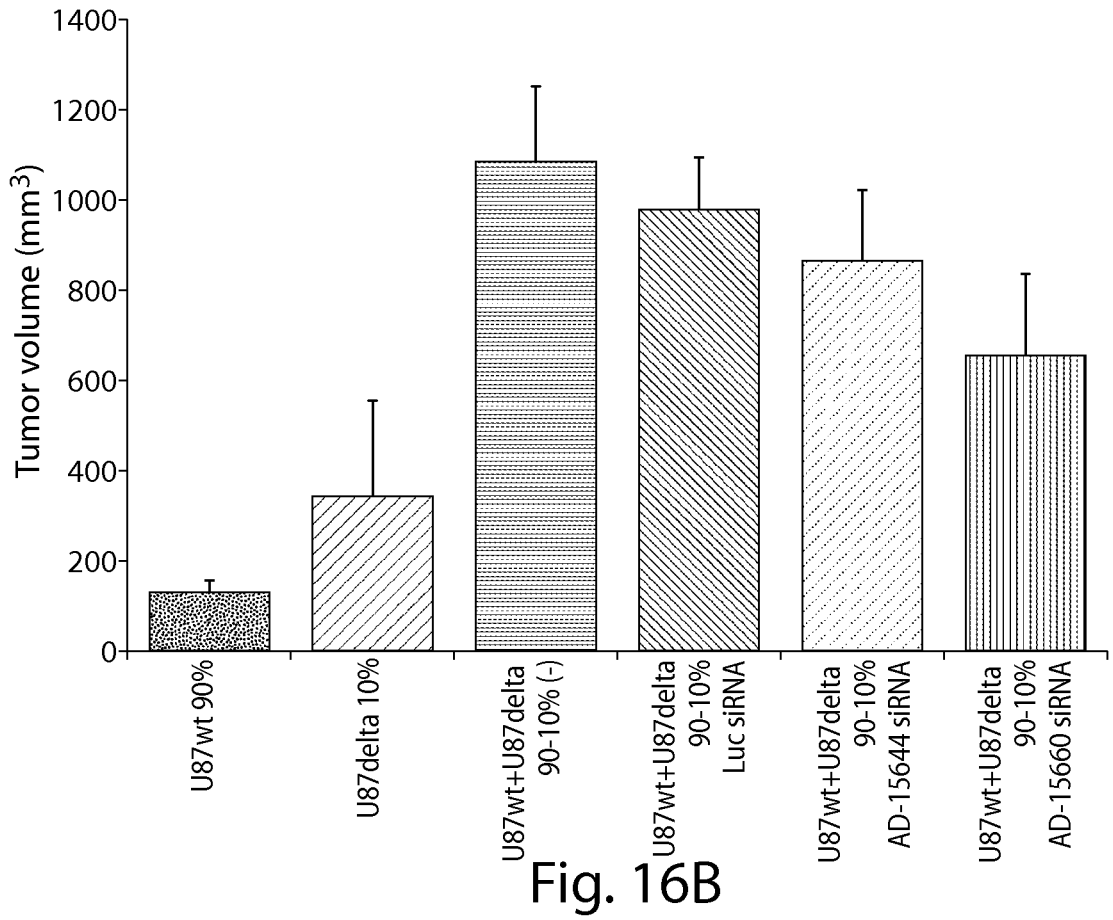

In Vivo siRNA Delivery:

Two siRNAs (AD-15644 and AD-15660) that demonstrated specificity for IL-6 and showed durable, low dose knock-down were chosen for in vivo studies. Nude mice were injected subcutaneously with $1 \times 10^6$ U87wt or U87Δ cells or with U87wt+U87Δ (90:10%) (FIGS. 9A and 9B) and monitored until tumors reached 80 mm$^3$ whereupon ten micrograms of AD-15644 or AD-15660 siRNA against IL-6 or an siRNA against Luciferase gene were injected intratumorally every two days. Tumor growth kinetics (FIG. 16A) and tumor volume (FIG. 16B) at the end of the experiment was reduced in tumors treated with IL-6 specific siRNA AD-15660, but not in tumors treated with an siRNA against luciferase or with AD-15644 siRNA. These results illustrate that the emergence of the ΔEGFR oncogene during gliomagenesis not only conveys a cell intrinsic growth potential but also establishes a cell extrinsic potentiation loop to neighboring cells expressing the amplified antecedent genetic lesion. These results also illustrate a potential therapeutic use of IL-6 siRNA to inhibit the tumor enhancement conferred by ΔEGFR on cells over-expressing wtEGFR and demonstrate a role for this cytokine in driving glioma heterogeneity.

Example 10

IL-6 Enhances Heterogeneous Tumorigenic Growth

Figure 17A:
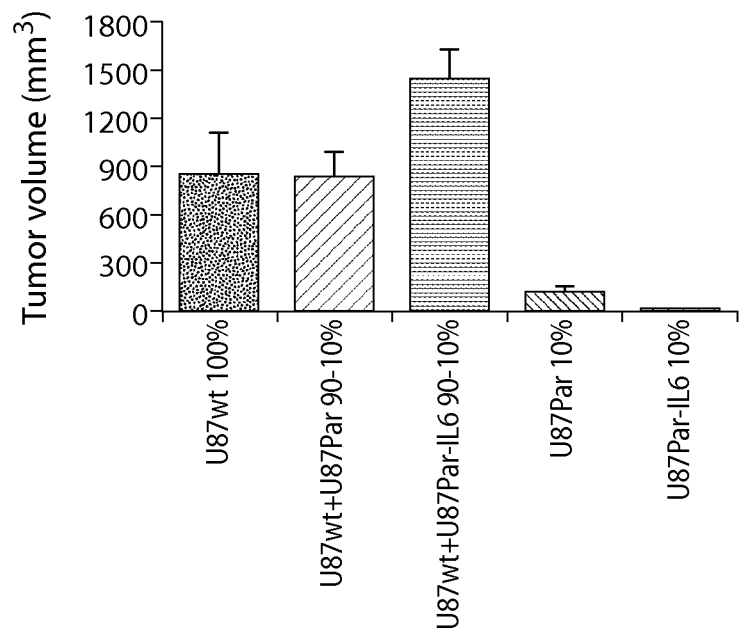
FIGS. 17A and 17B are graphs illustrating tumor volume (A) and tumor growth kinetics (B) after subcutaneous injection of the indicated cell types into nude mice. Tumor volume (FIG. 17A) was assayed at day 32 after injection.
Figure 17B:
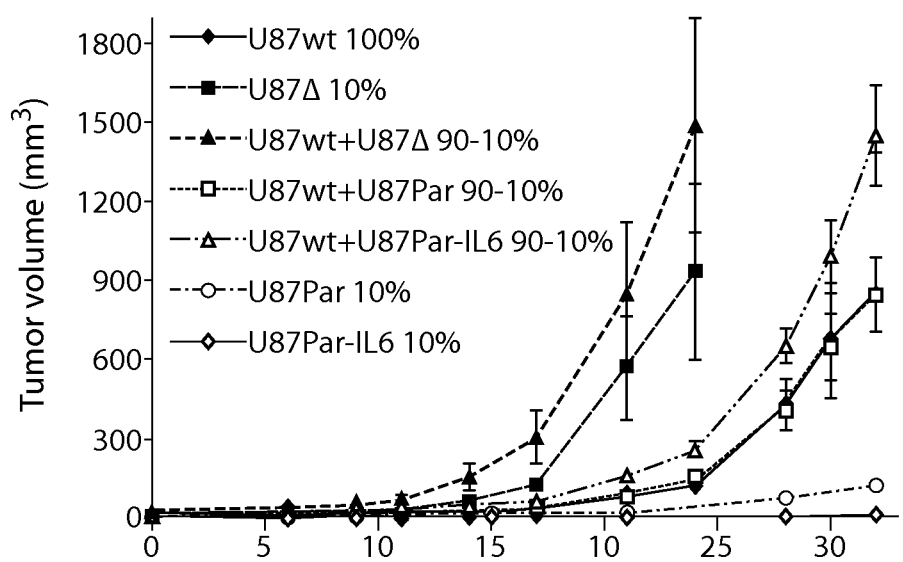
Figure 18:
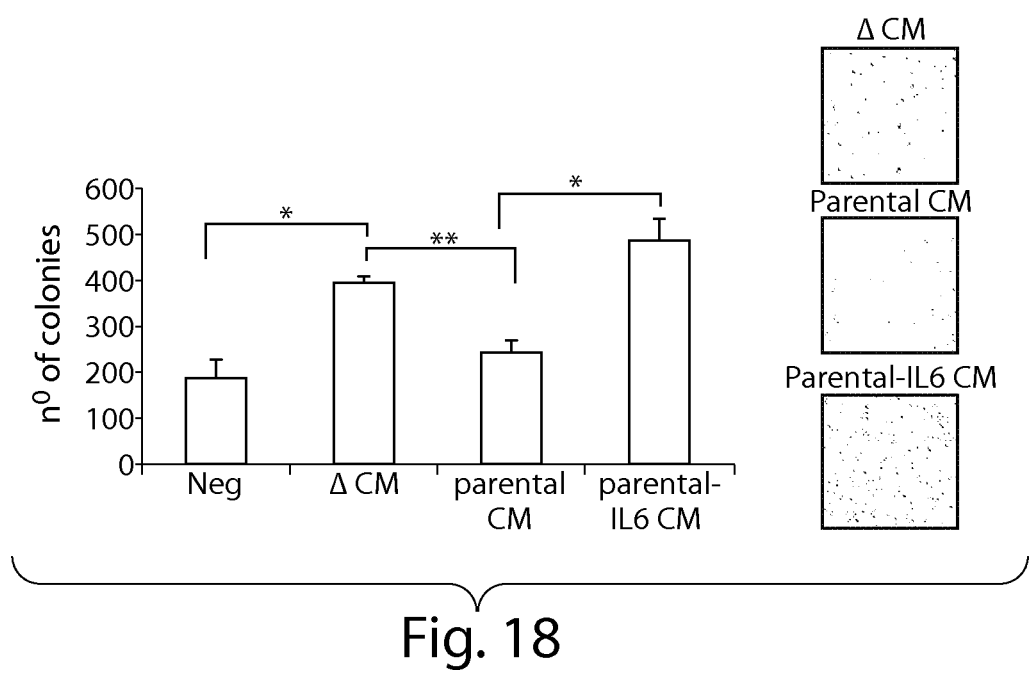
FIG. 18 is a graph illustrating quantification of soft agar colony formation of U87wt colonies formed after treatment with normal media (Neg), or U87Δ (ΔCM (conditioned medium)), U87 Par (parental CM), or U87 Par-IL6 (parental-IL6) CM (*: p<0.05; ** p<0.001).

To determine whether the over-expression of IL-6 was a mediator of U87wt tumor enhancement through its secretion from U87Δ cells, U87 Parental cells, which lack the ability to enhance U87wt tumor growth (FIG. 1A), were engineered to over-express IL-6 (U87 Par-IL6). U87wt alone or mixed with U87Δ, U87 Parental or U87 Par-IL6 were injected subcutaneously into nude mice ($1 \times 10^6$ total cells) at a ratio of 90:10% (FIG. 17A) and resultant tumor volumes were measured over 32 days. As controls, mice were injected with 10% of the total cell number ($1 \times 10^5$ cells) of U87Δ, U87 Parental and U87 Par-IL6 cells. As shown in FIGS. 17A and 17B, U87 Par-IL6 did not grow faster than U87 Parental. When they were mixed with U87wt cells, tumor growth kinetics were much faster for the U87wt+U87 Par-IL6 mixture than for U87wt+U87 Par demonstrating a paracrine tumor enhancement effect mediated by IL-6 secretion in these composite tumors. Even though U87 Parental and U87 Par-IL6 grew more slowly than U87Δ, we observed a potent tumor enhancement when U87wt were injected with U87 Par-IL6 with tumor volumes being nearly double that of U87wt tumors by the end of the experiment (FIG. 17B). In accordance with the previous results, CM generated from U87 Parental-IL6 was able to potently enhanced U87wt colony formation in the in vitro soft agar colony formation assays (FIG. 18). U87Parental-IL6 CM was able to enhance U87wt colony formation with the same efficiency as U87Δ CM (p>0.05). In contrast, U87 Parental CM was unable to enhance colony formation, and no significant differences were found when U87wt cells were treated with U87 Parental or normal media (p>0.05).

Figure 19:
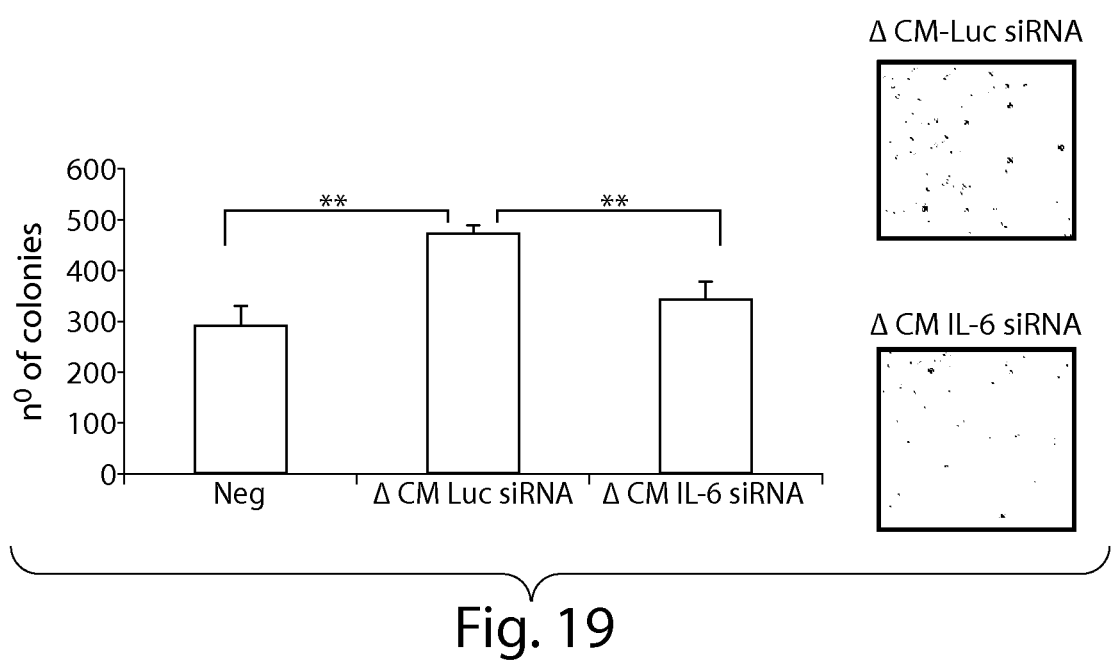
FIG. 19 is a graph illustrating quantification of soft agar colony formation of U87wt colonies formed after treatment with normal media (negative control, Neg), or with U87Δ cell CM untreated (ΔCM) or pretreated with IL-6 neutralizing antibody (ΔCM+IL-6 Ab) (**: p<0.001).

Example 11 siRNA-Mediated Reduction of U87Δ-Produced IL-6 Inhibits Soft Agar Colony Formation of U87 Wt Cells Two siRNAs targeting IL-6 (AD-15644 and AD-15660) were studied in an in vitro soft agar colony formation assay (FIG. 19). $5 \times 10^5$ U87Δ cells, U87Δ cells transfected with 25 nM luciferase siRNA or U87Δ cells transfected with 25 nM of a mixture of AD-15644 and AD-15660 (12.5 nM each) were plated in 10 cm$^2$ dishes with 10 ml DMEM supplemented with 10% FBS, penicillin/streptomycin and L-Glutamine, and media was collected after 48 hours. Conditioned medium (CM) or normal medium was filtered and used in the upper layer of agar as well as on top of the agar. Briefly, the bottom layer of agar was prepared by mixing equal volumes of 1.2% agar (USB Corporation) and 2×DMEM/20% FBS solutions. Two ml of the resulting 0.6% agar/1×DMEM/10% FBS solution was added to each well of 6 well/plates and let to solidify at room temperature. The upper layer containing $2.5 \times 10^3$ U87wt cells was prepared by mixing equal volumes of 1.2% agar, 2×DMEM/20% FBS and conditioned media or normal media. Plates were kept at room temperature until top agar solidified and treatment media was added on top of the agar. Plates were placed at 37° C./5% CO$_2$ for three weeks. Once a week, media on top of the agar was replaced with fresh media. Every treatment was performed in triplicate. After three weeks, plates were stained with 0.005% crystal violet solution and pictures were taken using a digital camera illuminated with white light. Colonies were counted using Image Pro-Analyzer 6.2 Software.

CM generated from U87Δ cells transfected with siRNA against the irrelevant luciferase gene (Δ CM Luc siRNA) resulted in a significant increase in colony number (** p<0.01). In contrast, CM generated from U87Δ cells transfected with a mixture of the IL-6 siRNAs AD-15644 and AD-15660 (Δ CM IL-6 siRNA) resulted in a reduction in soft agar colony number to levels comparable to normal growth media. These results demonstrate that IL-6 produced from U87Δ cells has an important role in the promotion of U87wt cell proliferation, and that siRNAs targeting IL-6 inhibit this promotion of U87wt cell proliferation.

Example 12 siRNA-Mediated Reduction of U87Δ-Produced IL-6 Inhibits Tumor Growth Enhancement of U87wt Cells To study the effect of IL-6 secretion from U87Δ cells on tumor growth enhancement, U87Δ cells were transfected with a 25 nM dose of a combination of IL-6 siRNAs AD-15644 and AD-15660, or an siRNA against the irrelevant luciferase gene as a negative control. $1.3 \times 10^6$ U87Δ cells were seeded in 10 cm plates and the following day were transfected using Lipofectamine™ 2000 (Invitrogen) and a mixture of IL-6 siRNAs AD-15644 and AD-15660 at a concentration of 12.5 nM each, or an siRNA against the luciferase gene at a concentration of 25 nM. After 18 hours of transfection, the media was changed and cells were partitioned into larger plates. The transfected U87Δ cells ($10^5$ cells per mouse, 10%) were injected subcutaneously into nude mice alone or mixed with U87wt cells ($9 \times 10^5$ cells per mouse, 90%). Tumors were measured starting at day 5 after injection and volumes were calculated as described above.

Figure 20A:
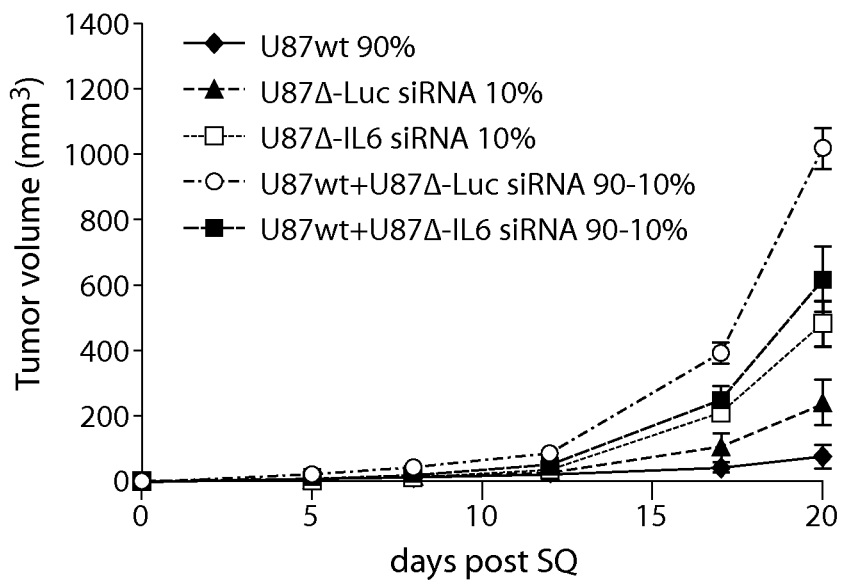
FIGS. 20A and 20B are graphs illustrating tumor growth kinetics (A) and tumor volume at day 20 (B) after subcutaneous injection of U87wt, U87Δ-Luc siRNA or U87Δ-IL6 siRNA cells only, or U87wt cells mixed with U87Δ-Luc siRNA or U87Δ-IL6 siRNA cells at a ratio of 90:10.
Figure 20B:
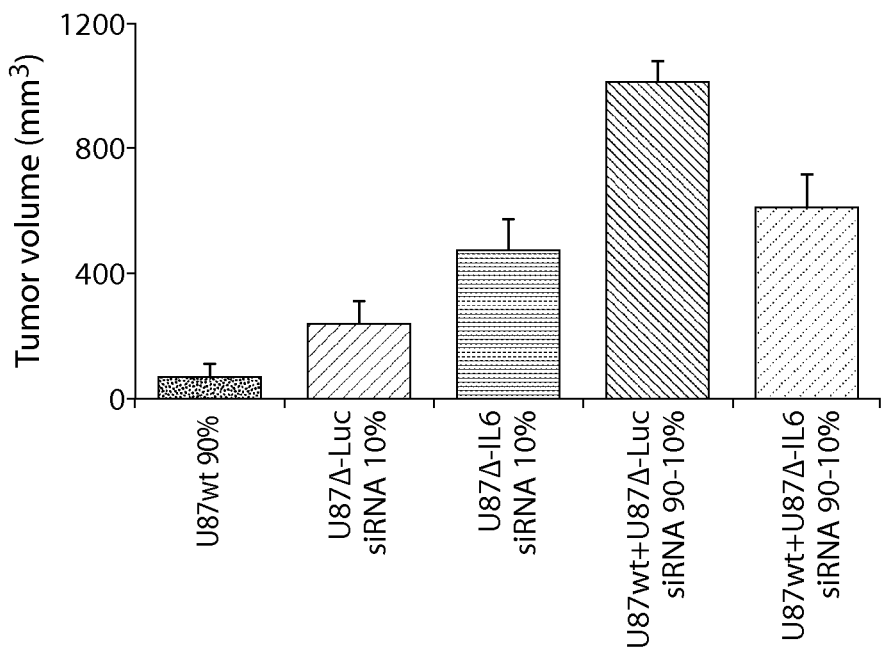

As shown in FIGS. 14A and 14B, there was no significant difference in tumor volume between U87Δ cells transfected with IL-6 siRNAs or with luciferase siRNA when injected alone (p>0.05). However, tumor volume was significantly reduced when U87wt cells were mixed with U87Δ cells transfected with IL-6 siRNAs compared to U87Δ cells transfected with luciferase siRNA (p<0.05). Tumor volumes obtained at the end of the experiment when U87Δ cells were transfected with IL-6 siRNAs and mixed with U87wt were similar to the sum of the volumes obtained after injection of U87wt (90%) and U87Δ (10%) indicating a reduction in the proliferation enhancement of U87wt cells induced by U87Δ cells (FIGS. 20A and 20B). This reduction of U87wt contribution to tumor volume was confirmed when we analyzed the cell composition by flow cytometry. A significant reduction in the proportion of U87wt cells was detected in mixed tumors where IL-6 was knocked-down (41.8±2.73% U87wt cells in U87wt+ U87Δ-Luciferase siRNA tumors vs. 32.87±2.28% U87wt cells in U87wt+U87Δ-IL6 siRNA tumors). These results illustrate a potential therapeutic use of IL-6 siRNAs to inhibit the tumor enhancement conferred by ΔEGFR on cells overexpressing wtEGFR.

TABLE 5

Modified siRNAs targeting IL-6.

| Duplex Name | Target position of 5' base of sense strand (see FIG. 11) | S Oligo Name | SEQ ID NO: | Sense (S) Oligo Sequence (5' to 3') | AS Oligo Name | SEQ ID NO: | Antisense (AS) Oligo Sequence (5' to 3') |
|---|---|---|---|---|---|---|---|
| AD-15637 | 803 | 25860 | 82 | AAAAGuAuGAGcGuuAGGAdTsdT | 25861 | 83 | UCCuAACGCUcAuACUUUUdTsdT |
| AD-15638 | 223 | 25862 | 84 | uGAcAAAcAAAuucGGuAcdTsdT | 25863 | 85 | GuACCGAAUUUGUUUGUcAdTsdT |
| AD-15639 | 802 | 25864 | 86 | uAAAAGuAuGAGcGuuAGGdTsdT | 25865 | 87 | CCuAACGCUcAuACUUUUAdTsdT |
| AD-15640 | 804 | 25866 | 88 | AAAGuAuGAGcGuuAGGAcdTsdT | 25867 | 89 | GUCCuAACGCUcAuACUUUdTsdT |
| AD-15641 | 234 | 25868 | 90 | uucGGuAcAuccucGAcGGdTsdT | 25869 | 91 | CCGUCGAGGAUGuACCGAAdTsdT |
| AD-15642 | 235 | 25870 | 92 | ucGGuAcAuccucGAcGGcdTsdT | 25871 | 93 | GCCGUCGAGGAUGuACCGAdTsdT |

TABLE 5-continued

Modified siRNAs targeting IL-6.

| Duplex Name | Target position of 5' base of sense strand (see FIG. 11) | S Oligo Name | SEQ ID NO: | Sense (S) Oligo Sequence (5' to 3') | AS Oligo Name | SEQ ID NO: | Antisense (AS) Oligo Sequence (5' to 3') |
|---|---|---|---|---|---|---|---|
| AD-15643 | 222 | 25872 | 94 | uuGAcAAAcAAAuucGGuAdTsdT | 25873 | 95 | uACCGAAUUUGUUUGUcAAdTsdT |
| AD-15644 | 809 | 25874 | 96 | AuGAGcGuuAGGAcAcuAudTsdT | 25875 | 97 | AuAGUGUCCuAACGCUcAUdTsdT |
| AD-15645 | 231 | 25876 | 98 | AAAuucGGuAcAuccucGAdTsdT | 25877 | 99 | UCGAGGAUGuACCGAAUUUdTsdT |
| AD-15646 | 425 | 25878 | 100 | GAGuuuGAGGuAuAccuAGdTsdT | 25879 | 101 | CuAGGuAuACCUcAAACUCdTsdT |
| AD-15647 | 542 | 25880 | 102 | AAucuAGAuGcAAuAAccAdTsdT | 25881 | 103 | UGGUuAUUGcAUCuAGAUUdTsdT |
| AD-15648 | 805 | 25882 | 104 | AAGuAuGAGcGuuAGGAcAdTsdT | 25883 | 105 | UGUCCuAACGCUcAUcUUUdTsdT |
| AD-15649 | 806 | 25884 | 106 | AGuAuGAGcGuuAGGAcAcdTsdT | 25885 | 107 | GUGUCCuAACGCUcAUACUdTsdT |
| AD-15650 | 1009 | 25886 | 108 | AGuGuAGGcuuAccucAAAdTsdT | 25887 | 109 | UUUGAGGuAAGCCuAcACUdTsdT |
| AD-15651 | 422 | 25888 | 110 | uuGGAGuuuGAGGuAuAccdTsdT | 25889 | 111 | GGuAuACCUcAAACUCcAAdTsdT |
| AD-15652 | 225 | 25890 | 112 | AcAAAcAAAuucGGuAcAudTsdT | 25891 | 113 | AUGuACCGAAUUUGUUUGUdTsdT |
| AD-15653 | 808 | 25892 | 114 | uAuGAGcGuuAGGAcAcuAdTsdT | 25893 | 115 | uAGUGUCCuAACGCUcAUdTsdT |
| AD-15654 | 210 | 25894 | 116 | cuucAGAAcGAAuuGAcAAdTsdT | 25895 | 117 | UUGUcAAUUCGUUCUGAAGdTsdT |
| AD-15655 | 680 | 25896 | 118 | cuGAGGGcucuucGGcAAAdTsdT | 25897 | 119 | UUUGCCGAAGAGCCCUcAGdTsdT |
| AD-15656 | 636 | 25898 | 120 | cucAucucAuucuGcGcAGdTsdT | 25899 | 121 | CUGCGcAGAAUGAGAUGAGdTsdT |
| AD-15657 | 1004 | 25900 | 122 | uGGAAAGuGuAGGcuuAccdTsdT | 25901 | 123 | GGuAAGCCuAcACUUUCcAdTsdT |
| AD-15658 | 691 | 25902 | 124 | ucGGcAAAuGuAGcAuGGGdTsdT | 25903 | 125 | CCcAUGCuAcAUUUGCCGAdTsdT |
| AD-15659 | 543 | 25904 | 126 | AucuAGAuGcAAuAAccAcdTsdT | 25905 | 127 | GUGGUuAUUGcAUCuAGAUdTsdT |
| AD-15660 | 811 | 25906 | 128 | GAGcGuuAGGAcAcuAuuudTsdT | 25907 | 129 | AAAuAGUGUCCuAACGCUCdTsdT |

TABLE 6

Unmodified siRNAs targeting IL-6.

| Position of 5' base of sense strand on transcript (see FIG. 11) | SEQ ID NO: | Sense (S) Oligo Sequence (5' to 3') | SEQ ID NO: | Antisense (AS) Oligo Sequence (5' to 3') |
|---|---|---|---|---|
| 803 | 130 | AAAAGUAUGAGCGUUAGGA | 131 | UCCUAACGCUCAUACUUUU |
| 223 | 132 | UGACAAACAAAUUCGGUAC | 133 | GUACCGAAUUUGUUUGUCA |
| 802 | 134 | UAAAAGUAUGAGCGUUAGG | 135 | CCUAACGCUCAUACUUUUA |
| 804 | 136 | AAAGUAUGAGCGUUAGGAC | 137 | GUCCUAACGCUCAUACUUU |
| 234 | 138 | UUCGGUACAUCCUCGACGG | 139 | CCGUCGAGGAUGUACCGAA |
| 235 | 140 | UCGGUACAUCCUCGACGGC | 141 | GCCGUCGAGGAUGUACCGA |
| 222 | 142 | UUGACAAACAAAUUCGGUA | 143 | UACCGAAUUUGUUUGUCAA |
| 809 | 144 | AUGAGCGUUAGGACACUAU | 145 | AUAGUGUCCUAACGCUCAU |
| 231 | 146 | AAAUUCGGUACAUCCUCGA | 147 | UCGAGGAUGUACCGAAUUU |

TABLE 6-continued

Unmodified siRNAs targeting IL-6.

| Position of 5' base of sense strand on transcript (see FIG. 11) | SEQ ID NO: | Sense (S) Oligo Sequence (5' to 3') | SEQ ID NO: | Antisense (AS) Oligo Sequence (5' to 3') |
|---|---|---|---|---|
| 425 | 148 | GAGUUUGAGGUAUACCUAG | 149 | CUAGGUAUACCUCAAACUC |
| 542 | 150 | AAUCUAGAUGCAAUAACCA | 151 | UGGUUAUUGCAUCUAGAUU |
| 805 | 152 | AAGUAUGAGCGUUAGGACA | 153 | UGUCCUAACGCUCAUACUU |
| 806 | 154 | AGUAUGAGCGUUAGGACAC | 155 | GUGUCCUAACGCUCAUACU |
| 1009 | 156 | AGUGUAGGCUUACCUCAAA | 157 | UUUGAGGUAAGCCUACACU |
| 422 | 158 | UUGGAGUUUGAGGUAUACC | 159 | GGUAUACCUCAAACUCCAA |
| 225 | 160 | ACAAACAAAUUCGGUACAU | 161 | AUGUACCGAAUUUGUUUGU |
| 808 | 162 | UAUGAGCGUUAGGACACUA | 163 | UAGUGUCCUAACGCUCAUA |
| 210 | 164 | CUUCAGAACGAAUUGACAA | 165 | UUGUCAAUUCGUUCUGAAG |
| 680 | 166 | CUGAGGGCUCUUCGGCAAA | 167 | UUUGCCGAAGAGCCCUCAG |
| 636 | 168 | CUCAUCUCAUUCUGCGCAG | 169 | CUGCGCAGAAUGAGAUGAG |
| 1004 | 170 | UGGAAAGUGUAGGCUUACC | 171 | GGUAAGCCUACACUUUCCA |
| 691 | 172 | UCGGCAAAUGUAGCAUGGG | 173 | CCCAUGCUACAUUUGCCGA |
| 543 | 174 | AUCUAGAUGCAAUAACCAC | 175 | GUGGUUAUUGCAUCUAGAU |
| 811 | 176 | GAGCGUUAGGACACUAUUU | 177 | AAAUAGUGUCCUAACGCUC |

TABLE 7 siRNAs targeting IL-6 and modified with 3' dinucleotide (NN) overhang.

| Position of 5' base of sense strand on transcript (see FIG. 11) | SEQ ID NO: | Sense (S) Oligo Sequence (5' to 3') | SEQ ID NO: | Antisense (AS) Oligo Sequence (5' to 3') |
|---|---|---|---|---|
| 803 | 178 | AAAGUAUGAGCGUUAGGANN | 179 | UCCUAACGCUCAUACUUUNN |
| 223 | 180 | UGACAAACAAAUUCGGUACNN | 181 | GUACCGAAUUUGUUUGUCANN |
| 802 | 182 | UAAAGUAUGAGCGUUAGGNN | 183 | CCUAACGCUCAUACUUUANN |
| 804 | 184 | AAGUAUGAGCGUUAGGACNN | 185 | GUCCUAACGCUCAUACUUUNN |
| 234 | 186 | UUCGGUACAUCCUCGACGGNN | 187 | CCGUCGAGGAUGUACCGAANN |
| 235 | 188 | UCGGUACAUCCUCGACGGCNN | 189 | GCCGUCGAGGAUGUACCGANN |
| 222 | 190 | UUGACAAACAAAUUCGGUANN | 191 | UACCGAAUUUGUUUGUCAANN |
| 809 | 192 | AUGAGCGUUAGGACACUAUNN | 193 | AUAGUGUCCUAACGCUCAUNN |
| 231 | 194 | AAAUUCGGUACAUCCUCGANN | 195 | UCGAGGAUGUACCGAAUUUNN |
| 425 | 196 | GAGUUUGAGGUAUACCUAGNN | 197 | CUAGGUAUACCUCAAACUCNN |
| 542 | 198 | AAUCUAGAUGCAAUAACCANN | 199 | UGGUUAUUGCAUCUAGAUUNN |
| 805 | 200 | AAGUAUGAGCGUUAGGACANN | 201 | UGUCCUAACGCUCAUACUUNN |
| 806 | 202 | AGUAUGAGCGUUAGGACACNN | 203 | GUGUCCUAACGCUCAUACUNN |

TABLE 7-continued siRNAs targeting IL-6 and modified with 3' dinucleotide (NN) overhang.

| Position of 5' base of sense strand on transcript (see FIG. 11) | SEQ ID NO: | Sense (S) Oligo Sequence (5' to 3') | SEQ ID NO: | Antisense (AS) Oligo Sequence (5' to 3') |
|---|---|---|---|---|
| 1009 | 204 | AGUGUAGGCUUACCUCAAANN | 205 | UUUGAGGUAAGCCUACACUNN |
| 422 | 206 | UUGGAGUUUGAGGUAUACCNN | 207 | GGUAUACCUCAAACUCCAANN |
| 225 | 208 | ACAAACAAAUUCGGUACAUNN | 209 | AUGUACCGAAUUUGUUUGUNN |
| 808 | 210 | UAUGAGCGUUAGGACACUANN | 211 | UAGUGUCCUAACGCUCAUANN |
| 210 | 212 | CUUCAGAACGAAUUGACAANN | 213 | UUGUCAAUUCGUUCUGAAGNN |
| 680 | 214 | CUGAGGGCUCUUCGGCAAANN | 215 | UUUGCCGAAGAGCCCUCAGNN |
| 636 | 216 | CUCAUCUCAUUCUGCGCAGNN | 217 | CUGCGCAGAAUGAGAUGAGNN |
| 1004 | 218 | UGGAAAGUGUAGGCUUACCNN | 219 | GGUAAGCCUACACUUUCCANN |
| 691 | 220 | UCGGCAAAUGUAGCAUGGGNN | 221 | CCCAUGCUACAUUUGCCGANN |
| 543 | 222 | AUCUAGAUGCAAUAACCACNN | 223 | GUGGUUAUUGCAUCUAGAUNN |
| 811 | 224 | GAGCGUUAGGACACUAUUUNN | 225 | AAAUAGUGUCCUAACGCUCNN |

TABLE 8 siRNAs targeting IL-6 and modified with 3' dithymidine (dTdT) overhang.

| Position of 5' base of sense strand on transcript (see FIG. 11) | SEQ ID NO: | Sense (S) Oligo Sequence (5' to 3') | SEQ ID NO: | Antisense (AS) Oligo Sequence (5' to 3') |
|---|---|---|---|---|
| 803 | 226 | AAAAGUAUGAGCGUUAGGAdTdT | 227 | UCCUAACGCUCAUACUUUUdTdT |
| 223 | 228 | UGACAAACAAAUUCGGUACdTdT | 229 | GUACCGAAUUUGUUUGUCAdTdT |
| 802 | 230 | UAAAAGUAUGAGCGUUAGGdTdT | 231 | CCUAACGCUCAUACUUUUAdTdT |
| 804 | 232 | AAAGUAUGAGCGUUAGGACdTdT | 233 | GUCCUAACGCUCAUACUUUdTdT |
| 234 | 234 | UUCGGUACAUCCUCGACGGdTdT | 235 | CCGUCGAGGAUGUACCGAAdTdT |
| 235 | 236 | UCGGUACAUCCUCGACGGCdTdT | 237 | GCCGUCGAGGAUGUACCGAdTdT |
| 222 | 238 | UUGACAAACAAAUUCGGUAdTdT | 239 | UACCGAAUUUGUUUGUCAAdTdT |
| 809 | 240 | AUGAGCGUUAGGACACUAUdTdT | 241 | AUAGUGUCCUAACGCUCAUdTdT |
| 231 | 242 | AAAUUCGGUACAUCCUCGAdTdT | 243 | UCGAGGAUGUACCGAAUUUdTdT |
| 425 | 244 | GAGUUUGAGGUAUACCUAGdTdT | 245 | CUAGGUAUACCUCAAACUCdTdT |
| 542 | 246 | AAUCUAGAUGCAAUAACCAdTdT | 247 | UGGUUAUUGCAUCUAGAUUdTdT |
| 805 | 248 | AAGUAUGAGCGUUAGGACAdTdT | 249 | UGUCCUAACGCUCAUACUUdTdT |
| 806 | 250 | AGUAUGAGCGUUAGGACACdTdT | 251 | GUGUCCUAACGCUCAUACUdTdT |
| 1009 | 252 | AGUGUAGGCUUACCUCAAAdTdT | 253 | UUUGAGGUAAGCCUACACUdTdT |
| 422 | 254 | UUGGAGUUUGAGGUAUACCdTdT | 255 | GGUAUACCUCAAACUCCAAdTdT |
| 225 | 256 | ACAAACAAAUUCGGUACAUdTdT | 257 | AUGUACCGAAUUUGUUUGUdTdT |

TABLE 8-continued siRNAs targeting IL-6 and modified with 3' dithymidine (dTdT) overhang.

| Position of 5' base of sense strand on transcript (see FIG. 11) | SEQ ID NO: | Sense (S) Oligo Sequence (5' to 3') | SEQ ID NO: | Antisense (AS) Oligo Sequence (5' to 3') |
|---|---|---|---|---|
| 808 | 258 | UAUGAGCGUUAGGACACUAdTdT | 259 | UAGUGUCCUAACGCUCAUAdTdT |
| 210 | 260 | CUUCAGAACGAAUUGACAAdTdT | 261 | UUGUCAAUUCGUUCUGAAGdTdT |
| 680 | 262 | CUGAGGGCUCUUCGGCAAAdTdT | 263 | UUUGCCGAAGAGCCCUCAGdTdT |
| 636 | 264 | CUCAUCUCAUUCUGCGCAGdTdT | 265 | CUGCGCAGAAUGAGAUGAGdTdT |
| 1004 | 266 | UGGAAAGUGUAGGCUUACCdTdT | 267 | GGUAAGCCUACACUUUCCAdTdT |
| 691 | 268 | UCGGCAAAUGUAGCAUGGGdTdT | 269 | CCCAUGCUACAUUUGCCGAdTdT |
| 543 | 270 | AUCUAGAUGCAAUAACCACdTdT | 271 | GUGGUUAUUGCAUCUAGAUdTdT |
| 811 | 272 | GAGCGUUAGGACACUAUUUdTdT | 273 | AAAUAGUGUCCUAACGCUCdTdT |

TABLE 9

Effect of IL-6 siRNAs on IL-6 and IL-8 gene expression.

| siRNA | IL-6 | IL-8 | Durability (days) |
|---|---|---|---|
| AD-15637 | + | + | x |
| AD-15638 | + | + | x |
| AD-15639 | + | + | x |
| AD-15640 | + | + | x |
| AD-15641 | + | – | x |
| AD-15642 | +/– | x | x |
| AD-15643 | + | x | x |
| AD-15644 | + | – | ≥14 |
| AD-15645 | + | x | x |
| AD-15646 | + | x | x |
| AD-15647 | – | x | x |
| AD-15648 | + | + | x |
| AD-15649 | + | + | x |
| AD-15650 | + | – | 3-7 |
| AD-15651 | – | x | x |
| AD-15652 | + | + | x |
| AD-15653 | + | + | x |
| AD-15654 | – | x | x |
| AD-15655 | + | x | x |
| AD-15656 | – | x | x |
| AD-15657 | + | + | 7-14 |
| AD-15658 | + | + | x |
| AD-15659 | + | + | x |
| AD-15660 | + | – | ≥14 |

– = no reduction of expression
+ = reduction of expression
+/– = small reduction of expression
x = not determined Other embodiments are in the claims.

We claim:

1. A method of treating glioblastoma multiforme (GBM), the method comprising administering to a human in need of such treatment a therapeutically effective amount of a first double-stranded ribonucleic acid (dsRNA) and a second dsRNA, wherein the first dsRNA comprises a sense strand and an antisense strand, wherein the antisense strand comprises a region of complementarity which is 19-24 nucleotides in length and which is fully complementary to at least a part of an mRNA encoding a deltaEGFR comprising nucleotides 1-334 and 1136-5616 of the nucleotide sequence of SEQ ID NO: 1, wherein the sense strand and the antisense strand form a duplex structure consisting of 15-30 base pairs; and wherein the second dsRNA comprises a sense strand and an antisense strand, wherein the antisense strand comprises a region of complementarity which is 19-24 nucleotides in length and which is fully complementary to at least a part of an mRNA encoding an IL-6 comprising the nucleotide sequence of SEQ ID NO: 274, wherein the sense strand and the antisense strand form a duplex structure consisting of 15-30 base pairs.

2. The method of claim 1, wherein the sense strand of the first dsRNA comprises a nucleotide sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:50, SEQ ID NO:52, SEQ ID NO:54, SEQ ID NO:56, SEQ ID NO:58, SEQ ID NO:60, SEQ ID NO:62, and SEQ ID NO:64, and wherein the antisense strand of the first dsRNA comprises a nucleotide sequence selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:51, SEQ ID NO:53, SEQ ID NO:55, SEQ ID NO:57, SEQ ID NO:59, SEQ ID NO:61, SEQ ID NO:63, and SEQ ID NO:65.

3. The method of claim 2, wherein the sense strand of the first dsRNA comprises a nucleotide sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:50, SEQ ID NO:52, SEQ ID NO:54, SEQ ID NO:56, SEQ ID NO:58, SEQ ID NO:60, SEQ ID NO:62, and SEQ ID NO:64, and wherein the antisense strand of the first dsRNA comprises a nucleotide sequence selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:51, SEQ ID NO:53, SEQ ID NO:55, SEQ ID NO:57, SEQ ID NO:59, SEQ ID NO:61, SEQ ID NO:63, and SEQ ID NO:65.

4. The method of claim 1, wherein the antisense strand of the first dsRNA is also fully complementary to at least a part of an mRNA encoding a wildtype Epidermal Growth Factor Receptor (EGFR) comprising the nucleotide sequence of SEQ ID NO: 1.

5. The method of claim 1, wherein the sense strand of the second dsRNA comprises a nucleotide sequence selected from the group consisting of SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172, SEQ ID NO:174, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232, SEQ ID NO:234, SEQ ID NO:236, SEQ ID NO:238, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:260, SEQ ID NO:262, SEQ ID NO:264, SEQ ID NO:266, SEQ ID NO:268, SEQ ID NO:270, and SEQ ID NO:272, and wherein the antisense strand of the second dsRNA comprises a nucleotide sequence selected from the group consisting of SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173, SEQ ID NO:175, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233, SEQ ID NO:235, SEQ ID NO:237, SEQ ID NO:239, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:261, SEQ ID NO:263, SEQ ID NO:265, SEQ ID NO:267, SEQ ID NO:269, SEQ ID NO:271, and SEQ ID NO:273.

6. The method of claim 5, wherein the sense strand of the second dsRNA comprises a nucleotide sequence of SEQ ID NO:96 or SEQ ID NO:128, and wherein the antisense strand of the second dsRNA comprises a nucleotide sequence of SEQ ID NO:97 or SEQ ID NO:129.

7. The method of claim 1, wherein the first dsRNA, the second dsRNA, or both, comprises at least one modified nucleotide.

8. The method of claim 7, wherein the at last one modified nucleotide is selected from the group consisting of a 2'-O-methyl modified nucleotide, a nucleotide comprising a 5'-phosphorothioate group, a terminal nucleotide linked to a cholesteryl derivative or dodecanoic acid bisdecylamide group, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

9. The method of claim 1, wherein the region of complementarity of the first dsRNA, the second dsRNA, or both, is between 19 and 21 nucleotides in length.

10. The method of claim 1, wherein the first dsRNA, the second dsRNA, or both, is 19 to 24 nucleotides in length.

11. The method of claim 1, wherein the first dsRNA and the second dsRNA are administered in the same composition.

12. The method of claim 1, wherein the first dsRNA and the second dsRNA are administered as part of a separate composition.

13. The method of claim 1,
wherein the first dsRNA comprises a sense strand and an antisense strand, wherein the sense strand of the first dsRNA comprises a nucleotide sequence of SEQ ID NO:8 or SEQ ID NO:56, and wherein the antisense strand of the first dsRNA comprises a nucleotide sequence of SEQ ID NO:9 or SEQ ID NO:57; and wherein the second dsRNA comprises a sense strand and an antisense strand, wherein the sense strand of the second dsRNA comprises a nucleotide sequence SEQ ID NO:96 or SEQ ID NO:128, and wherein the antisense strand of the second dsRNA comprises a nucleotide sequence of SEQ ID NO:97 or SEQ ID NO:129.

14. The method of claim 1, wherein the first dsRNA, the second dsRNA, or both, is 25 to 30 nucleotides in length.

15. The method of claim 9, wherein the first dsRNA, the second dsRNA, or both, is 19 to 21 nucleotides in length.

16. The method of claim 1, wherein the duplex structure of the first dsRNA, the second dsRNA, or both, consists of 18-25 base pairs.

17. The method of claim 1, wherein the duplex structure of the first dsRNA, the second dsRNA, or both, consists of 19-21 base pairs.

18. The method of claim 1, wherein at least one strand of the first dsRNA comprises a 3' overhang of 1-4 nucleotides in length.

19. The method of claim 18, wherein the 3' overhang is 1-2 nucleotides in length.

20. The method of claim 1, wherein at least one strand of the second dsRNA comprises a 3' overhang of 1-4 nucleotides in length.

21. The method of claim 20, wherein the 3' overhang is 1-2 nucleotides in length.

\* \* \* \* \*

SEQUENCE LISTING

```
<160> NUMBER OF SEQ ID NOS: 274

<210> SEQ ID NO 1
<211> LENGTH: 5616
<212> TYPE: DNA
<213> ORGANISM: Homo sapiens

<400> SEQUENCE: 1
ccccggcgca gcgcggccgc agcagcctcc gcccccgca cggtgtgagc gccgacgcg      60 gccgaggcgg ccggagtccc gagctagccc cggcggccgc cgccgcccag accggacgac    120
aggccacctc gtcggcgtcc gcccgagtcc ccgcctcgcc gccaacgcca caaccaccgc    180
gcacggcccc ctgactccgt ccagtattga tcgggagagc cggagcgagc tcttcgggga    240
gcagcgatgc gaccctccgg gacggccggg gcagcgctcc tggcgctgct ggctgcgctc    300
tgcccggcga gtcgggctct ggaggaaaag aaagtttgcc aaggcacgag taacaagctc    360
acgcagttgg gcactttga agatcatttt ctcagcctcc agaggatgtt caataactgt    420
gaggtggtcc ttgggaattt ggaaattacc tatgtgcaga ggaattatga tctttccttc    480
```

```
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca acaaccctgc cctgtgcaac    720
gtggagagca tccagtggcg ggacatagtc agcagtgact ttctcagcaa catgtcgatg    780
gacttccaga accacctggg cagctgccaa aagtgtgatc caagctgtcc caatgggagc    840
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gccccgggga gagcgactgc ctggtctgcc gcaaattccg agacgaagcc   1020
acgtgcaagg acacctgccc cccactcatg ctctacaacc ccaccacgta ccagatggat   1080
gtgaacccg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga taatttcagg aaacaaaaat ttgtgctatg caaatacaat aaactggaaa   1680
aaactgtttg ggacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag gcagggaatg cgtggacaag   1860
tgcaaccttc tggagggtga gccaaggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag gtcttgaagg ctgtccaacg   2160
aatgggccta agatcccgtc catcgccact gggatggtgg gggcctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag gactctgga tccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caagggcat gaactacttg gaggaccgtc gcttggtgca ccgcgacctg   2760
gcagccagga acgtactggt gaaaacaccg cagcatgtca agatcacaga ttttgggctg   2820
```

```
gccaaactgc tgggtgcgga agagaaagaa taccatgcag aaggaggcaa agtgcctatc    2880
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatctcctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggatga aagaatgcat ttgccaagtc ctacagactc caacttctac    3240
cgtgccctga tggatgaaga agacatggac gacgtggtgg atgccgacga gtacctcatc    3300
ccacagcagg gcttcttcag cagcccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttcttttccc    3780 aaggaagcca agccaaatgg catctttaag ggctccacag ctgaaaatgc agaataccta    3840
agggtcgcgc cacaaagcag tgaatttatt ggagcatgac cacggaggat agtatgagcc    3900
ctaaaaatcc agactctttc gatacccagg accaagccac agcaggtcct ccatcccaac    3960
agccatgccc gcattagctc ttagacccac agactggttt tgcaacgttt acaccgacta    4020
gccaggaagt acttccacct cgggcacatt ttgggaagtt gcattccttt gtcttcaaac    4080
tgtgaagcat ttacagaaac gcatccagca agaatattgt cccttttgagc agaaatttat    4140 cttttcaaaga ggtatatttg aaaaaaaaaa aaagtatatg tgaggatttt tattgattgg    4200
ggatcttgga gttttttcatt gtcgctattg attttttactt caatgggctc ttccaacaag    4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgccctg tcttgctgtc atgaaatcag    4680
caagagagga tgacacatca ataataact cggattccag cccacattgg attcatcagc    4740
atttggacca atagcccaca gctgagaatg tggaataccct aaggatagca ccgcttttgt    4800
tctcgcaaaa acgtatctcc taatttgagg ctcagatgaa atgcatcagg tccttttgggg    4860 catagatcag aagactacaa aaatgaagct gctctgaaat tcctttagc catcacccca    4920 accccccaaa attagtttgt gttacttatg gaagatagtt ttctcctttt acttcacttc    4980
aaaagctttt tactcaaaga gtatatgttc cctccaggtc agctgccccc aaacccctc    5040 cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactaggggtt tgaaattgat aatgctttca caacatttgc    5220
```

-continued

```
agatgtttta gaaggaaaaa agttccttcc taaaataatt tctctacaat tggaagattg    5280
gaagattcag ctagttagga gcccaccttt tttcctaatc tgtgtgtgcc ctgtaacctg    5340
actggttaac agcagtcctt tgtaaacagt gttttaaact ctcctagtca atatccaccc    5400
catccaattt atcaaggaag aaatggttca gaaatatttt tcagcctaca gttatgttca    5460
gtcacacaca catacaaaat gttcctttg cttttaaagt aattttgac tcccagatca    5520 gtcagagccc ctacagcatt gttaagaaag tatttgattt ttgtctcaat gaaataaaa    5580 ctatattcat ttccactcta aaaaaaaaaa aaaaaa                              5616
```

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 2
uggaggaaaa gaaagguaat t                                               21

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 3
uuaccuuucu uuuccuccat t                                               21

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 4
ggaggaaaag aaagguaaut t                                               21

<210> SEQ ID NO 5
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:

-continued

<221> NAME/KEY: source
<223> OTHER INFORMATION: /note="Description of Combined DNA/RNA
      Molecule: Synthetic oligonucleotide"

<400> SEQUENCE: 5
auuaccuuuc uuuuccucct t                                              21

<210> SEQ ID NO 6
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 6
gaggaaaaga aagguaauut t                                              21

<210> SEQ ID NO 7
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 7
aauuaccuuu cuuuuccuct t                                              21

<210> SEQ ID NO 8
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 8
cuggaggaaa agaaagguat t                                              21

<210> SEQ ID NO 9
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 9
uaccuuucuu uuccuccagt t                                              21

<210> SEQ ID NO 10
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10
aggaaaagaa agguaauuat t                                              21

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11
uaauuaccuu ucuuuuccut t                                              21

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12
ggaaaagaaa gguaauuaut t                                              21

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 13
auaauuaccu uucuuuucct t                                              21

<210> SEQ ID NO 14
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14
gaaagguaau uauguggugt t                                               21

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 15
caccacauaa uuaccuuuct t                                               21

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
agaaagguaa uuauguggut t                                               21

<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 17
accacauaau uaccuuucut t                                               21

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 18
acggugugag cgcccgacgt t                                              21

<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 19
cgucgggcgc ucacaccgut t                                              21

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 20
acagaucacg gcucgugcgt t                                              21

<210> SEQ ID NO 21
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 21
cgcacgagcc gugaucugut t                                              21

<210> SEQ ID NO 22
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 22
cacggcucgu gcguccgagt t                                              21

<210> SEQ ID NO 23
```

<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 23
cucggacgca cgagccgugt t                                              21

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 24
cgacaggcca ccucgucggt t                                              21

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 25
ccgacgaggu ggccugucgt t                                              21

<210> SEQ ID NO 26
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 26
gugacagauc acggcucgut t                                              21

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 27
acgagccgug aucugucact t                                           21

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 28
ucgucggcgu ccgcccgagt t                                           21

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 29
cucgggcgga cgccgacgat t                                           21

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 30
ccguccagua uugaucgggt t                                           21

<210> SEQ ID NO 31
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 31
```
cccgaucaau acuggacggt t                                              21

<210> SEQ ID NO 32
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 32
ggugacagau cacggcucgt t                                              21

<210> SEQ ID NO 33
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 33
cgagccguga ucugucacct t                                              21

<210> SEQ ID NO 34
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 34
ugccgcaaau uccgagacgt t                                              21

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 35
cgucucggaa uuugcggcat t                                              21

<210> SEQ ID NO 36
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 36
gcgccgugcg guucagcaat t                                              21

<210> SEQ ID NO 37
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 37
uugcugaacc gcacggcgct t                                              21

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 38
ccgcaaauuc cgagacgaat t                                              21

<210> SEQ ID NO 39
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 39
uucgucucgg aauuugcggt t                                              21

<210> SEQ ID NO 40
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

Molecule: Synthetic oligonucleotide"

<400> SEQUENCE: 40
ugccaaggca cgaguaacat t                                    21

<210> SEQ ID NO 41
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 41
uguuacucgu gccuuggcat t                                    21

<210> SEQ ID NO 42
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 42
gaggaaauau guacuacgat t                                    21

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 43
ucguaguaca uauuuccuct t                                    21

<210> SEQ ID NO 44
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 44
aggaaauccu gcauggcgct t                                    21

```
<210> SEQ ID NO 45
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 45
gcgccaugca ggauuuccut t                                          21

<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 46
ugcauggcgc cgugcgguut t                                          21

<210> SEQ ID NO 47
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 47
aaccgcacgg cgccaugcat t                                          21

<210> SEQ ID NO 48
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 48
ccaguggcgg gacauaguct t                                          21

<210> SEQ ID NO 49
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

```
                                Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 49
gacuaugucc cgccacuggt t                                                 21

<210> SEQ ID NO 50
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 50
uggaggaaaa gaaagguaat t                                                 21

<210> SEQ ID NO 51
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 51
uuaccuuucu uuccuccat t                                                  21

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 52
ggaggaaaag aaagguaaut t                                                 21

<210> SEQ ID NO 53
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 53
```
auuaccuuuc uuuuccucct t                                    21

<210> SEQ ID NO 54
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 54
gaggaaaaga aagguaauut t                                    21

<210> SEQ ID NO 55
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 55
aauuaccuuu cuuuuccuct t                                    21

<210> SEQ ID NO 56
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 56
cuggaggaaa agaaagguat t                                    21

<210> SEQ ID NO 57
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 57
uaccuuucuu uuccuccagt t                                    21

<210> SEQ ID NO 58
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 58
aggaaaagaa agguaauuat t                                              21

<210> SEQ ID NO 59
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 59
uaauuaccuu ucuuuuccut t                                              21

<210> SEQ ID NO 60
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 60
ggaaaagaaa gguaauuaut t                                              21

<210> SEQ ID NO 61
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 61
auaauuaccu uucuuuucct t                                              21

<210> SEQ ID NO 62
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 62
gaaagguaau uaugggugt t                                              21

<210> SEQ ID NO 63
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 63
caccacauaa uuaccuuuct t                                             21

<210> SEQ ID NO 64
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 64
agaaagguaa uuauguggut t                                             21

<210> SEQ ID NO 65
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 65
accacauaau uaccuuucut t                                             21

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 66
ugccgcaaau uccgagacgt t                                             21
```

```
<210> SEQ ID NO 67
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 67
cgucucggaa uuugcggcat t                                            21

<210> SEQ ID NO 68
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 68
gcgccgugcg guucagcaat t                                            21

<210> SEQ ID NO 69
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 69
uugcugaacc gcacggcgct t                                            21

<210> SEQ ID NO 70
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 70
ccgcaaauuc cgagacgaat t                                            21

<210> SEQ ID NO 71
<211> LENGTH: 21
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 71
uucgucucgg aauuugcggt t                                              21

<210> SEQ ID NO 72
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 72
ugccaaggca cgaguaacat t                                              21

<210> SEQ ID NO 73
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 73
uguuacucgu gccuuggcat t                                              21

<210> SEQ ID NO 74
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 74
gaggaaauau guacuacgat t                                              21

<210> SEQ ID NO 75
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 75
ucguaguaca uauuuccuct t                                               21

<210> SEQ ID NO 76
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 76
aggaaauccu gcauggcgct t                                               21

<210> SEQ ID NO 77
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 77
gcgccaugca ggauuuccut t                                               21

<210> SEQ ID NO 78
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 78
ugcauggcgc cgugcgguut t                                               21

<210> SEQ ID NO 79
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 79
aaccgcacgg cgccaugcat t                                               21

<210> SEQ ID NO 80
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 80
ccaguggcgg gacauaguct t                                           21

<210> SEQ ID NO 81
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 81
gacuaugucc cgccacuggt t                                           21

<210> SEQ ID NO 82
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 82
aaaaguauga gcguuaggat t                                           21

<210> SEQ ID NO 83
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 83
uccuaacgcu cauacuuuut t                                           21

<210> SEQ ID NO 84
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 84
ugacaaacaa auucgguact t                                              21

<210> SEQ ID NO 85
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 85
guaccgaauu uguuugucat t                                              21

<210> SEQ ID NO 86
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 86
uaaaaguaug agcguuaggt t                                              21

<210> SEQ ID NO 87
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 87
ccuaacgcuc auacuuuuat t                                              21

<210> SEQ ID NO 88
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 88
aaaguaugag cguuaggact t                                              21
```

-continued

<210> SEQ ID NO 89
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 89
guccuaacgc ucauacuuut t                                              21

<210> SEQ ID NO 90
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 90
uucgguacau ccucgacggt t                                              21

<210> SEQ ID NO 91
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 91
ccgucgagga uguaccgaat t                                              21

<210> SEQ ID NO 92
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 92
ucgguacauc cucgacggct t                                              21

<210> SEQ ID NO 93
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 93
gccgucgagg auguaccgat t                                              21

<210> SEQ ID NO 94
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 94
uugacaaaca aauucgguat t                                              21

<210> SEQ ID NO 95
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 95
uaccgaauuu guuugucaat t                                              21

<210> SEQ ID NO 96
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 96
augagcguua ggacacuaut t                                              21

<210> SEQ ID NO 97
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

```
<400> SEQUENCE: 97
auaguguccu aacgcucaut t                                          21

<210> SEQ ID NO 98
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 98
aaauucggua cauccucgat t                                          21

<210> SEQ ID NO 99
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 99
ucgaggaugu accgaauuut t                                          21

<210> SEQ ID NO 100
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 100
gaguuugagg uauaccuagt t                                          21

<210> SEQ ID NO 101
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 101
cuagguauac cucaaacuct t                                          21

<210> SEQ ID NO 102
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 102
aaucuagaug caauaaccat t                                                 21

<210> SEQ ID NO 103
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 103
ugguuauugc aucuagauut t                                                 21

<210> SEQ ID NO 104
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 104
aaguaugagc guuaggacat t                                                 21

<210> SEQ ID NO 105
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 105
uguccuaacg cucauacuut t                                                 21

<210> SEQ ID NO 106
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 106
aguaugagcg uuaggacact t                                              21

<210> SEQ ID NO 107
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 107
guguccuaac gcucauacut t                                              21

<210> SEQ ID NO 108
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 108
aguguaggcu uaccucaaat t                                              21

<210> SEQ ID NO 109
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 109
uuugagguaa gccuacacut t                                              21

<210> SEQ ID NO 110
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 110
```
uuggaguuug agguauaccu t				21

<210> SEQ ID NO 111
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 111
gguauaccuc aaacuccaau t				21

<210> SEQ ID NO 112
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 112
acaaacaaau ucgguacaut t				21

<210> SEQ ID NO 113
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 113
auguaccgaa uuuguuugut t				21

<210> SEQ ID NO 114
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 114
uaugagcguu aggacacuat t				21

<210> SEQ ID NO 115
<211> LENGTH: 21
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 115
uaguguccua acgcucauau t                                              21

<210> SEQ ID NO 116
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 116
cuucagaacg aauugacaat t                                              21

<210> SEQ ID NO 117
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 117
uugucaauuc guucugaagt t                                              21

<210> SEQ ID NO 118
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 118
cugagggcuc uucggcaaat t                                              21

<210> SEQ ID NO 119
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 119
uuugccgaag agcccucagt t                                          21

<210> SEQ ID NO 120
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 120
cucaucucau ucugcgcagt t                                          21

<210> SEQ ID NO 121
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 121
cugcgcagaa ugagaugagt t                                          21

<210> SEQ ID NO 122
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 122
uggaaagugu aggcuuacct t                                          21

<210> SEQ ID NO 123
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 123
gguaagccua cacuuuccat t                                          21

<210> SEQ ID NO 124
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 124
ucggcaaaug uagcaugggt t                                              21

<210> SEQ ID NO 125
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 125
cccaugcuac auuugccgat t                                              21

<210> SEQ ID NO 126
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 126
aucuagaugc aauaaccact t                                              21

<210> SEQ ID NO 127
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 127
gugguuauug caucuagaut t                                              21

<210> SEQ ID NO 128
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 128
gagcguuagg acacuauuut t                                              21

<210> SEQ ID NO 129
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 129
aaauaguguc cuaacgcuct t                                              21

<210> SEQ ID NO 130
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 130
aaaaguauga gcguuagga                                                19

<210> SEQ ID NO 131
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 131
uccuaacgcu cauacuuuu                                                19

<210> SEQ ID NO 132
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 132
ugacaaacaa auucgguac                                                19

<210> SEQ ID NO 133
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 133
guaccgaauu uguuuguca                                         19

<210> SEQ ID NO 134
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
uaaaaguaug agcguuagg                                         19

<210> SEQ ID NO 135
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
ccuaacgcuc auacuuuua                                         19

<210> SEQ ID NO 136
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
aaaguaugag cguuaggac                                         19

<210> SEQ ID NO 137
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
guccuaacgc ucauacuuu                                         19

<210> SEQ ID NO 138
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
uucgguacau ccucgacgg                                         19

<210> SEQ ID NO 139
<211> LENGTH: 19
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
ccgucgagga uguaccgaa                                                     19

<210> SEQ ID NO 140
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
ucgguacauc cucgacggc                                                     19

<210> SEQ ID NO 141
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
gccgucgagg auguaccga                                                     19

<210> SEQ ID NO 142
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
uugacaaaca aauucggua                                                     19

<210> SEQ ID NO 143
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
uaccgaauuu guuugucaa                                                     19

<210> SEQ ID NO 144
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
augagcguua ggacacuau                                                     19
```

<210> SEQ ID NO 145
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
auaguguccu aacgcucau                                                19

<210> SEQ ID NO 146
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
aaauucggua cauccucga                                                19

<210> SEQ ID NO 147
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
ucgaggaugu accgaauuu                                                19

<210> SEQ ID NO 148
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gaguuugagg uauaccuag                                                19

<210> SEQ ID NO 149
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
cuagguauac cucaaacuc                                                19

<210> SEQ ID NO 150
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 150
aaucuagaug caauaacca                                        19

<210> SEQ ID NO 151
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
ugguuauugc aucuagauu                                        19

<210> SEQ ID NO 152
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
aaguaugagc guuaggaca                                        19

<210> SEQ ID NO 153
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
uguccuaacg cucauacuu                                        19

<210> SEQ ID NO 154
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
aguaugagcg uuaggacac                                        19

<210> SEQ ID NO 155
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
guguccuaac gcucauacu                                        19

<210> SEQ ID NO 156
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
aguguaggcu uaccucaaa                                                 19

<210> SEQ ID NO 157
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
uuugagguaa gccuacacu                                                 19

<210> SEQ ID NO 158
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
uuggaguuug agguauacc                                                 19

<210> SEQ ID NO 159
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
gguauaccuc aaacuccaa                                                 19

<210> SEQ ID NO 160
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
acaaacaaau ucgguacau                                                 19

<210> SEQ ID NO 161
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
```
auguaccgaa uuuguuugu                                                19

<210> SEQ ID NO 162
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
uaugagcguu aggacacua                                                19

<210> SEQ ID NO 163
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
uaguguccua acgcucaua                                                19

<210> SEQ ID NO 164
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
cuucagaacg aauugacaa                                                19

<210> SEQ ID NO 165
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
uugucaauuc guucugaag                                                19

<210> SEQ ID NO 166
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
cugagggcuc uucggcaaa                                                19

<210> SEQ ID NO 167
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 167
uuugccgaag agcccucag                                                19

<210> SEQ ID NO 168
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 168
cucaucucau ucugcgcag                                                19

<210> SEQ ID NO 169
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 169
cugcgcagaa ugagaugag                                                19

<210> SEQ ID NO 170
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 170
uggaaagugu aggcuuacc                                                19

<210> SEQ ID NO 171
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 171
gguaagccua cacuuucca                                                19

<210> SEQ ID NO 172
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 172
ucggcaaaug uagcauggg                                                19

<210> SEQ ID NO 173

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
cccaugcuac auuugccga                                                19

<210> SEQ ID NO 174
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
aucuagaugc aauaaccac                                                19

<210> SEQ ID NO 175
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gugguuauug caucuagau                                                19

<210> SEQ ID NO 176
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
gagcguuagg acacuauuu                                                19

<210> SEQ ID NO 177
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
aaauaguguc cuaacgcuc                                                19

<210> SEQ ID NO 178
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

-continued

```
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 178
aaaaguauga gcguuaggan n                                                 21

<210> SEQ ID NO 179
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 179
uccuaacgcu cauacuuuun n                                                 21

<210> SEQ ID NO 180
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 180
ugacaaacaa auucgguacn n                                                 21

<210> SEQ ID NO 181
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 181
guaccgaauu uguuugucan n                                                 21

<210> SEQ ID NO 182
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 182
uaaaaguaug agcguuaggn n                                              21

<210> SEQ ID NO 183
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 183
ccuaacgcuc auacuuuuan n                                              21

<210> SEQ ID NO 184
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 184
aaaguaugag cguuaggacn n                                              21

<210> SEQ ID NO 185
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
```

-continued

```
<222> LOCATION: (20)..(21)
<223> OTHER INFORMATION: a, c, g, u, t, unknown or other

<400> SEQUENCE: 185
guccuaacgc ucauacuuun n                                              21

<210> SEQ ID NO 186
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 186
uucgguacau ccucgacggn n                                              21

<210> SEQ ID NO 187
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 187
ccgucgagga uguaccgaan n                                              21

<210> SEQ ID NO 188
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 188
ucgguacauc cucgacggcn n                                              21

<210> SEQ ID NO 189
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 189
gccgucgagg auguaccgan n                                              21

<210> SEQ ID NO 190
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 190
uugacaaaca aauucgguan n                                              21

<210> SEQ ID NO 191
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 191
uaccgaauuu guuugucaan n                                              21

<210> SEQ ID NO 192
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 192
```

-continued augagcguua ggacacuaun n         21

<210> SEQ ID NO 193
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 193
auaguguccu aacgcucaun n         21

<210> SEQ ID NO 194
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 194
aaauucggua cauccucgan n         21

<210> SEQ ID NO 195
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 195
ucgaggaugu accgaauuun n         21

<210> SEQ ID NO 196
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:

```
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 196
gaguuugagg uauaccuagn n                                            21

<210> SEQ ID NO 197
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 197
cuagguauac cucaaacucn n                                            21

<210> SEQ ID NO 198
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 198
aaucuagaug caauaaccan n                                            21

<210> SEQ ID NO 199
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 199
ugguuauugc aucuagauun n                                            21
```

-continued

```
<210> SEQ ID NO 200
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 200
aaguaugagc guuaggacan n                                             21

<210> SEQ ID NO 201
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 201
uguccuaacg cucauacuun n                                             21

<210> SEQ ID NO 202
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 202
aguaugagcg uuaggacacn n                                             21

<210> SEQ ID NO 203
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
```

<221> NAME/KEY: modified_base
<222> LOCATION: (20)..(21)
<223> OTHER INFORMATION: a, c, g, u, t, unknown or other

<400> SEQUENCE: 203
guguccuaac gcucauacun n                                              21

<210> SEQ ID NO 204
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 204
aguguaggcu uaccucaaan n                                              21

<210> SEQ ID NO 205
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 205
uuugagguaa gccuacacun n                                              21

<210> SEQ ID NO 206
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 206
uuggaguuug agguauaccn n                                              21

<210> SEQ ID NO 207
<211> LENGTH: 21
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 207
gguauaccuc aaacuccaan n                                         21

<210> SEQ ID NO 208
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 208
acaaacaaau ucgguacaun n                                         21

<210> SEQ ID NO 209
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 209
auguaccgaa uuuguuugun n                                         21

<210> SEQ ID NO 210
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other
```

```
<400> SEQUENCE: 210
uaugagcguu aggacacuan n                                              21

<210> SEQ ID NO 211
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 211
uaguguccua acgcucauan n                                              21

<210> SEQ ID NO 212
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 212
cuucagaacg aauugacaan n                                              21

<210> SEQ ID NO 213
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 213
uugucaauuc guucugaagn n                                              21

<210> SEQ ID NO 214
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 214
cugagggcuc uucggcaaan n                                              21

<210> SEQ ID NO 215
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 215
uuugccgaag agcccucagn n                                              21

<210> SEQ ID NO 216
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 216
cucaucucau ucugcgcagn n                                              21

<210> SEQ ID NO 217
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 217
cugcgcagaa ugagaugagn n                                              21
```

<210> SEQ ID NO 218
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 218
uggaaagugu aggcuuaccn n                                           21

<210> SEQ ID NO 219
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 219
gguaagccua cacuuuccan n                                           21

<210> SEQ ID NO 220
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 220
ucggcaaaug uagcaugggn n                                           21

<210> SEQ ID NO 221
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<220> FEATURE:
<221> NAME/KEY: modified_base
<222> LOCATION: (20)..(21)
<223> OTHER INFORMATION: a, c, g, u, t, unknown or other

<400> SEQUENCE: 221
cccaugcuac auuugccgan n                                              21

<210> SEQ ID NO 222
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 222
aucuagaugc aauaaccacn n                                              21

<210> SEQ ID NO 223
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 223
gugguuauug caucuagaun n                                              21

<210> SEQ ID NO 224
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 224
gagcguuagg acacuauuun n                                              21

<210> SEQ ID NO 225
<211> LENGTH: 21
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (20)..(21)
<223> OTHER INFORMATION: a, c, g, u, t, unknown or other

<400> SEQUENCE: 225
aaauaguguc cuaacgcucn n                                              21

<210> SEQ ID NO 226
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 226
aaaaguauga gcguuaggat t                                              21

<210> SEQ ID NO 227
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 227
uccuaacgcu cauacuuuut t                                              21

<210> SEQ ID NO 228
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 228
ugacaaacaa auucgguact t                                              21

<210> SEQ ID NO 229
<211> LENGTH: 21
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 229
guaccgaauu uguuugucat t                                              21

<210> SEQ ID NO 230
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 230
uaaaaguaug agcguuaggt t                                              21

<210> SEQ ID NO 231
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 231
ccuaacgcuc auacuuuuat t                                              21

<210> SEQ ID NO 232
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 232
aaaguaugag cguuaggact t                                              21

<210> SEQ ID NO 233
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 233
guccuaacgc ucauacuuut t                                              21

<210> SEQ ID NO 234
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 234
uucgguacau ccucgacggt t                                              21

<210> SEQ ID NO 235
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 235
ccgucgagga uguaccgaat t                                              21

<210> SEQ ID NO 236
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 236
ucgguacauc cucgacggct t                                              21

<210> SEQ ID NO 237
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 237
gccgucgagg auguaccgat t                                              21

<210> SEQ ID NO 238
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 238
uugacaaaca aauucgguat t                                          21

<210> SEQ ID NO 239
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 239
uaccgaauuu guuugucaat t                                          21

<210> SEQ ID NO 240
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 240
augagcguua ggacacuaut t                                          21

<210> SEQ ID NO 241
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 241
auaguguccu aacgcucaut t                                          21

<210> SEQ ID NO 242
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 242
aaauucggua cauccucgat t                                              21

<210> SEQ ID NO 243
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 243
ucgaggaugu accgaauuut t                                              21

<210> SEQ ID NO 244
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 244
gaguuugagg uauaccuagt t                                              21

<210> SEQ ID NO 245
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 245
cuagguauac cucaaacuct t                                              21

<210> SEQ ID NO 246
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 246
aaucuagaug caauaaccat t                                              21
```

<210> SEQ ID NO 247
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 247
ugguuauugc aucuagauut t                                      21

<210> SEQ ID NO 248
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 248
aaguaugagc guuaggacat t                                      21

<210> SEQ ID NO 249
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 249
uguccuaacg cucauacuut t                                      21

<210> SEQ ID NO 250
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 250
aguaugagcg uuaggacact t                                      21

<210> SEQ ID NO 251
<211> LENGTH: 21
<212> TYPE: DNA
<213> ORGANISM: Artificial Sequence
<220> FEATURE:

<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 251
guguccuaac gcucauacut t                                              21

<210> SEQ ID NO 252
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 252
aguguaggcu uaccucaaat t                                              21

<210> SEQ ID NO 253
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 253
uuugagguaa gccuacacut t                                              21

<210> SEQ ID NO 254
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 254
uuggaguuug agguauacct t                                              21

<210> SEQ ID NO 255
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 255
gguauaccuc aaacuccaat t                                              21

<210> SEQ ID NO 256
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 256
acaaacaaau ucgguacaut t                                              21

<210> SEQ ID NO 257
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 257
auguaccgaa uuuguuugut t                                              21

<210> SEQ ID NO 258
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 258
uaugagcguu aggacacuat t                                              21

<210> SEQ ID NO 259
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 259
uaguguccua acgcucauat t                                              21

<210> SEQ ID NO 260

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 260
cuucagaacg aauugacaat t                                              21

<210> SEQ ID NO 261
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 261
uugucaauuc guucugaagt t                                              21

<210> SEQ ID NO 262
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 262
cugagggcuc uucggcaaat t                                              21

<210> SEQ ID NO 263
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 263
uuugccgaag agcccucagt t                                              21

<210> SEQ ID NO 264
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 264
cucaucucau ucugcgcagt t                                              21

<210> SEQ ID NO 265
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 265
cugcgcagaa ugagaugagt t                                              21

<210> SEQ ID NO 266
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 266
uggaaagugu aggcuuacct t                                              21

<210> SEQ ID NO 267
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 267
gguaagccua cacuuuccat t                                              21

<210> SEQ ID NO 268
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 268
```
ucggcaaaug uagcaugggt t         21

<210> SEQ ID NO 269
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 269
cccaugcuac auuugccgat t         21

<210> SEQ ID NO 270
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 270
aucuagaugc aauaaccact t         21

<210> SEQ ID NO 271
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 271
gugguuauug caucuagaut t         21

<210> SEQ ID NO 272
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 272
gagcguuagg acacuauuut t         21

<210> SEQ ID NO 273
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 273
aaauaguguc cuaacgcuct t                                              21

<210> SEQ ID NO 274
<211> LENGTH: 1131
<212> TYPE: DNA
<213> ORGANISM: Homo sapiens

<400> SEQUENCE: 274
cattctgccc tcgagcccac cgggaacgaa agagaagctc tatctcccct ccaggagccc      60
agctatgaac tccttctcca caagcgcctt cggtccagtt gccttctccc tggggctgct     120
cctggtgttg cctgctgcct tccctgcccc agtaccccca ggagaagatt ccaaagatgt     180
agccgcccca cacagacagc cactcacctc ttcagaacga attgacaaac aaattcggta     240
catcctcgac ggcatctcag ccctgagaaa ggagacatgt aacaagagta acatgtgtga     300
aagcagcaaa gaggcactgg cagaaaacaa cctgaacctt ccaaagatgg ctgaaaaaga     360
tggatgcttc caatctggat tcaatgagga gacttgcctg gtgaaaatca tcactggtct     420
tttggagttt gaggtatacc tagagtacct ccagaacaga tttgagagta gtgaggaaca     480
agccagagct gtgcagatga gtacaaaagt cctgatccag ttcctgcaga aaaaggcaaa     540
gaatctagat gcaataacca cccctgaccc aaccacaaat gccagcctgc tgacgaagct     600
gcaggcacag aaccagtggc tgcaggacat gacaactcat ctcattctgc gcagctttaa     660
ggagttcctg cagtccagcc tgagggctct tcggcaaatg tagcatgggc acctcagatt     720
gttgttgtta atgggcattc cttcttctgg tcagaaacct gtccactggg cacagaactt     780
atgttgttct ctatggagaa ctaaaagtat gagcgttagg acactatttt aattattttt     840
aatttattaa tatttaaata tgtgaagctg agttaattta tgtaagtcat atttatattt     900
ttaagaagta ccacttgaaa cattttatgt attagttttg aaataataat ggaaagtggc     960
tatgcagttt gaatatcctt tgtttcagag ccagatcatt tcttggaaag tgtaggctta    1020
cctcaaataa atggctaact tatacatatt tttaaagaaa tatttatatt gtatttatat    1080
aatgtataaa tggttttat accaataaat ggcattttaa aaaattcagc a              1131
```